US 8,852,195 B2

(12) United States Patent
Justin et al.

(10) Patent No.: US 8,852,195 B2
(45) Date of Patent: Oct. 7, 2014

(54) GUIDE TEMPLATES FOR SURGICAL IMPLANTS AND RELATED METHODS

(75) Inventors: Daniel F. Justin, Logan, UT (US); E. Marlowe Goble, Alta, WY (US); Robert A. Hodorek, Warsaw, IN (US); Carlyle J. Creger, Logan, UT (US)

(73) Assignee: Zimmer, Inc., Warsaw, IN (US)

(*) Notice: Subject to any disclaimer, the term of this patent is extended or adjusted under 35 U.S.C. 154(b) by 2166 days.

(21) Appl. No.: 11/040,501

(22) Filed: Jan. 21, 2005

(65) Prior Publication Data

US 2006/0009854 A1 Jan. 12, 2006

Related U.S. Application Data

(63) Continuation-in-part of application No. 10/901,941, filed on Jul. 28, 2004.

(60) Provisional application No. 60/586,706, filed on Jul. 9, 2004.

(51) Int. Cl.
| | | |
|---|---|---|
| *A61B 17/32* | (2006.01) | |
| *A61F 2/38* | (2006.01) | |
| *A61B 17/16* | (2006.01) | |
| *A61B 17/17* | (2006.01) | |
| *A61F 2/40* | (2006.01) | |
| *A61F 2/32* | (2006.01) | |
| *A61F 2/42* | (2006.01) | |

(52) U.S. Cl.
CPC .............. *A61B 17/1764* (2013.01); *A61F 2/40* (2013.01); *A61F 2/38* (2013.01); *A61F 2/32* (2013.01); *A61F 2/42* (2013.01); *A61B 17/1675* (2013.01); *A61F 2/3877* (2013.01); *A61B 17/1662* (2013.01); *A61F 2002/3895* (2013.01); *A61F 2/3804* (2013.01)
USPC ............................................ 606/87

(58) Field of Classification Search
USPC ................ 606/86 R, 87, 88, 96, 102, 84, 85
See application file for complete search history.

(56) References Cited

U.S. PATENT DOCUMENTS

| | | |
|---|---|---|
| 3,748,662 A | 7/1973 | Helfet |
| 3,806,961 A | 4/1974 | Muller |

(Continued)

FOREIGN PATENT DOCUMENTS

| | | |
|---|---|---|
| CA | 2155556 A1 | 6/1995 |
| DE | 2901009 A1 | 7/1980 |

(Continued)

OTHER PUBLICATIONS

*Vanguard™ PFR Patellofemoral Replacement System*, Surgical Technique Pamphlet, by Biomet Orthopedics, Inc. (publication date unknown).

(Continued)

*Primary Examiner* — Pedro Philogene
*Assistant Examiner* — David Comstock
(74) *Attorney, Agent, or Firm* — Schwegman Lundberg & Woessner, P.A.

(57) ABSTRACT

A guide template for use in resurfacing a portion of a bone includes a body adapted for positioning over a natural or resected articulation surface of the bone. The body has a top surface and an opposing bottom surface that each extend between a proximal end and an opposing distal end. The body at least partially bounds an opening extending between the top surface and the bottom surface. At least a portion of the top surface or the bottom surface has a convex curvature or a concave curvature that extends between the proximal end and the opposing distal end. At least three spaced apart supports project below the bottom surface of the body such that the body can be supported by the supports. Fasteners are provided for securing the body to the bone.

25 Claims, 47 Drawing Sheets

(56) References Cited

U.S. PATENT DOCUMENTS

| | | | |
|---|---|---|---|
| 3,852,830 A | 12/1974 | Marmor | |
| 4,000,525 A | 1/1977 | Klawitter et al. | |
| 4,081,866 A | 4/1978 | Upshaw et al. | |
| 4,151,615 A | 5/1979 | Hall | |
| 4,217,666 A | 8/1980 | Averill | |
| 4,224,696 A | 9/1980 | Murray et al. | |
| 4,309,778 A | 1/1982 | Buechel et al. | |
| 4,340,978 A | 7/1982 | Buechel et al. | |
| 4,470,158 A | 9/1984 | Pappas et al. | |
| 4,479,271 A | 10/1984 | Bolesky et al. | |
| 4,502,161 A | 3/1985 | Wall | |
| 4,627,853 A | 12/1986 | Campbell et al. | |
| 4,657,549 A | 4/1987 | Keller | |
| 4,662,889 A | 5/1987 | Zichner et al. | |
| 4,673,407 A | 6/1987 | Martin | |
| 4,719,908 A | 1/1988 | Averill et al. | |
| 4,721,104 A | 1/1988 | Kaufman et al. | |
| 4,822,366 A | 4/1989 | Bolesky | |
| 4,838,891 A | 6/1989 | Branemark et al. | |
| 4,919,671 A | 4/1990 | Karpf | |
| 4,927,421 A | 5/1990 | Goble et al. | |
| 4,950,270 A | 8/1990 | Bowman et al. | |
| 4,963,153 A | 10/1990 | Noesberger et al. | |
| 4,964,868 A | 10/1990 | Bloebaum | |
| 5,019,103 A | 5/1991 | Van Zile et al. | |
| 5,035,699 A | 7/1991 | Coates | |
| 5,037,439 A | 8/1991 | Albrektsson et al. | |
| 5,092,895 A | 3/1992 | Albrektsson et al. | |
| 5,100,409 A | 3/1992 | Coates et al. | |
| 5,112,337 A | 5/1992 | Paulos et al. | |
| 5,116,375 A | 5/1992 | Hofmann | |
| 5,122,144 A | 6/1992 | Bert et al. | |
| 5,123,928 A | 6/1992 | Moser | |
| 5,147,406 A | 9/1992 | Houston et al. | |
| 5,163,940 A | 11/1992 | Bourque | |
| 5,176,684 A | 1/1993 | Ferrante et al. | |
| 5,180,383 A | 1/1993 | Haydon | |
| 5,181,925 A | 1/1993 | Houston et al. | |
| 5,226,916 A | 7/1993 | Goodfellow et al. | |
| 5,258,015 A | 11/1993 | Li et al. | |
| 5,258,032 A | 11/1993 | Bertin | |
| 5,271,737 A | 12/1993 | Baldwin et al. | |
| 5,282,803 A | 2/1994 | Lackey | |
| 5,282,868 A | 2/1994 | Bahler | |
| 5,312,408 A | 5/1994 | Brown | |
| 5,312,411 A | 5/1994 | Steele et al. | |
| 5,330,534 A | 7/1994 | Herrington et al. | |
| 5,334,205 A | 8/1994 | Chain | |
| 5,336,266 A | 8/1994 | Caspari et al. | |
| 5,344,423 A | 9/1994 | Dietz et al. | |
| 5,346,496 A | 9/1994 | Penning | |
| 5,358,529 A | 10/1994 | Davidson | |
| 5,358,530 A | 10/1994 | Hodorek | |
| 5,364,402 A | 11/1994 | Mumme et al. | |
| D357,315 S | 4/1995 | Dietz | |
| 5,405,395 A | 4/1995 | Coates | |
| 5,405,398 A | 4/1995 | Buford, III et al. | |
| 5,413,606 A | 5/1995 | Fisk et al. | |
| 5,417,695 A | 5/1995 | Axelson, Jr. | |
| 5,474,559 A | 12/1995 | Bertin et al. | |
| 5,484,446 A | 1/1996 | Burke et al. | |
| 5,486,180 A | 1/1996 | Dietz et al. | |
| 5,489,311 A | 2/1996 | Cipolletti | |
| 5,507,812 A | 4/1996 | Moore | |
| 5,549,683 A | 8/1996 | Bonutti | |
| 5,549,684 A | 8/1996 | Amino et al. | |
| 5,549,688 A | 8/1996 | Ries et al. | |
| 5,556,433 A | 9/1996 | Gabriel et al. | |
| 5,569,259 A | 10/1996 | Ferrante et al. | |
| 5,571,196 A | 11/1996 | Stein | |
| 5,571,203 A | 11/1996 | Masini | |
| 5,578,039 A | 11/1996 | Vendrely et al. | |
| D376,202 S | 12/1996 | Burke et al. | |
| 5,593,411 A | 1/1997 | Stalcup et al. | |
| 5,609,642 A | 3/1997 | Johnson et al. | |
| 5,634,927 A | 6/1997 | Houston et al. | |
| 5,642,550 A | 7/1997 | Maryuama et al. | |
| 5,645,602 A | 7/1997 | Albrektsson et al. | |
| 5,653,714 A | 8/1997 | Dietz et al. | |
| 5,674,224 A | 10/1997 | Howell et al. | |
| 5,702,397 A | 12/1997 | Goble et al. | |
| 5,702,459 A | 12/1997 | Hummer et al. | |
| 5,702,464 A | 12/1997 | Lackey et al. | |
| 5,702,466 A | 12/1997 | Pappas et al. | |
| 5,709,689 A | 1/1998 | Ferrante et al. | |
| 5,725,584 A | 3/1998 | Walker et al. | |
| 5,728,162 A | 3/1998 | Eckhoff | |
| 5,735,856 A | 4/1998 | McCue et al. | |
| 5,741,262 A | 4/1998 | Albrektsson et al. | |
| 5,743,915 A | 4/1998 | Bertin et al. | |
| 5,746,771 A | 5/1998 | Clement et al. | |
| 5,755,800 A | 5/1998 | O'Neil et al. | |
| 5,755,803 A | 5/1998 | Haines et al. | |
| 5,766,255 A | 6/1998 | Slamin et al. | |
| 5,769,855 A | 6/1998 | Bertin et al. | |
| 5,776,201 A | 7/1998 | Colleran et al. | |
| 5,782,924 A | 7/1998 | Johnson | |
| 5,782,925 A | 7/1998 | Collazo et al. | |
| 5,800,553 A | 9/1998 | Albrektsson et al. | |
| 5,824,098 A | 10/1998 | Stein | |
| 5,824,105 A | 10/1998 | Ries et al. | |
| 5,860,981 A | 1/1999 | Bertin et al. | |
| 5,871,539 A | 2/1999 | Pappas | |
| 5,871,545 A | 2/1999 | Goodfellow et al. | |
| 5,879,354 A | 3/1999 | Haines et al. | |
| 5,879,391 A | 3/1999 | Slamin | |
| 5,885,035 A | 3/1999 | Hoffschneider | |
| 5,902,340 A | 5/1999 | White et al. | |
| 5,906,643 A | 5/1999 | Walker | |
| 5,908,424 A | 6/1999 | Bertin et al. | |
| 5,911,758 A | 6/1999 | Oehy et al. | |
| 5,964,808 A | 10/1999 | Blaha et al. | |
| 5,968,045 A | 10/1999 | Frazier | |
| 6,013,103 A | 1/2000 | Kaufman et al. | |
| 6,063,091 A | 5/2000 | Lombardo et al. | |
| 6,068,648 A | 5/2000 | Cole et al. | |
| 6,071,311 A | 6/2000 | O'Neil et al. | |
| 6,077,270 A | 6/2000 | Katz | |
| 6,102,954 A | 8/2000 | Albrektsson et al. | |
| 6,123,729 A | 9/2000 | Insall et al. | |
| 6,126,693 A | 10/2000 | O'Neil et al. | |
| 6,132,468 A | 10/2000 | Mansmann | |
| 6,159,216 A | 12/2000 | Burkinshaw et al. | |
| 6,162,234 A | 12/2000 | Freedland et al. | |
| 6,165,223 A | 12/2000 | Metzger et al. | |
| 6,168,629 B1 | 1/2001 | Timoteo | |
| 6,171,340 B1 | 1/2001 | Mcdowell et al. | |
| 6,171,342 B1 | 1/2001 | O'Neil et al. | |
| 6,190,415 B1 | 2/2001 | Cooke et al. | |
| 6,197,064 B1 | 3/2001 | Haines et al. | |
| 6,214,051 B1 | 4/2001 | Badorf et al. | |
| 6,214,952 B1 | 4/2001 | Sadatoshi et al. | |
| 6,235,060 B1 | 5/2001 | Kubein-Meesenburg et al. | |
| 6,245,110 B1 | 6/2001 | Grundei et al. | |
| 6,299,645 B1 | 10/2001 | Ogden | |
| 6,319,271 B1 | 11/2001 | Schwartz et al. | |
| 6,355,045 B1 | 3/2002 | Gundlapalli et al. | |
| 6,364,911 B1 | 4/2002 | Schmotzer et al. | |
| 6,368,326 B1 | 4/2002 | Dakin et al. | |
| 6,383,222 B1 | 5/2002 | Badorf | |
| 6,402,786 B1 | 6/2002 | Insall et al. | |
| 6,416,552 B1 | 7/2002 | Hoeppner et al. | |
| 6,436,101 B1 | 8/2002 | Hamada | |
| 6,440,139 B2 * | 8/2002 | Michelson | 606/80 |
| 6,461,373 B2 | 10/2002 | Wyman et al. | |
| 6,478,799 B1 | 11/2002 | Williamson | |
| 6,482,209 B1 | 11/2002 | Engh et al. | |
| 6,508,841 B2 | 1/2003 | Martin et al. | |
| 6,520,964 B2 | 2/2003 | Tallarida et al. | |
| 6,544,267 B1 | 4/2003 | Cole et al. | |
| 6,554,838 B2 | 4/2003 | McGovern et al. | |
| 6,589,283 B1 | 7/2003 | Metzger et al. | |
| 6,610,067 B2 | 8/2003 | Tallarida et al. | |
| 6,616,696 B1 | 9/2003 | Merchant | |

(56) References Cited

U.S. PATENT DOCUMENTS

| | | |
|---|---|---|
| 6,620,168 B1 | 9/2003 | Lombardo et al. |
| 6,652,587 B2 | 11/2003 | Felt et al. |
| 6,663,670 B2 | 12/2003 | Rogers et al. |
| 6,679,917 B2 | 1/2004 | Ek |
| 6,712,824 B2 | 3/2004 | Millard et al. |
| 6,712,856 B1 | 3/2004 | Carignan et al. |
| 6,736,819 B2 | 5/2004 | Tipirneni |
| 6,743,258 B1 | 6/2004 | Keller |
| 6,749,638 B1 | 6/2004 | Saladiono |
| 6,773,461 B2 | 8/2004 | Meyers et al. |
| 6,797,006 B2 | 9/2004 | Hodorek |
| 6,866,683 B2 | 3/2005 | Gerbec et al. |
| 6,905,514 B2 | 6/2005 | Carignan et al. |
| 6,969,393 B2 | 11/2005 | Pinczewski et al. |
| 6,994,725 B1 | 2/2006 | Goble |
| 7,150,761 B2 | 12/2006 | Justin et al. |
| 7,250,061 B2 | 7/2007 | Jacobsson et al. |
| 7,771,483 B2 | 8/2010 | Justin et al. |
| 7,806,898 B2 | 10/2010 | Justin et al. |
| 7,867,236 B2 | 1/2011 | Hodorek et al. |
| 7,867,280 B2 | 1/2011 | Goble et al. |
| 7,922,772 B2 | 4/2011 | Goble et al. |
| 8,062,377 B2 | 11/2011 | Haines |
| 8,088,167 B2 | 1/2012 | Haines |
| 8,236,060 B2 | 8/2012 | Justin et al. |
| 8,460,391 B2 | 6/2013 | Justin et al. |
| 2001/0016778 A1 | 8/2001 | Badorf et al. |
| 2002/0019637 A1 | 2/2002 | Frey et al. |
| 2002/0022890 A1 | 2/2002 | Jacobsson et al. |
| 2002/0055783 A1 | 5/2002 | Tallarida et al. |
| 2002/0107520 A1 | 8/2002 | Hoffman |
| 2002/0138150 A1 | 9/2002 | Leclercq |
| 2002/0147498 A1 | 10/2002 | Tallarida et al. |
| 2002/0198528 A1 | 12/2002 | Engh et al. |
| 2003/0004577 A1 | 1/2003 | Running |
| 2003/0028196 A1 | 2/2003 | Bonutti |
| 2003/0033018 A1 | 2/2003 | Merchant |
| 2003/0060887 A1 | 3/2003 | Ek |
| 2003/0093156 A1 | 5/2003 | Metzger et al. |
| 2003/0100907 A1 | 5/2003 | Rosa et al. |
| 2003/0120276 A1 | 6/2003 | Tallarida et al. |
| 2003/0130665 A1 | 7/2003 | Pinczewski et al. |
| 2003/0153977 A1 | 8/2003 | Suguro et al. |
| 2003/0153979 A1 | 8/2003 | Hughes et al. |
| 2003/0158606 A1 | 8/2003 | Coon et al. |
| 2003/0181984 A1 | 9/2003 | Abendschein |
| 2003/0225456 A1 | 12/2003 | Ek |
| 2003/0225457 A1 | 12/2003 | Justin et al. |
| 2003/0225458 A1 | 12/2003 | Donkers et al. |
| 2004/0015170 A1 | 1/2004 | Tallarida et al. |
| 2004/0102582 A1 | 5/2004 | Dang et al. |
| 2004/0106928 A1 | 6/2004 | Ek |
| 2004/0117023 A1 | 6/2004 | Gerbec et al. |
| 2004/0117024 A1 | 6/2004 | Gerbec et al. |
| 2004/0143336 A1 | 7/2004 | Burkinshaw |
| 2004/0148030 A1 | 7/2004 | Ek |
| 2004/0236428 A1 | 11/2004 | Burkinshaw et al. |
| 2005/0137708 A1 | 6/2005 | Clark |
| 2005/0143830 A1 | 6/2005 | Marcinek et al. |
| 2005/0143831 A1 | 6/2005 | Justin et al. |
| 2005/0143833 A1 | 6/2005 | Merchant |
| 2005/0149044 A1 | 7/2005 | Justin et al. |
| 2005/0154398 A1 | 7/2005 | Miniaci et al. |
| 2005/0154471 A1 | 7/2005 | Aram et al. |
| 2005/0177242 A1 | 8/2005 | Lotke |
| 2005/0192588 A1 | 9/2005 | Garcia |
| 2005/0267584 A1 | 12/2005 | Burdulis, Jr. et al. |
| 2006/0004461 A1 | 1/2006 | Justin et al. |
| 2006/0009774 A1 | 1/2006 | Goble et al. |
| 2006/0009776 A1 | 1/2006 | Justin |
| 2006/0009853 A1 | 1/2006 | Justin et al. |
| 2006/0009854 A1 | 1/2006 | Justin et al. |
| 2006/0122616 A1 | 6/2006 | Bennett et al. |
| 2006/0167460 A1 | 7/2006 | Pinczewski et al. |
| 2006/0200161 A1 | 9/2006 | Plaskos et al. |
| 2006/0276796 A1 | 12/2006 | Creger |
| 2006/0293682 A1 | 12/2006 | Justin |
| 2007/0123992 A1 | 5/2007 | Sanford |
| 2007/0288029 A1 | 12/2007 | Justin |
| 2008/0119940 A1 | 5/2008 | Otto et al. |
| 2008/0154270 A1 | 6/2008 | Haines et al. |
| 2008/0188855 A1 | 8/2008 | Brown et al. |
| 2008/0188942 A1 | 8/2008 | Brown et al. |
| 2010/0042224 A1 | 2/2010 | Otto et al. |

FOREIGN PATENT DOCUMENTS

| | | |
|---|---|---|
| DE | 3305237 A1 | 8/1983 |
| DE | 3 917 285 | 11/1990 |
| DE | 19716879 A1 | 11/1998 |
| DE | 69528655 T2 | 7/2003 |
| EP | 0376658 A2 | 7/1990 |
| EP | 0376658 A3 | 7/1990 |
| EP | 0336774 B1 | 12/1992 |
| EP | 0 554 959 A1 | 8/1993 |
| EP | 0600806 A1 | 6/1994 |
| EP | 0 502 737 B1 | 11/1995 |
| EP | 0681817 A1 | 11/1995 |
| EP | 0522822 B1 | 12/1995 |
| EP | 0731676 B1 | 5/1997 |
| EP | 0600806 B1 | 6/1997 |
| EP | 0 850 606 A3 | 7/1998 |
| EP | 0781117 B1 | 7/1998 |
| EP | 0336774 A1 | 10/1998 |
| EP | 0891756 A2 | 1/1999 |
| EP | 0916322 A2 | 5/1999 |
| EP | 0913135 A3 | 9/1999 |
| EP | 0941719 A2 | 9/1999 |
| EP | 0674887 B1 | 10/1999 |
| EP | 0980679 A2 | 2/2000 |
| EP | 0985386 A2 | 3/2000 |
| EP | 0986994 A2 | 3/2000 |
| EP | 1216669 A3 | 6/2002 |
| EP | 0749734 B1 | 9/2002 |
| EP | 1245204 A2 | 10/2002 |
| EP | 0714645 B1 | 5/2003 |
| EP | 1348408 A2 | 10/2003 |
| EP | 1245204 A3 | 1/2004 |
| EP | 1380273 A2 | 1/2004 |
| EP | 1449500 A2 | 8/2004 |
| EP | 1550419 A2 | 7/2005 |
| FR | 2 521 421 | 11/1975 |
| FR | 2445136 A1 | 7/1980 |
| FR | 2521421 A1 | 8/1983 |
| FR | 2589720 A1 | 5/1987 |
| FR | 2594323 A1 | 8/1987 |
| FR | 2630639 A1 | 11/1989 |
| FR | 2 682 589 | 4/1993 |
| FR | 2682287 A1 | 4/1993 |
| FR | 2682589 A1 | 4/1993 |
| FR | 2 718 953 | 10/1995 |
| FR | 2740325 A1 | 4/1997 |
| FR | 2748389 A1 | 11/1997 |
| FR | 2768329 A1 | 3/1999 |
| FR | 2833479 A1 | 6/2003 |
| GB | 2 007 980 A | 5/1979 |
| GB | 2007980 A | 5/1979 |
| GB | 2215610 A | 9/1989 |
| GB | 2355935 A | 5/2001 |
| GB | 2405347 B | 8/2006 |
| JP | 58-203749 A1 | 11/1983 |
| JP | 8-506042 T | 7/1996 |
| JP | 2002524138 T | 8/2002 |
| WO | WO 87/02882 | 5/1987 |
| WO | WO 89/09578 A1 | 10/1989 |
| WO | WO 89/11837 | 12/1989 |
| WO | WO 91/06260 | 5/1991 |
| WO | WO91/06260 A1 | 5/1991 |
| WO | WO-9409723 A1 | 5/1994 |
| WO | WO-9514446 A1 | 6/1995 |
| WO | WO-9725006 A1 | 7/1997 |
| WO | WO-9802116 A1 | 1/1998 |
| WO | WO 98/04202 | 2/1998 |
| WO | WO-9820818 A1 | 5/1998 |

(56) References Cited

FOREIGN PATENT DOCUMENTS

| | | | |
|---|---|---|---|
| WO | WO-9913803 A2 | 3/1999 |
| WO | WO-9932053 A1 | 7/1999 |
| WO | WO-0023010 A1 | 4/2000 |
| WO | WO-0023011 A1 | 4/2000 |
| WO | WO-0106961 A1 | 2/2001 |
| WO | WO 01/28457 A1 | 4/2001 |
| WO | WO-0134069 A1 | 5/2001 |
| WO | WO 01/66021 A1 | 9/2001 |
| WO | WO 01/66022 A1 | 9/2001 |
| WO | WO 01/70142 A1 | 9/2001 |
| WO | WO 03/051210 A2 | 6/2003 |
| WO | WO 03/051211 A1 | 6/2003 |
| WO | WO-03068119 A2 | 8/2003 |
| WO | WO-03070127 A1 | 8/2003 |
| WO | WO 03/099159 A2 | 12/2003 |
| WO | WO 2004/002332 A1 | 1/2004 |
| WO | WO-2004037119 A2 | 5/2004 |
| WO | WO2004/058108 A1 | 7/2004 |
| WO | WO-2005067521 A2 | 7/2005 |
| WO | WO2005/069809 A2 | 8/2005 |
| WO | WO2005/069809 A3 | 8/2005 |

OTHER PUBLICATIONS

The extended Search Report dated Feb. 12, 2010 from related European application No. 06733764.2.
The Office Action mailed Jan. 12, 2009 in related British application No. GB0710667.7.
The Response filed May 12, 2009 to the Office Action mailed Jan. 12, 2009 in related British application No. GB0710667.7.
The International Preliminary Report on Patentability mailed Aug. 2, 2007 in related International application No. PCT/US2006/000875.
The International Preliminary Report on Patentability mailed Jan. 21, 2005 in related International application No. PCT/US2006/001026.
Office Action mailed Oct. 5, 2009 in U.S. Appl. No. 11/083,890.
Amendment in response to Office Action filed Feb. 4, 2010 in U.S. Appl. No. 11/083,890.
Office Action mailed Feb. 8, 2011 in related Japanese Application No. 2007-552278 and its English translation.
Partial European Search Report mailed Mar. 28, 2011 in related European Application No. EP03734180.7.
Office Action mailed Mar. 23, 2011 in European Application No. EP03713503.5.
Extended search report mailed Dec. 17, 2010 in European Application No. EP10179328.9.
The Office Action mailed Apr. 15, 2011 in related European Patent Application No. 03729131.7.
U.S. Appl. No. 10/444,927, Examiner Interview Summary mailed Apr. 16, 2008, 2 pgs.
U.S. Appl. No. 10/444,927, Final Office Action mailed Jul. 14, 2006, 7 pgs.
U.S. Appl. No. 10/444,927, Final Office Action mailed Dec. 31, 2007, 8 pgs.
U.S. Appl. No. 10/444,927, Non Final Office Action mailed Jan. 6, 2006, 7 pgs.
U.S. Appl. No. 10/444,927, Non Final Office Action mailed Mar. 26, 2007, 7 pgs.
U.S. Appl. No. 10/444,927, Non Final Office Action mailed Dec. 23, 2008, 8 pgs.
U.S. Appl. No. 10/444,927, Notice of Allowance mailed Jun. 26, 2009, 6 pgs.
U.S. Appl. No. 10/444,927, Notice of Appeal filed Jun. 30, 2008, 4 pgs.
U.S. Appl. No. 10/444,927, Pre-Appeal Brief Request filed May 22, 2009, 5 pgs.
U.S. Appl. No. 10/444,927, Preliminary Amendment filed Aug. 6, 2003, 12 pgs.
U.S. Appl. No. 10/444,927, Response filed Apr. 20, 2006 to Non Final Office Action mailed Jan. 6, 2006, 13 pgs.
U.S. Appl. No. 10/444,927, Response filed Sep. 26, 2007 to Non Final Office Action mailed Mar. 26, 2007, 18 pgs.
U.S. Appl. No. 10/444,927, Response filed Sep. 30, 2008 to Final Office Action mailed Dec. 31, 2007, 13 pgs.
U.S. Appl. No. 10/444,927, Response filed Oct. 6, 2005 to Restriction Requirement mailed Sep. 6, 2005, 11 pgs.
U.S. Appl. No. 10/444,927, Response filed Dec. 13, 2006 to Final Office Action mailed Jul. 14, 2006, 16 pgs.
U.S. Appl. No. 10/444,927, Restriction Requirement mailed Sep. 6, 2005, 5 pgs.
U.S. Appl. No. 10/445,288, Final Office Action mailed Jun. 8, 2005, 8 pgs.
U.S. Appl. No. 10/445,288, Final Office Action mailed Jul. 21. 2006, 11 pgs.
U.S. Appl. No. 10/445,288, Non Final Office Action mailed Oct. 29, 2004, 10 pgs.
U.S. Appl. No. 10/445,288, Non Final Office Action mailed Dec. 6, 2005, 9 pgs.
U.S. Appl. No. 10/445,288, Notice of Allowance mailed Aug. 31, 2006, 6 pgs.
U.S. Appl. No. 10/445,288, Response filed Mar. 29, 2005 to Non Final Office Action mailed Oct. 29, 2004, 32 pgs.
U.S. Appl. No. 10/445,288, Response filed May 5, 2006 to Non Final Office Action mailed Dec. 6, 2005, 14 pgs.
U.S. Appl. No. 10/445,288, Response filed Aug. 21, 2006 to Final Office Action mailed Jul. 21, 2006, 5 pgs.
U.S. Appl. No. 10/445,288, Response filed Nov. 8, 2005 to Final Office Action mailed Jun. 8, 2005, 12 pgs.
U.S. Appl. No. 10/749,346, Advisory Action mailed Jul. 11, 2007, 3 pgs.
U.S. Appl. No. 10/749,346, Advisory Action mailed Dec. 12, 2008, 3 pgs.
U.S. Appl. No. 10/749,346, Final Office Action mailed Apr. 12, 2006, 6 pgs.
U.S. Appl. No. 10/749,346, Final Office Action mailed Apr. 16, 2007, 5 pgs.
U.S. Appl. No. 10/749,346, Final Office Action mailed Aug. 13, 2008, 8 pgs.
U.S. Appl. No. 10/749,346, Non Final Office Action mailed Oct. 20, 2006, 7 pgs.
U.S. Appl. No. 10/749,346, Non Final Office Action mailed Nov. 3, 2005, 8 pgs.
U.S. Appl. No. 10/749,346, Non Final Office Action mailed Dec. 10, 2007, 8 pgs.
U.S. Appl. No. 10/749,346, Notice of Allowance mailed Apr. 16, 2009, 5 pgs.
U.S. Appl. No. 10/749,346, Notice of Allowance mailed Jun. 16, 2010, 3 pgs.
U.S. Appl. No. 10/749,346, Response filed Jan. 13, 2009 to Advisory Action mailed Dec. 12, 2008, 14 pgs.
U.S. Appl. No. 10/749,346, Response filed Jan. 23, 2007 to Non Final Office Action mailed Oct. 20, 2006, 15 pgs.
U.S. Appl. No. 10/749,346, Response filed Jan. 30, 2006 to Non Final Office Action mailed Nov. 3, 2005, 21 pgs.
U.S. Appl. No. 10/749,346, Response filed May 31, 2007 to Final Office Action mailed Apr. 16, 2007, 15 pgs.
U.S. Appl. No. 10/749,346, Response filed Jun. 5, 2008 to Non Final Office Action mailed Dec. 10, 2007, 16 pgs.
U.S. Appl. No. 10/749,346, Response filed Aug. 14, 2006 to Final Office Action mailed Apr. 12, 2006, 12 pgs.
U.S. Appl. No. 10/749,346, Response filed Aug. 26, 2005 to Restriction Requirement mailed Jul. 27, 2005, 11 pgs.
U.S. Appl. No. 10/749,346, Response filed Oct. 9, 2007 to Advisory Action mailed Jul. 11, 2007, 17 pgs.
U.S. Appl. No. 10/749,346, Response filed Nov. 25, 2008 to Final Office Action mailed Aug. 13, 2008, 13 pgs.
U.S. Appl. No. 10/749,346, Restriction Requirement mailed Jul. 27, 2005, 6 pgs.
U.S. Appl. No. 10/798,665, Final Office Action mailed Mar. 16, 2010, 7 pgs.
U.S. Appl. No. 10/798,665, Final Office Action mailed Apr. 17, 2008, 6 pgs.
U.S. Appl. No. 10/798,665, Non Final Office Action mailed Oct. 6, 2008, 8 pgs.

(56) References Cited

OTHER PUBLICATIONS

U.S. Appl. No. 10/798,665, Non Final Office Action mailed Oct. 9, 2007, 7 pgs.
U.S. Appl. No. 10/798,665, Notice of Allowance mailed Dec. 22, 2010, 7 pgs.
U.S. Appl. No. 10/798,665, Notice of Non-Compliant Amendment mailed Aug. 18, 2009, 3 pgs.
U.S. Appl. No. 10/798,665, Response filed Jan. 28, 2008 to Non Final Office Action mailed Oct. 9, 2007, 15 pgs.
U.S. Appl. No. 10/798,665, Response filed May 4, 2007 to Restriction Requirement mailed Apr. 4, 2007, 13 pgs.
U.S. Appl. No. 10/798,665, Response filed Jul. 16, 2010 to Final Office Action mailed Mar. 16, 2010, 12 pgs.
U.S. Appl. No. 10/798,665, Response filed Aug. 17, 2007 to Restriction Requirement mailed Jul. 16, 2007, 9 pgs.
U.S. Appl. No. 10/798,665, Response filed Sep. 4, 2009 to Notice of Non-Compliant Amendment mailed Aug. 18, 2009, 12 pgs.
U.S. Appl. No. 10/798,665, Response filed Sep. 12, 2008 to Final Office Action mailed Apr. 17, 2008, 17 pgs.
U.S. Appl. No. 10/798,665, Response filed Dec. 9, 2008 to Non Final Office Action mailed Oct. 6, 2008, 13 pgs.
U.S. Appl. No. 10/798,665, Restriction Requirement mailed Apr. 4, 2007, 5 pgs.
U.S. Appl. No. 10/798,665, Restriction Requirement mailed Jul. 16, 2007, 9 pgs.
U.S. Appl. No. 10/901,562, Final Office Action mailed Apr. 27, 2010, 6 pgs.
U.S. Appl. No. 10/901,562, Non Final Office Action mailed Jul. 6, 2009, 8 pgs.
U.S. Appl. No. 10/901,562, Notice of Allowance mailed Sep. 16, 2010, 7 pgs.
U.S. Appl. No. 10/901,562, Notice of Non-Compliant Amendment mailed Jun. 23, 2008, 4 pgs.
U.S. Appl. No. 10/901,562, Response filed Feb. 14, 2008 to Restriction Requirement mailed Jan. 24, 2008, 16 pgs.
U.S. Appl. No. 10/901,562, Response filed Feb. 23, 2009 to Restriction Requirement mailed Feb. 3, 2009, 9 pgs.
U.S. Appl. No. 10/901,562, Response filed Jun. 30, 2008 to Notice of Non-Compliant Amendment mailed Jun. 23, 2008, 15 pgs.
U.S. Appl. No. 10/901,562, Response filed Aug. 27, 2010 to Final Office Action mailed Apr. 27, 2010, 10 pgs.
U.S. Appl. No. 10/901,562, Response filed Aug. 31, 2007 to Restriction Requirement mailed Jul. 2, 2007, 17 pgs.
U.S. Appl. No. 10/901,562, Response filed Nov. 6, 2009 to Non Final Office Action mailed Jul. 6, 2009, 11 pgs.
U.S. Appl. No. 10/901,562, Response filed Nov. 10, 2008 to Official Action mailed Oct. 30, 2008, 15 pgs.
U.S. Appl. No. 10/901,562, Restriction Requirement mailed Jan. 24, 2008, 6 pgs.
U.S. Appl. No. 10/901,562, Restriction Requirement mailed Feb. 3, 2009, 7 pgs.
U.S. Appl. No. 10/901,562, Restriction Requirement mailed Jul. 2, 2007, 6 pgs.
U.S. Appl. No. 10/901,935, Final Office Action mailed Jul. 21, 2009, 7 pgs.
U.S. Appl. No. 10/901,935, Non Final Office Action mailed Mar. 16, 2010, 7 pgs.
U.S. Appl. No. 10/901,935, Non Final Office Action mailed Jul. 9, 2008, 8 pgs.
U.S. Appl. No. 10/901,935, Notice of Allowance mailed Oct. 4, 2010, 6 pgs.
U.S. Appl. No. 10/901,935, Response filed Feb. 14, 2008 to Restriction Requirement mailed Jan. 24, 2008, 20 pgs.
U.S. Appl. No. 10/901,935, Response filed Jul. 16, 2010 to Non Final Office Action mailed Mar. 16, 2010, 9 pgs.
U.S. Appl. No. 10/901,935, Response filed Aug. 31, 2007 to Restriction Requirement mailed Jul. 2, 2007, 22 pgs.
U.S. Appl. No. 10/901,935, Response filed Oct. 21, 2009 to Final Office Action mailed Jul. 21, 2009, 23 pgs.
U.S. Appl. No. 10/901,935, Response filed Nov. 10, 2008 to Non Final Office Action mailed Jul. 9, 2008, 30 pgs.
U.S. Appl. No. 10/901,935, Restriction Requirement mailed Jan. 24, 2008, 6 pgs.
U.S. Appl. No. 10/901,935, Restriction Requirement mailed Jul. 2, 2007, 6 pgs.
U.S. Appl. No. 10/901,941, Final Office Action mailed Jul. 21, 2009, 10 pgs.
U.S. Appl. No. 10/901,941, Final Office Action mailed Nov. 9, 2010, 9 pgs.
U.S. Appl. No. 10/901,941, Non Final Office Action mailed Mar. 16, 2010, 8 pgs.
U.S. Appl. No. 10/901,941, Non Final Office Action mailed Jul. 8, 2008, 8 pgs.
U.S. Appl. No. 10/901,941, Notice of Allowance mailed Apr. 2, 2012, 5 pgs.
U.S. Appl. No. 10/901,941, Response filed Feb. 14, 2008 to Restriction Requirement mailed Jan. 24, 2008, 21 pgs.
U.S. Appl. No. 10/901,941, Response filed Aug. 16, 2010 to Non Final Office Action mailed Jun. 16, 2010, 22 pgs.
U.S. Appl. No. 10/901,941, Response filed Aug. 31, 2007 to Restriction Requirement mailed Jul. 2, 2007, 21 pgs.
U.S. Appl. No. 10/901,941, Response filed Oct. 21, 2009 to Final Office Action mailed Jul. 21, 2009, 22 pgs.
U.S. Appl. No. 10/901,941, Response filed Nov. 10, 2008 to Non Final Office Action mailed Jul. 8, 2008, 27 pgs.
U.S. Appl. No. 10/901,941, Response filed Feb. 9, 2011 to Final Office Action mailed Nov. 9, 2010, 11 pgs.
U.S. Appl. No. 10/901,941, Restriction Requirement mailed Jan. 24, 2008, 6 pgs.
U.S. Appl. No. 10/901,941, Restriction Requirement mailed Jul. 2, 2007, 6 pgs.
U.S. Appl. No. 11/040,503, Final Office Action mailed Dec. 7, 2009, 10 pgs.
U.S. Appl. No. 11/040,503, Non Final Office Action mailed Feb. 27, 2009, 14 pgs.
U.S. Appl. No. 11/040,503, Non Final Office Action mailed May 26, 2011, 10 pgs.
U.S. Appl. No. 11/040,503, Non Final Office Action mailed Dec. 22, 2010, 11 pgs.
U.S. Appl. No. 11/040,503, Notice of Allowance mailed Dec. 21, 2011, 5 pgs.
U.S. Appl. No. 11/040,503, Response filed Mar. 22, 2011 to Non Final Office Action mailed Dec. 22, 2010, 11 pgs.
U.S. Appl. No. 11/040,503, Response filed May 7, 2010 to Final Office Action mailed Dec. 7, 2009, 9 pgs.
U.S. Appl. No. 11/040,503, Response filed Aug. 26, 2009 to Non Final Office Action mailed Feb. 27, 2009, 9 pgs.
U.S. Appl. No. 11/040,503, Response filed Aug. 29, 2011 to Non Final Office Action mailed May 26, 2011, 11 pgs.
U.S. Appl. No. 11/083,890, Notice of Allowance mailed Jun. 1, 2010, 4 pgs.
U.S. Appl. No. 11/083,890, Response filed Jun. 1, 2009 to Restriction Requirement mailed Apr. 1, 2009, 2 pgs.
U.S. Appl. No. 11/083,890, Restriction Requirement mailed Apr. 1, 2009, 8 pgs.
U.S. Appl. No. 11/219,098, Non Final Office Action mailed Dec. 27, 2007, 7 pgs.
U.S. Appl. No. 11/219,098, Notice of Allowance mailed Aug. 18, 2008, 8 pgs.
U.S. Appl. No. 11/219,098, Response filed May 20, 2008 to Non Final Office Action mailed Dec. 27, 2007, 8 pgs.
U.S. Appl. No. 11/219,098, Response filed Oct. 18, 2007 to Restriction Requirement mailed Sep. 28, 2007, 6 pgs.
U.S. Appl. No. 11/219,098, Restriction Requirement mailed Sep. 28, 2007, 6 pgs.
U.S. Appl. No. 12/567,530, Non Final Office Action mailed Jul. 19, 2012, 5 pgs.
U.S. Appl. No. 12/567,530, Notice of Allowance mailed Feb. 19, 2013, 5 pgs.
U.S. Appl. No. 12/567,530, Preliminary Amendment filed Dec. 7, 2009, 7 pgs.

(56) References Cited

OTHER PUBLICATIONS

U.S. Appl. No. 12/567,530, Response filed Oct. 19, 2012 to Non Final Office Action mailed Jul. 19, 2012, 11 pgs.
"Articular surface", [Online]. Retrieved from Internet: <http://www.drugs.com/dict/articular-surface.html>, (Mar. 18, 2011), 1 pg.
"Articular surface of patella", Stedman's Medical Dictionary, 27th edition, Lippincott Williams & Wilkins, (Copyright 2000), 2 pgs.
"Avon Patello-Femoral Arthroplasty", Howmedica Ostenonics, Surgical Technique, (Aug. 2003), 1-11.
Canadian Application Serial No. 2,484,552, Office Action mailed Feb. 24, 2010, 2 pgs.
Canadian Application Serial No. 2,490,673, Office Action mailed Apr. 9, 2009, 3 pgs.
Canadian Application Serial No. 2,490,673, Response filed Oct. 8, 2009 to the Office Action mailed Apr. 9, 2009, 8 pgs.
Canadian Patent Application No. 2640576, Office Action mailed Sep. 6, 2011, 2 pgs.
European Application Serial No. 06733764.2, Extended European Search Report mailed Feb. 12, 2010, 9 pgs.
European Application Serial No. 06733764.2, Office Action mailed Mar. 2, 2010, 1 pg.
European Application Serial No. 06733764.2, Office Action mailed Mar. 8, 2012, 3 pgs.
European Application Serial No. 06733764.2, Office Action mailed May 2, 2011, 3 pgs.
European Application Serial No. 06733764.2, Office Action mailed Jun. 9, 2010, 1 pg.
European Application Serial No. 06733764.2, Response filed Mar. 27, 2012 to Office Action mailed Mar. 8, 2012, 8 pgs.
European Application Serial No. 06733764.2, Response filed Apr. 15, 2010 to Office Action mailed Mar. 2, 2010, 1 pg.
European Application Serial No. 06733764.2, Response filed Aug. 23, 2011 to Office Action mailed May 2, 2011, 2 pgs.
European Application Serial No. 06733764.2, Response filed Oct. 19, 2010 to Office Action mailed Jun. 9, 2010, 9 pgs.
European Application Serial No. 08250441.6, European Search Report mailed May 5, 2008, 2 pgs.
European Application Serial No. 08250442.4, European Search Report mailed May 6, 2008, 2 pgs.
"Implants", (1990), 8 pgs.
International Application Serial No. PCT/US2003/016503, International Preliminary Examination Report mailed Jul. 10, 2004, 3 pgs.
International Application Serial No. PCT/US2003/016517, International Preliminary Examination Report mailed Jun. 21, 2004, 3 pgs.
International Application Serial No. PCT/US2006/000875, International Search Report mailed May 25, 2006, 2 pgs.
International Application Serial No. PCT/US2006/000875, Written Opinion mailed May 25, 2006, 3 pgs.
International Application Serial No. PCT/US2006/001026, International Search Report mailed Aug. 17, 2007, 1 pg.
International Application Serial No. PCT/US2006/001026, Written Opinion mailed Aug. 17, 2007, 5 pgs.
International Application Serial No. PCT/US2006/001973, International Preliminary Report on Patentability mailed Jul. 24, 2007, 4 pgs.
International Application Serial No. PCT/US2006/001973, International Search Report mailed Jun. 2, 2006, 2 pgs.
International Application Serial No. PCT/US2006/001973, Written Opinion mailed Jun. 2, 2006, 3 pgs.
"Johnson & Johnson LCS PFJ", Surgical Technique (At a Glance), [Online]. Retrieved from the internet: <http://www.jnjgateway.com/home.jhtm?page=viewContent&contentId=09008b988113bbel&loc=USENG>, (Accessed Nov. 13, 2006), 2 pgs.
"Knee Systems, Avon Femoral Component", Stryker Orthopaedics, Product Overview, [Online]. Retrieved from the Internet: <http://www.stryker.com/jointreplacements/sites/eiusavon/avon/femur.php>, (Accessed Nov. 13, 2006), 2 pgs.
"Link Knee Arthroplasty Implants", Product Brochure, [Online]. Retrieved from the Internet: <http://www.linkorthopaedics.com/main.html>, (Accessed Nov. 13, 2006), 1 pg.
"Natural-Knee II Patello-Femoral Joint System", Zimmer Surgical Technique, (2004), 1-17.
"Natural-Knee II Patello-Femoral Joint System", Zimmer Product Brochure, The Same Proven Design Elements as the Natural-Knee II Primary System, (2005), 2 pgs.
"P.F.C. Total Knee System", Johnson & Johnson Orthopaedics, (1988), 5 pgs.
"Patello-Femoral Prosthesis, Unicompartimental Prosthesis", 1st implantation: 1997; Ceraver Product Brochure, [Online]. Retrieved from the Internet: <http://www.ceraver.fr/femoropa TLRang.htm>, (Accessed Nov. 13, 2006), 1 pg.
"Patello-Femoral Replacement", Kinamed Inc, Product Brochure, [Online]. Retrieved from the Internet: <http://www .kinamed.com/kineMatchPFR.html>, (Accessed Nov. 13, 2006), 2 pgs.
"Whiteside Ortholoc Modular Knee System", Surgical Procedure for the Whiteside Ortholoc Modular Knee System, Dow Corning, Wright, (1990), 39 pgs.
"Whiteside Ortholoc Modular Knee System: Total Condylar", Dow Corning, (1989), 10 pgs.
Gerarld, Engh A, et al., "The AMK Total Knee System", Design Rationale and Surgical Procedure, (1988), 48 pgs.
Hofman, "The Intermedics Natural Knee System with Cancellous-Structured Titanium", (1987), 24 pgs.
Hofmann, Aaron A, "The Intermedics Natural-Knee System: Surgical Technique", Associate Professor of Surgery, Division of Orthopedic Surgery, University of Utah Medical Center, Salt Lake City, Utah; Intermedics Orthopedics, (1986), 24 pgs.
Miller, et al., "Unicompartmental Knee System", The Miller/Galante Advantage; Zimmer, 11 pgs.
Miller, et al., "Unicompartmental Knee System Implants and Instrumentation.", Zimmer, 6 pgs.
Rand, James A, "Patellar Resurfacing with Specialist Instruments in Total Knee Arthroplasty", Surgical Technique, Technique and Instruments Developed in Conjunction with James A. Rand, M.D., Mayo Clinic; Johnson & Johnson Orthopaedics, 11 pgs.
Richards, et al., "AGC Total Knee System; Patellar Femoral Systems", Biomet, Inc. Surgical Technique; Genesis Total Knee System Posterior-Stabilized, 13 pgs.
Richards, et al., "Genesis Total Knee System Posterior-Stabilized", Surgical Technique, Smith+Nephew, 60 pgs.

\* cited by examiner

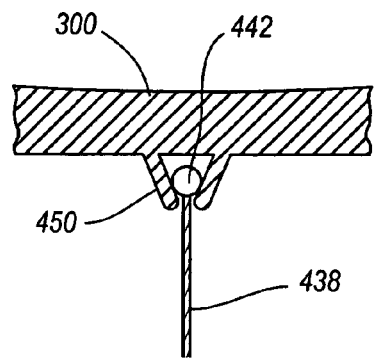 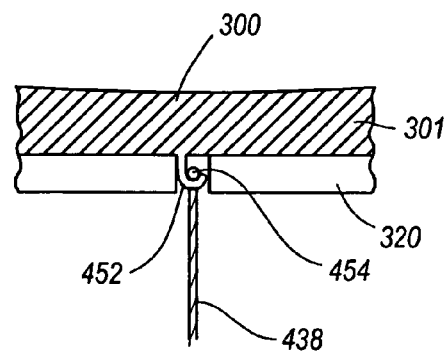
Fig. 9  Fig. 10
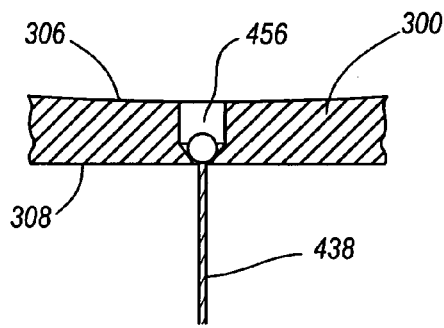 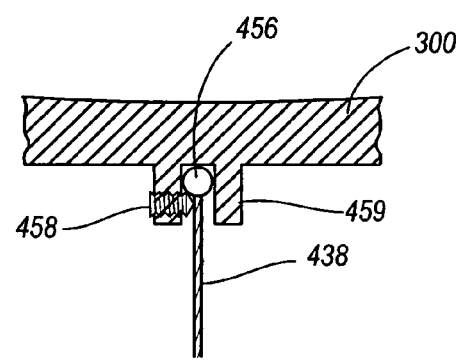
Fig. 11  Fig. 12
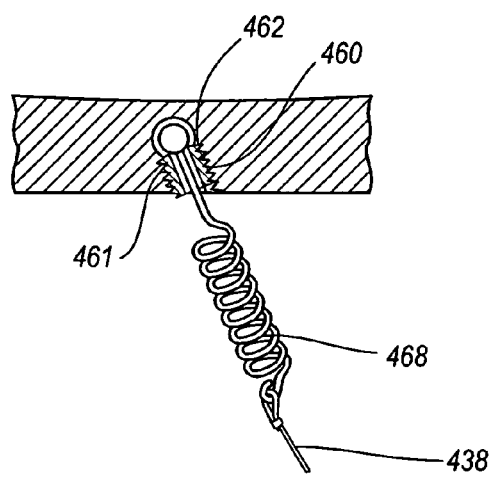
Fig. 13

GUIDE TEMPLATES FOR SURGICAL IMPLANTS AND RELATED METHODS

CROSS-REFERENCE TO RELATED APPLICATIONS

This application is a continuation-in-part of U.S. patent application Ser. No. 10/901,941, filed Jul. 28, 2004, which claims priority to U.S. Provisional Application Ser. No. 60/586,706, filed Jul. 9, 2004, which applications are incorporated herein by specific reference.

BACKGROUND OF THE INVENTION

1. The Field of the Invention

The present invention relates to instruments and methods for preparing an orthopedic joint articulation surface to receive a bearing implant.

2. The Relevant Technology

The human body has a variety of movable orthopedic joints such as the knee joint, hip joint, shoulder joint, and the like. These joints are formed by the intersection of two bones. The intersecting end of each bone has smooth articular surface that is comprised of cartilage. As a result of injury, wear, arthritis, disease or other causes, it is occasionally necessary to replace all or part of an orthopedic joint with an artificial implant. This procedure is referred to as a joint replacement or arthroplasty. For example, a total knee arthroplasty comprises cutting off or resecting the articular surfaces at both the distal end of the femur and the proximal end of the tibia. Complementary artificial implants are then mounted on the distal end of the femur and the proximal end of the tibia. Where only a portion of a joint is damaged, a partial joint arthroplasty can be performed. In this procedure, one or more artificial implants replace only a portion of a joint.

Although joint replacement is now a common procedure that has met with popular success, conventional implants and related mounting techniques have significant shortcomings. One significant drawback of many joint replacements is the extended and painful patient recovery. For example, a traditional knee replacement requires an open procedure wherein a relatively large incision is made which severs a portion of the muscle bounding the femur. The large incision is made so as to fully expose the respective ends of the femur and tibia.

This exposure is necessary when using conventional techniques to resect the femur and tibia and to mount the implants. For example, some conventional tibial implants are screwed directly into the resected end face of the tibia. Mounting such screws requires exposure of the resected end face. In yet other embodiments, the implants are formed with posts projecting therefrom. The posts are received within sockets formed on the resected end face of the tibia and femur. Again, forming of the sockets and inserting the posts into the sockets requires substantially full exposure of the resected end face of the tibia and femur.

In general, the more invasive the surgery, the more painful, difficult, and time consuming the patient recovery. This is largely due to the significant amount of scar tissue produced by the incision and resection of various soft tissues. Furthermore, such open and invasive surgeries have a greater risk of infection.

Another problem with conventional joint implants and related techniques for mounting is that it can be difficult to fit, adjust, and/or exchange different implants during the fitting stage. That is, implants come in a variety of different sizes, shapes, and configurations. During the joint replacement procedure, the surgeon may often test a variety of different sized implants to determine the best fit and alignment. As conventional implants are screwed into or pounded onto the bone during placement, the fitting, adjustment, and/or replacement of different conventional implants can be difficult and potentially damaging to the bone. Likewise, it can often be difficult to replace worn or damaged implants.

Accordingly, what is needed are implants and related methods and systems for preparing an articular surface of a joint and mounting an implant thereat which minimizes the length of incision, the amount of bone resection, and/or the impact on soft tissue. What is also needed are implants and related methods and systems which enable easier fitting, alignment, testing, and/or replacement of implants.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 9 is a cross sectional side view showing a wire attached to an implant by crimping;

FIG. 10 is a cross sectional side view showing a wire attached to an implant by looping around a hook;

FIG. 11 is a cross sectional side view showing a wire attached to an implant by passing through a constricted opening in the implant;

FIG. 12 is a cross sectional side view showing a wire attached to an implant by a set screw;

FIG. 13 is a cross sectional side view showing a wire attached to an implant by a barbed retainer;

DETAILED DESCRIPTION OF THE PREFERRED EMBODIMENTS

Figure 1:
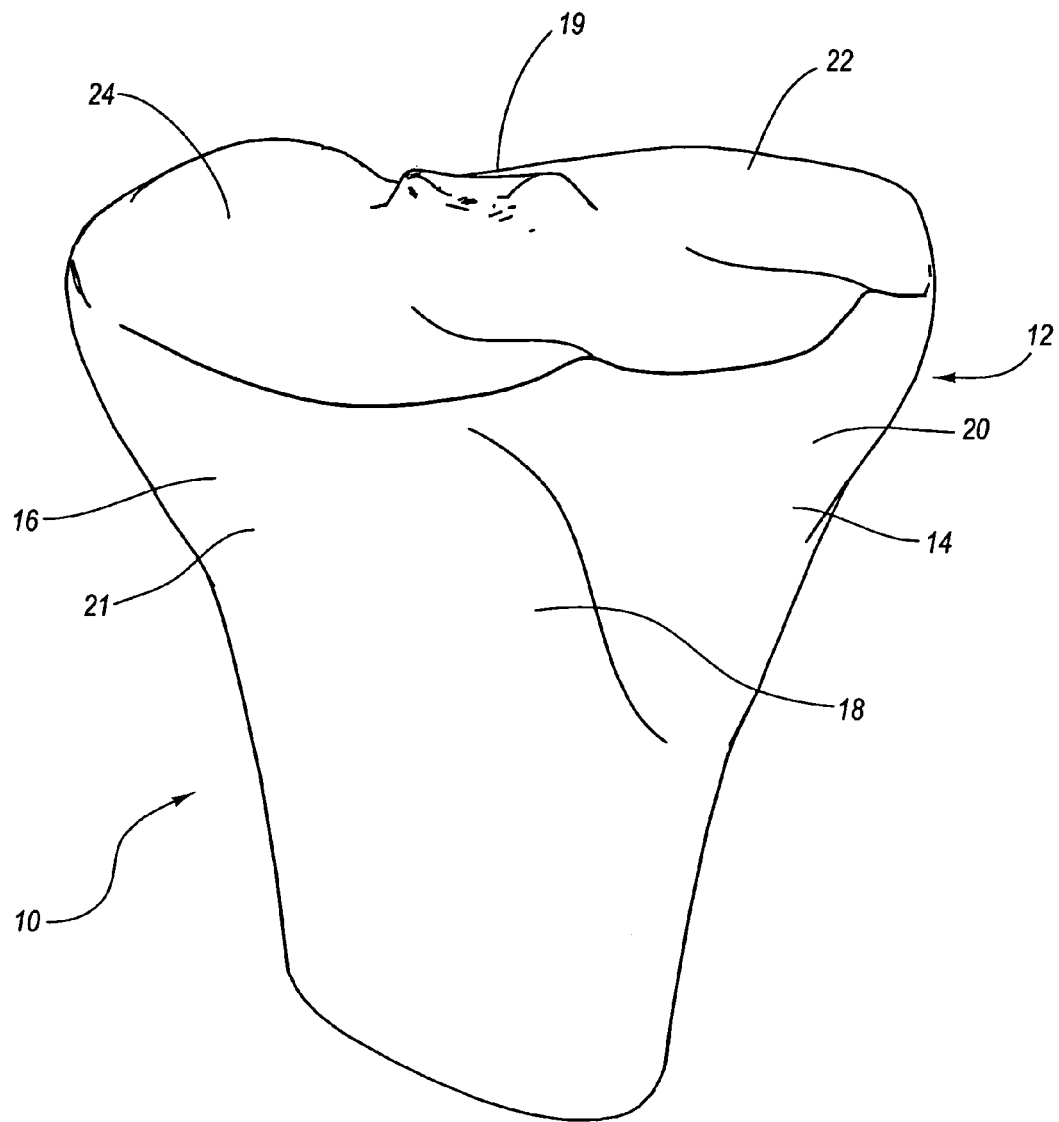
FIG. 1 is a perspective view of the proximal end of a tibia.

The present invention relates to methods and apparatus for preparing an articulation surface of an orthopedic joint to receive an implant, implants for mounting at an articulation surface of an orthopedic joint, anchoring systems for securing an implant at an articulation surface of an orthopedic joint, and related methods and instruments. As used in the specification and appended claims, the terms "articulation surface" and "natural articulation surface" are broadly intended to include all natural articular surfaces of a bone forming a portion of an orthopedic joint and all articulation wear surfaces of a bone forming a portion of an orthopedic joint which are produced as a result of ware, trauma, disease, or other causes which remove all or a portion of the natural articular surface.

The implants, anchoring systems, instruments, and methods of the present invention can be used in combination to mount an inventive implant or can be used separately or in combinations with other conventional implants, anchoring systems, instruments and/or methods. It is appreciated that the implants, anchoring systems, instruments, and methods of the present invention can be used for mounting an implant on virtually any articulation surface of any orthopedic joint in a human or other mammal. By way of example and not by limitation, the implants, anchoring systems, instruments, and methods of the present invention can be used in association with resurfacing an articulation surface of a knee joint, ankle joint, hip joint, shoulder joint, elbow joint, wrist joint, interphalangeal joint, or other joints. As such, the implants can be mounted on the proximal end and distal end of the femur, tibia, humerus, radius, and ulna, and on the articular surfaces of the scapula, pelvis, bones within the foot and hand, and other bone articular surfaces. Likewise, the implants, anchoring systems, instruments, and methods of the present invention can be used in facilitating a partial joint arthroplasty or a total joint arthroplasty.

In one embodiment, the implants, anchoring systems, instruments, and/or methods of the present invention are designed so that an articulation surface of a joint can be prepared and an implant mounted thereon using procedures that are minimally invasive. As a result, recovery time is significantly improved while the damage to soft tissue if decreased and the risk of infection minimized. Also in one embodiment of the present invention, the implants, anchoring systems, instruments, and/or methods are designed so that the implant can be selectively adjusted, tightened, and/or loosened after the implant is positioned on the articulation surface. This ability allows for greater ease in adjustment and fitting of an implant at the time of initial placement and for greater easy in replacement of an implant.

Set forth below are several embodiments of the present invention used in association with preparing an articulation surface at a proximal end of a tibia and mounting a condylar implant at the proximal end of the tibia. It is again noted that these embodiments are only given by way of example and that one skilled in the art based on the teaching provided herein would be able to use corresponding implants, methods, and instruments to prepare and/or mount an implant on other joint articulation surfaces.

Depicted in FIG. 1 is a proximal end 10 of a tibia 12. Proximal end 10 has a lateral side 14 and a medial side 16 which each extend between an anterior side 18 and a posterior side 19. Proximal end 10 further comprises a lateral condyle 20 and a medial condyle 21. Lateral condyle 20 terminates proximally at a lateral facet 22 of a superior articular surface of tibia 12 while medial condyle 21 terminates proximally at medial facet 24 of a superior articular surface of tibia 12.

Although tibia 12 shown in FIG. 1 is from a left leg, it is appreciated that the tibia of the right leg has a complimentary configuration and that the methods and apparatus of this specific example are equally applicable thereto. Furthermore, the methods and apparatus of this example are primarily illustrated in association with medial condyle 21 of tibia 12. It is also appreciated that the methods and apparatus can be used in association with lateral condyle 20.

In one embodiment, to facilitate mounting of a condylar implant on medial condyle 21, conventional arthroscopic procedures are used to resect the posterior portion of the medial meniscus. Once the posterior portion of the medial meniscus is removed, a vertical or horizontal incision, generally in a range between about 2 cm to about 6 cm, is formed over the anterior side of the medial meniscus. Following retraction of the surrounding tissue, the anterior side of the medial meniscus is resected. A coarse rasp is then inserted between the medial condyle of the femur and medial condyle 21 of tibia 12. The rasp is used to remove approximately 1-2 mm of articular cartilage on medial facet 24 of tibia 12. Removal of the meniscus and the articular cartilage provides increased access to medial facet 24 of tibia 12.

Figure 2:
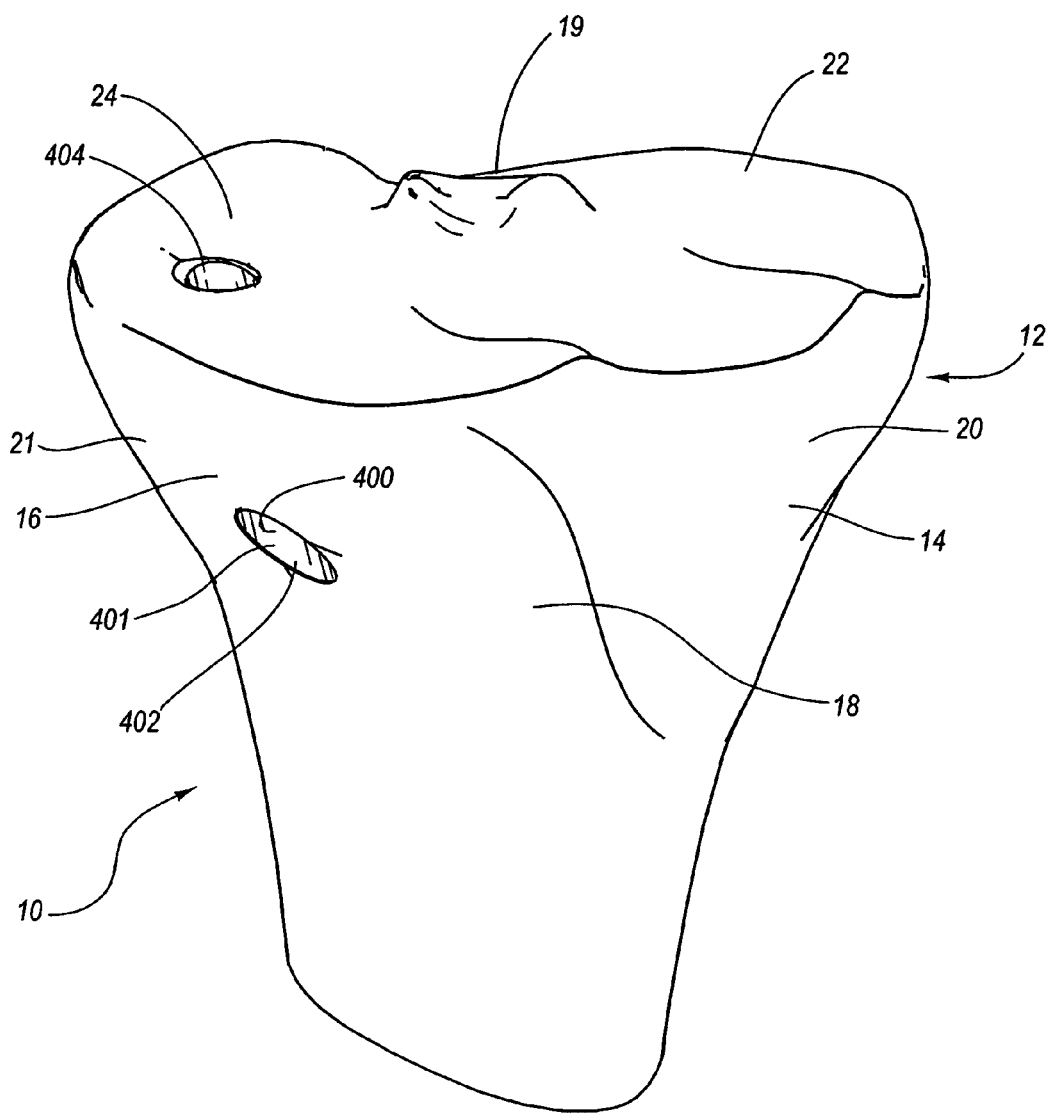
FIG. 2 is a perspective view of the tibia shown in FIG. 1 having a tunnel formed thereon.

Depicted in FIG. 2, a tunnel 400 is formed through a portion of tibia 12. Tunnel 400 can be used for preparing tibia 12 for a condylar implant and/or securing a condylar implant to tibia 12. Tunnel 400 has an interior surface 401 that extends from a first end 402 to an opposing end second end 404. First end 402 is formed on medial side 16 of proximal end 10 of tibia 12. Second end 404 is formed on medial facet 24 of tibia 12. Expressed in other terms, second end 404 of tunnel 400 is formed on a section of an articulation surface, i.e., medial facet 24, while first end 402 is at a location on tibia 12 that is spaced apart from the articulation surface. Although tunnel 400 can be any desired size, in one embodiment tunnel 400 has a diameter in a range between about 5 mm to about 10 mm. In alternative embodiments, it is appreciated that first end 402 of tunnel 400 can be positioned at any desired location at proximal end 10 of tibia 12. For example, first end 402 can be positioned at lateral side 14 or anterior side 18.

Tunnel 400 is typically formed using a drill in combination with one of a variety of different types of guide assemblies. Alternative methods and techniques for forming tunnel 400 are disclosed in U.S. patent application Ser. No. 10/901,941, filed Jul. 28, 2004 which is incorporated herein by specific reference (hereinafter "the '941 application").

Using the above-referenced methods and instruments, tunnel 400 can be formed by procedures that are minimally invasive to the patient. Once tunnel 400 is formed, tunnel 400 can then be used to assist in the resection of medial fact 24 and/or the mounting of a condylar implant on the resected medial facet 24. Furthermore, by using tunnel 400 the resection of medial facet 24 and the mounting of the condylar implant can also be performed using procedures that are minimally invasive.

Figure 3:
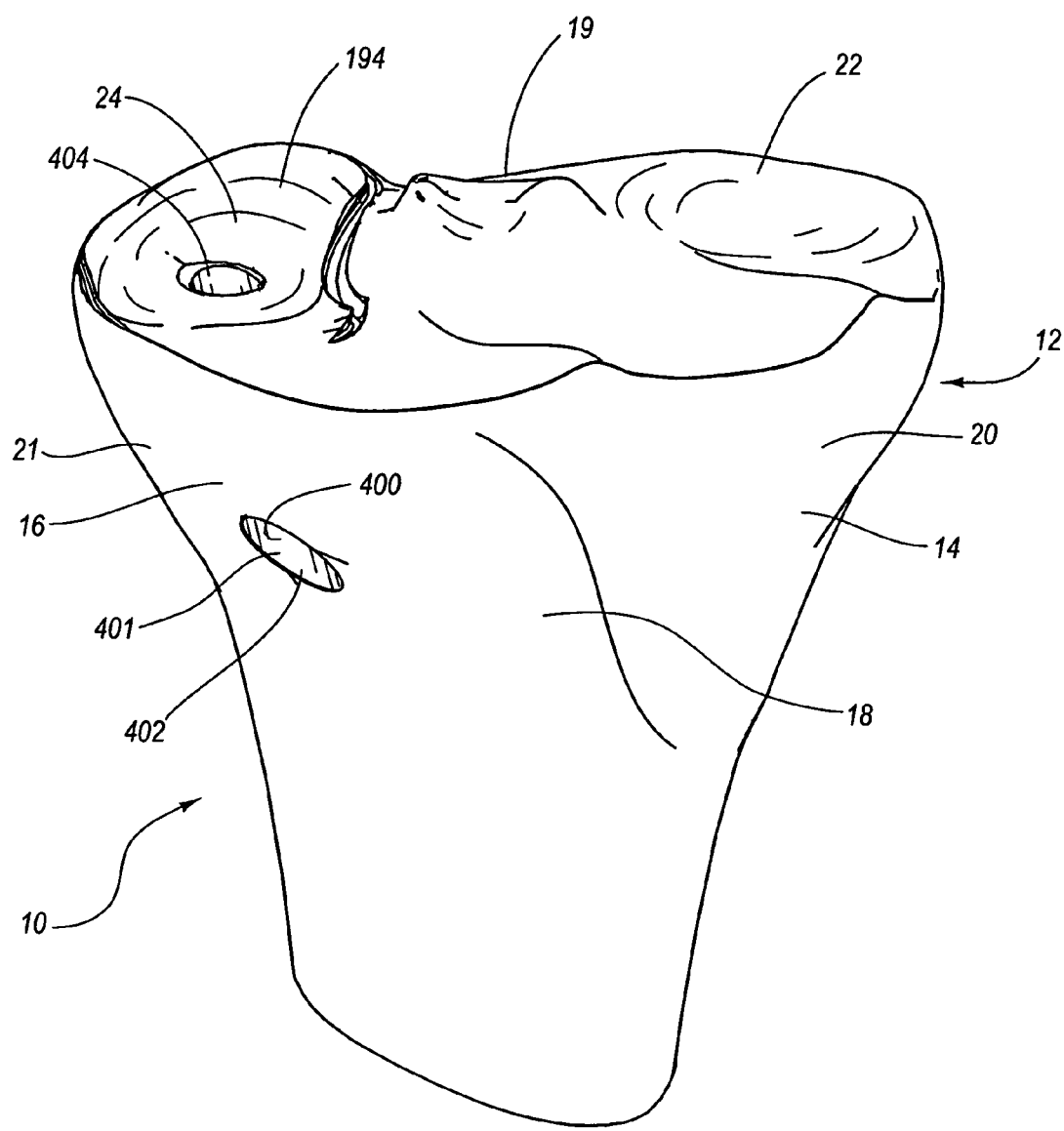
FIG. 3 is a perspective view of the tibia shown in FIG. 4 having a recessed pocket formed thereon.

Depicted in FIG. 3, a recessed pocket 194 is formed on medial facet 24. Pocket 194 is formed so as to intersect with second end 404 of tunnel 400 and is contoured to receive a condylar implant. It is appreciated that pocket 194 can be formed using a variety of different methods and instruments including templates, guides, mills, rasps and combinations thereof. In one embodiment, tunnel 400 can be used in the formation of pocket 194. In alternative embodiments, pocket 194 can be formed independent of tunnel 400. For example, depicted in FIG. 4 tibia 12 has been prepared to receive a condylar implant by first resecting medial condyle 21 so as to form a flat resected surface 234. Next, recessed pocket 194 is formed on resected surface 234 using a rasp or other instrument. Finally, tunnel 400 is formed extending from lateral side 14 of tibia 12 to pocket 194. In this latter approach, it is appreciated that pocket 194 can first be formed followed by the formation of tunnel 400. Examples of different methods and instructions that can be used in the formation of resected surface 234 and pocket 194 are disclosed in the '941 application.

As will be discussed below in greater detail, a bone anchor is secured within first end 402 of tunnel 400. The bone anchor requires a larger opening than what is necessarily needed for a line or fastener to pass through tunnel 400. Accordingly, where tunnel 400 is minimized to limit bone removal, first end 402 of tunnel 400 can be counter bored with a larger drill so as to enable proper placement of the bone anchor. In one embodiment, tunnel 400 can be counter sunk so as to have a diameter in a range between about 4 mm to 8 mm. Again, other dimensions can also be used.

Figure 5A:
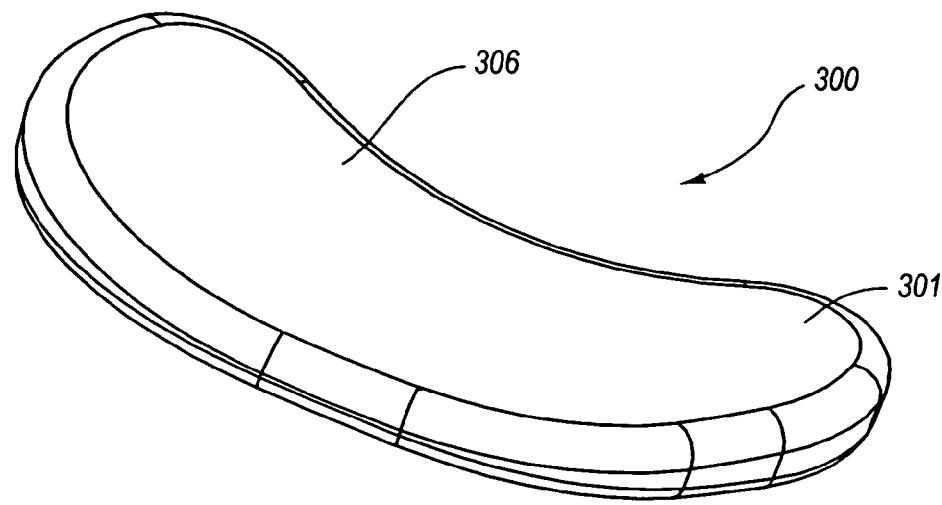
FIG. 5A is a top perspective view of a condylar implant.
Figure 5B:
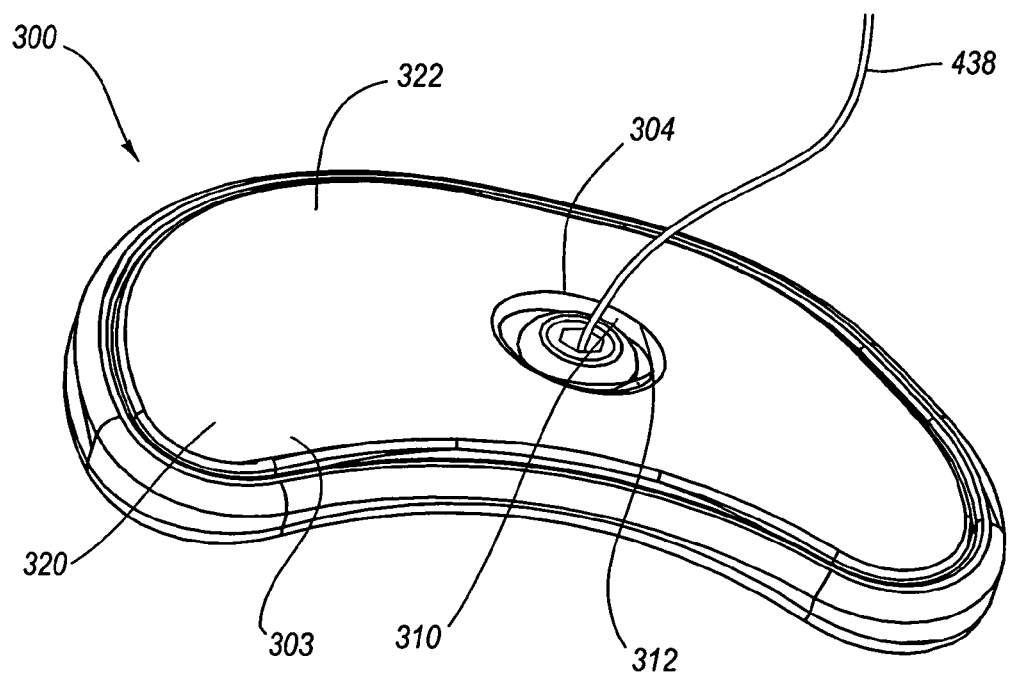
FIG. 5B is a bottom perspective view of the condylar implant shown in FIG. 5A.
Figure 5C:
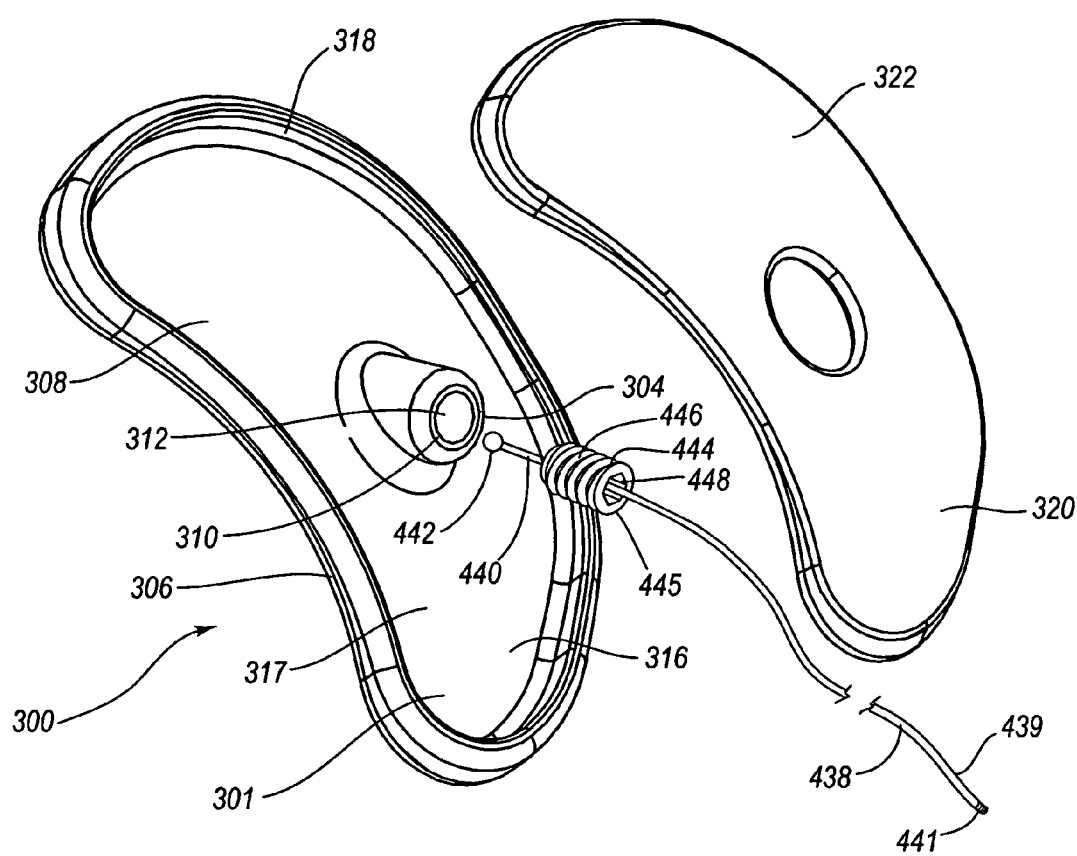
FIG. 5C is an exploded perspective view of the condylar implant shown in FIG. 5B.

Depicted in FIGS. 5A-C is one embodiment of a condylar implant 300 incorporating features of the present invention. The term "condylar implant" is broadly intended to include implants that can replace all or a portion of a condyle. The condylar implant can also replace all or a portion of the articulation surface of the condyle. Accordingly, while the depicted embodiments show one conventional size and configuration for a condylar implant, in alternative embodiments the condylar implant can be larger to replace more of the tibia or can be smaller to replace only a section of a condyle of a tibia. In such alternatives, the condylar implant can have a variety of different configurations.

Figure 4:
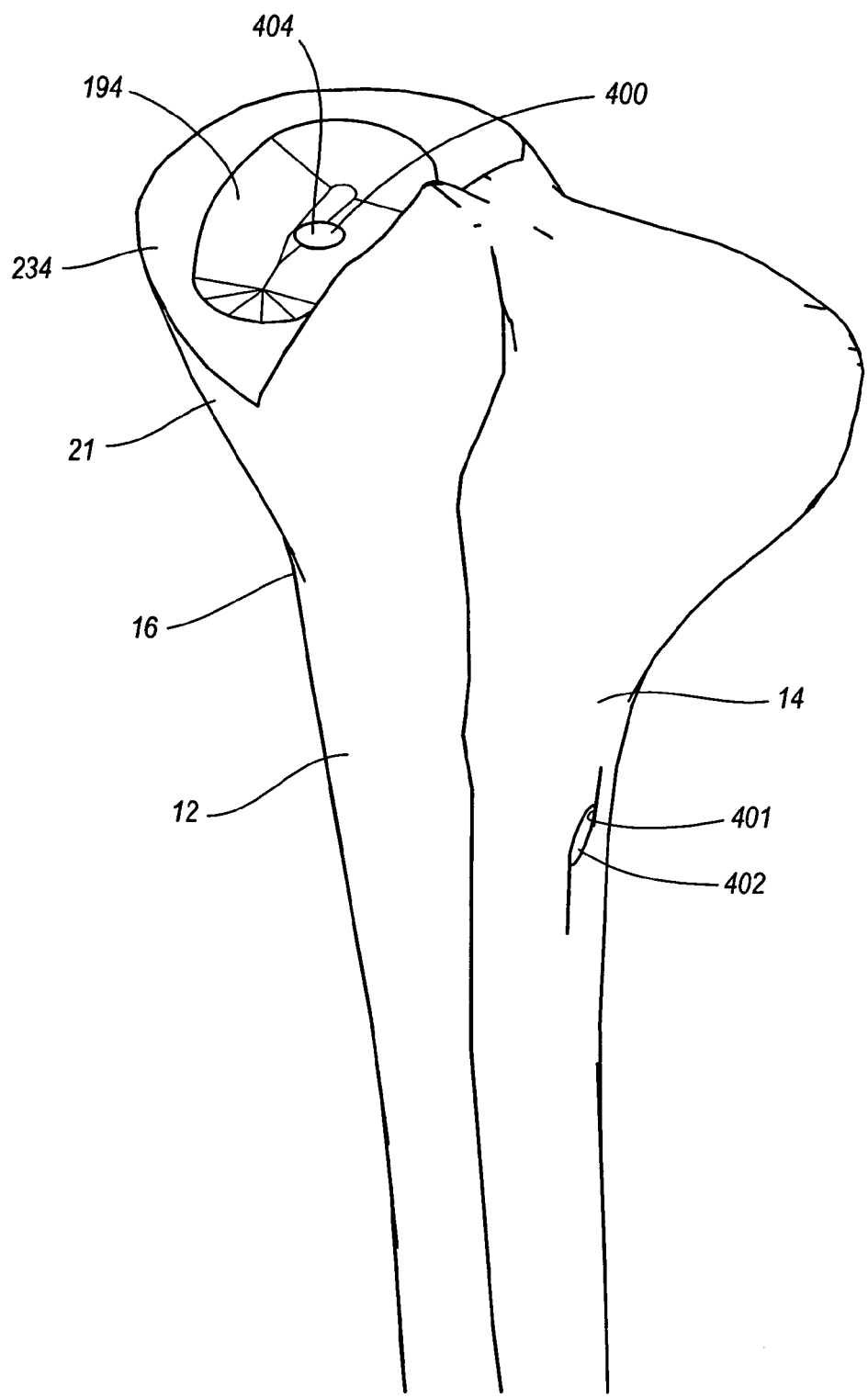
FIG. 4 is a perspective view of the tibia shown in FIG. 1 on which a flat resected surface has first been formed prior to forming the pocket thereon.

In general, condylar implant 300 has a top articular surface 306 and an opposing bone apposition surface 303. In one embodiment, top articular surface 306 has a generally concave contour that continuously curves front to back and side to side so as to mate with a corresponding femoral condyle. Alternatively, articular surface 306 can be substantially flat. Bone apposition surface 303 has a generally convex contour that continuously curves front to back and side to side and that is configured to mate with pocket 194 (FIGS. 3 and 4). In one embodiment, articular surface 306 is substantially complementary to bone apposition surface 303. As a result of contouring bone apposition surface 303, implant 300 can be formed having a low profile configuration with a generally uniform thickness along the length and width thereof. This uniform thickness provides uniform strength for implant 300. Furthermore, by contouring implant 300 to fit within pocket 194, the stability of mounted implant 300 is increased so as to prevent unwanted movement of implant relative to tibia 12.

In alternative embodiments, bone apposition surface 303 can be substantially flat. As a result, implant 300 can be mounted directly on flat resected surface 234. In this embodiment, however, contouring of articular surface 306 would result in the opposing ends of implant 300 being thicker than the middle. Again, however, depending on the size of the patient and the portion of the bone being replaced, implant 300 can have an array of different sizes and configurations.

As depicted in FIG. 5C, implant 300 comprises a body 301 and an inlay 320. Body 301 has top articular surface 306 and an opposing bottom surface 308. A pocket 316 is recess on bottom surface 308. Pocket 316 is bounded by a floor 317 and a sidewall 318 upstanding around the perimeter thereof. A stem 304 projects from floor 317 and is completely encircled by pocket 316. Body 301 is typically comprised of a metal such as chromium, cobalt, titanium, or the like and alloys thereof but can also be made of ceramics, plastics, or other materials. Body 301 can also be comprised of layers or sections of different materials. In one embodiment, body 301 has a maximum thickness typically in a range between about 2 mm to about 10 mm. Other dimensions can also be used depending on the amount that the tibial condyle is resected or worn away.

Inlay 320 is secured within pocket 316 of body 301 so as to encircle stem 304. Inlay 320 is comprised of a porous bone ingrowth material such as porous tantalum. Other conventional porous bone ingrowth materials can also be used. Inlay 320 is secured within pocket 316 using conventional techniques such as press fit, welding, adhesive, sintering, and the like. Inlay 320 can also be mechanically connected to body 301 such as by screws, fasteners, rivets, or the like. In alternative embodiments, pocket 316 can be eliminated and inlay 320 can be secured to the bottom surface of body 301 using various techniques. Inlay 320 has an exposed bottom surface 322 that, as discussed above, can be arched, substantially flat, or can have any other desired configuration. In this embodiment, bottom surface 322 of inlay 320 comprises substantially all of bone apposition surface 303 of base plate 301.

Figure 6A:
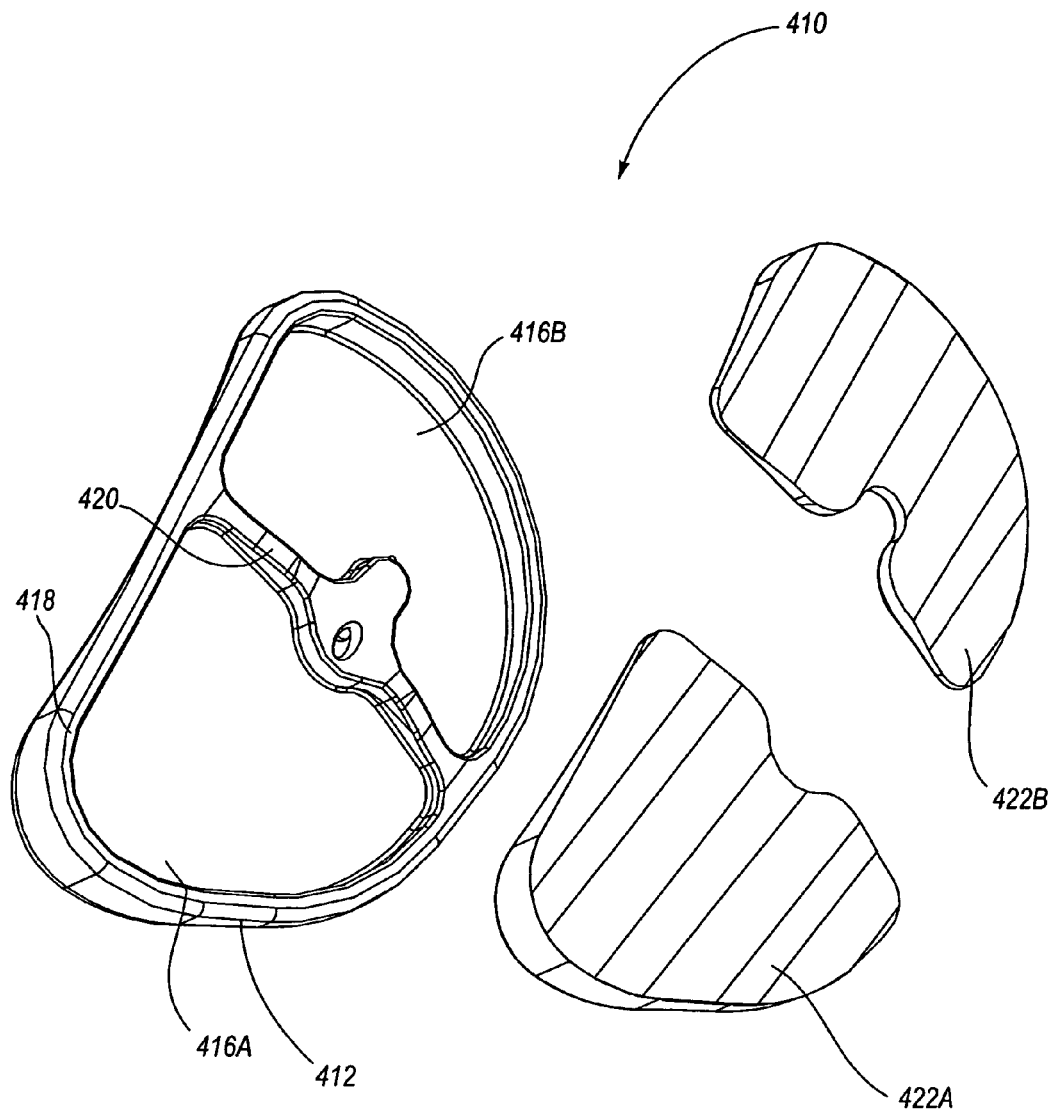
FIG. 6A is an exploded perspective view of an alternative embodiment of a condylar implant having two pockets.

In contrast to having a single pocket 316 in which a single inlay 320 is positioned, it is appreciated that body 301 can be formed having a plurality of pockets each adapted to receive a separate inlay. For example, depicted in FIGS. 6A and B is an alternative embodiment of an implant 410 comprising a body 412 having a bottom surface 414. Bottom surface 414 is formed with two pockets 416A and B which are partially bounded by a perimeter sidewall 418 and are separated by a central bridge 420. Each pocket 416A and B is adapted to receive a corresponding inlay 422A and B. In this embodiment, the bone apposition surface includes not only the bottom surface of inlays 422A and B but also the bottom surface of bridge 420 and perimeter sidewall 418.

Figure 7:
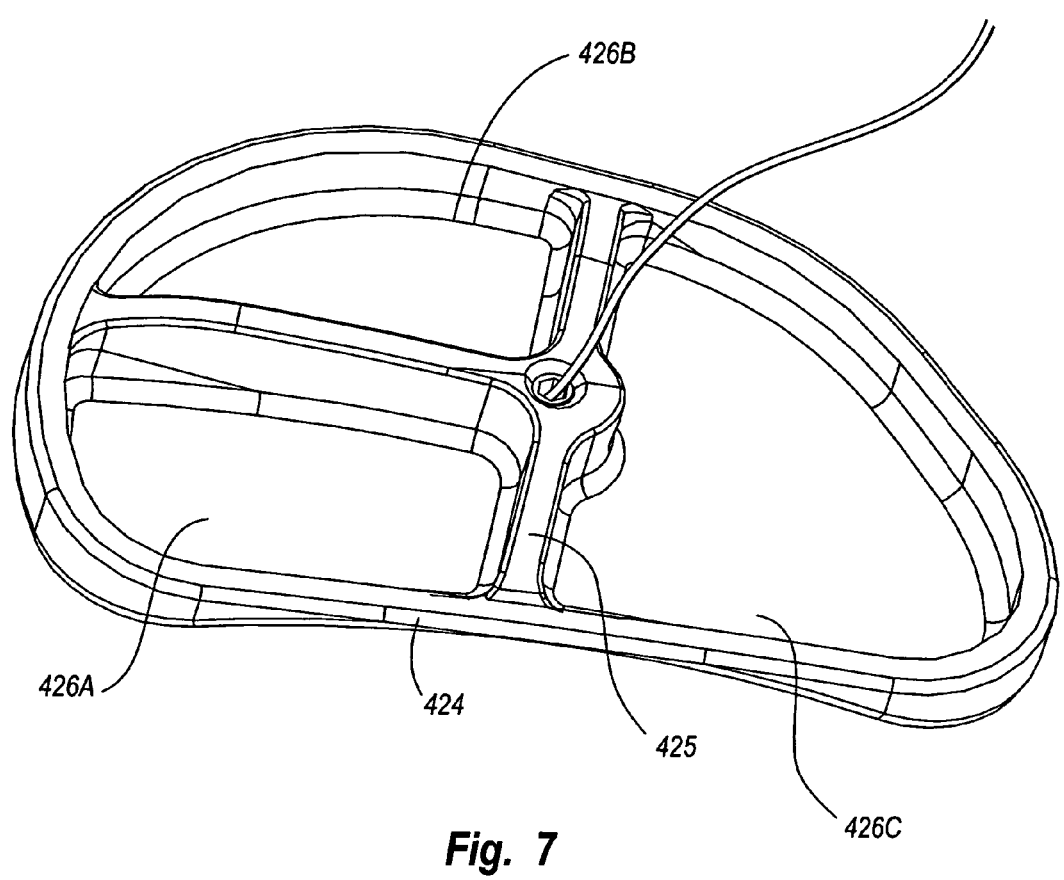
FIG. 7 is a bottom perspective view of another alternative embodiment of a condylar implant having three pockets.

Similarly, depicted in FIG. 7 is an alternative embodiment of a body 424 for an implant. Body has a bottom surface 424 with three separate pockets 426A, B, and C. Each of the pockets 426 is adapted to receive a separate inlay. The bridges formed between the separate pockets provide increased structural support for the implant and, as will be discussed below in greater detail, provide a structure on which a flexible line can be attached.

Figure 8:
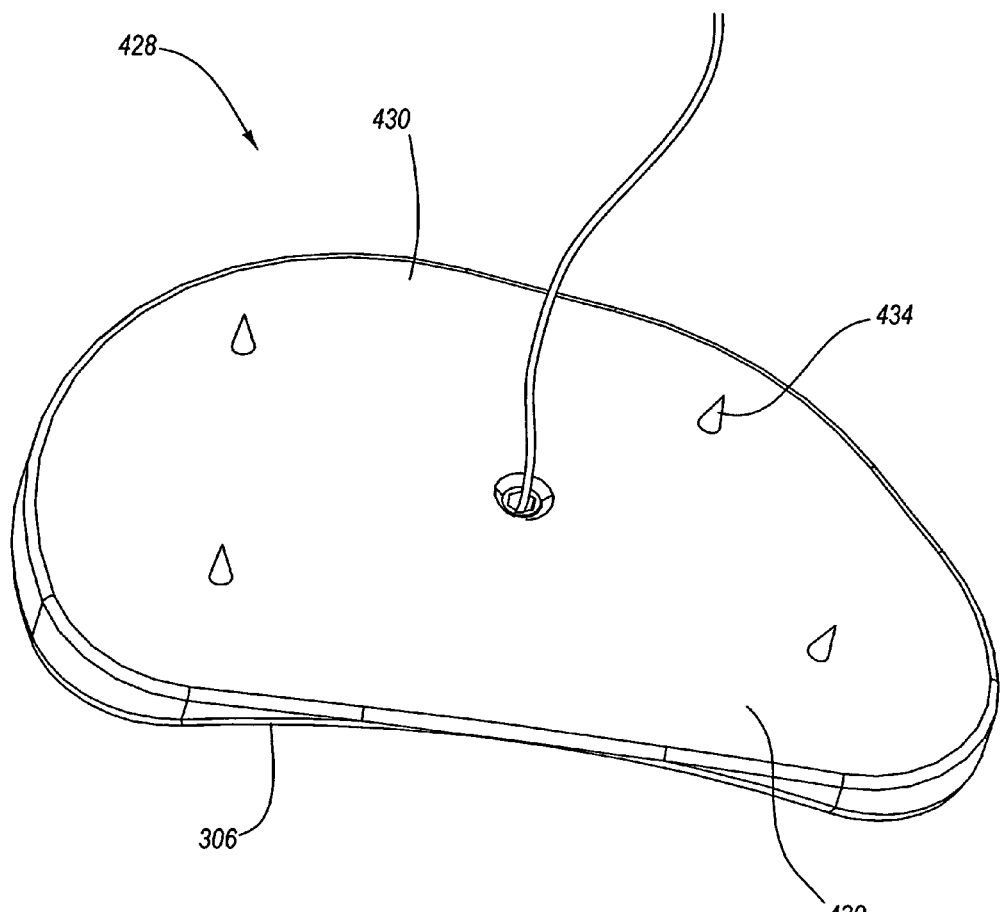
FIG. 8 is a perspective view of a unitary condylar implant having spikes formed thereon.

In still other embodiments, it is appreciated that the inlay of porous bone ingrowth material can be eliminated. In this embodiment, the condylar implant can comprise a single integral member. For example, depicted in FIG. 8 is an alternative embodiment of a condylar implant 428. Implant 428 is formed as a single integral body 430 having top articular surface 306 and an opposing bottom surface 430 which also functions as the bone apposition surface. To facilitate secure attachment of implant 428 to tibia 12, a plurality of spikes 434 are formed on bottom surface 430. It is appreciated that in all of the embodiments herein that spikes, fins, or other forms of projections can also be formed projecting from bottom surface of the implant. Such projections can be separated from or encircled by the porous bone ingrowth inlay. The projections can also be formed on the porous bone ingrowth inlay. Such projections can penetrate into the tibia or be received within slots formed on the tibia to help prevent unwanted movement of the implant.

In one embodiment, a flexible line is used to secure the implants to tibia 12. As used in the specification and append claims, the term "line" is broadly intended to include wire, cable, cord, suture, braded line, combinations thereof or any other type of flexible filament. The line can be made of metal, alloys, synthetics, composites, or any other desired material. In one embodiment of the present invention the line comprises braded filaments of a cobalt chrome alloy having a diameter in a range between about 0.25 mm to about 5 mm with about 0.5 mm to about 3 mm being more common and about 0.5 mm to about 2 mm being most common. Other dimensions can also be used. The line can be of any desired length.

In one embodiment, the line can also be defined in that for an unsupported length of line of 4 cm, the line has substantially no compressive strength. In yet other embodiments, for an unsupported length of line of 4 cm, the line fails under buckling when an axial compressive load of 0.25 Newtons (N), 1 N, 2 N, 5 N, 20 N, or 50 N is applied. That is, different lines can be used that fail under different loads. Stiffer lines can also be used.

It is also appreciated that the line can be static or resiliently stretchable. In one embodiment where the line is resiliently stretchable, the line can be comprised of a material have shape memory of pseudo elastic properties. One example of such a material is a nickel titanium alloy sold under the name Nitinol. In yet other embodiment, it is appreciated that sections of the line could be replaced with a spring member such as a coiled spring or rubber or bungee type member.

Returning to FIGS. 5B and C, an elongated line 438 is provided having a first end 439 and an opposing second end 440. First end 439 terminates at a tip 441 that is sealed so as to have and maintain a smooth uniformed diameter. Second end 440 terminates at an enlarged rounded head 442. In alternative embodiments, second end 440 can have the same configuration as first end 439 or can have an enlarged head of any desired configuration.

In one embodiment of the present invention, means are provided for connecting flexible line 438 to implant 300. By way of example and not by limitation, stem 304 is provided with a threaded socket 312. Slidably disposed on line 438 is a tubular retainer 444. Retainer 444 comprises a body 445 having one or more helical threads 446 mounted on the exterior surface thereof. Threads 446 are configured to engage with threaded socket 312. A channel 448 longitudinally extends through body 445. Channel 448 constricts toward the distal end of body 445 so that the channel 448 thereat is larger than the diameter of line 438 but smaller than the diameter of head 442. The proximal end of channel 448 is enlarged and has a polygonal transverse cross section. As a result, first end 439 of line 438 can be passed through channel 448 of body 445 distal to proximal. Line 438 can then be pulled through retainer 444 until head 442 is stopped by the constricted section of channel 448. The first end of line 438 can then be advanced through a central channel in a tubular driver (not shown) having a free end adapted to fit within channel 448 of retainer 444 at the proximal end thereof. The driver can thus be used to screw retainer 444 into threaded socket 312, thereby securing line 438 to implant 300.

Figure 6B:
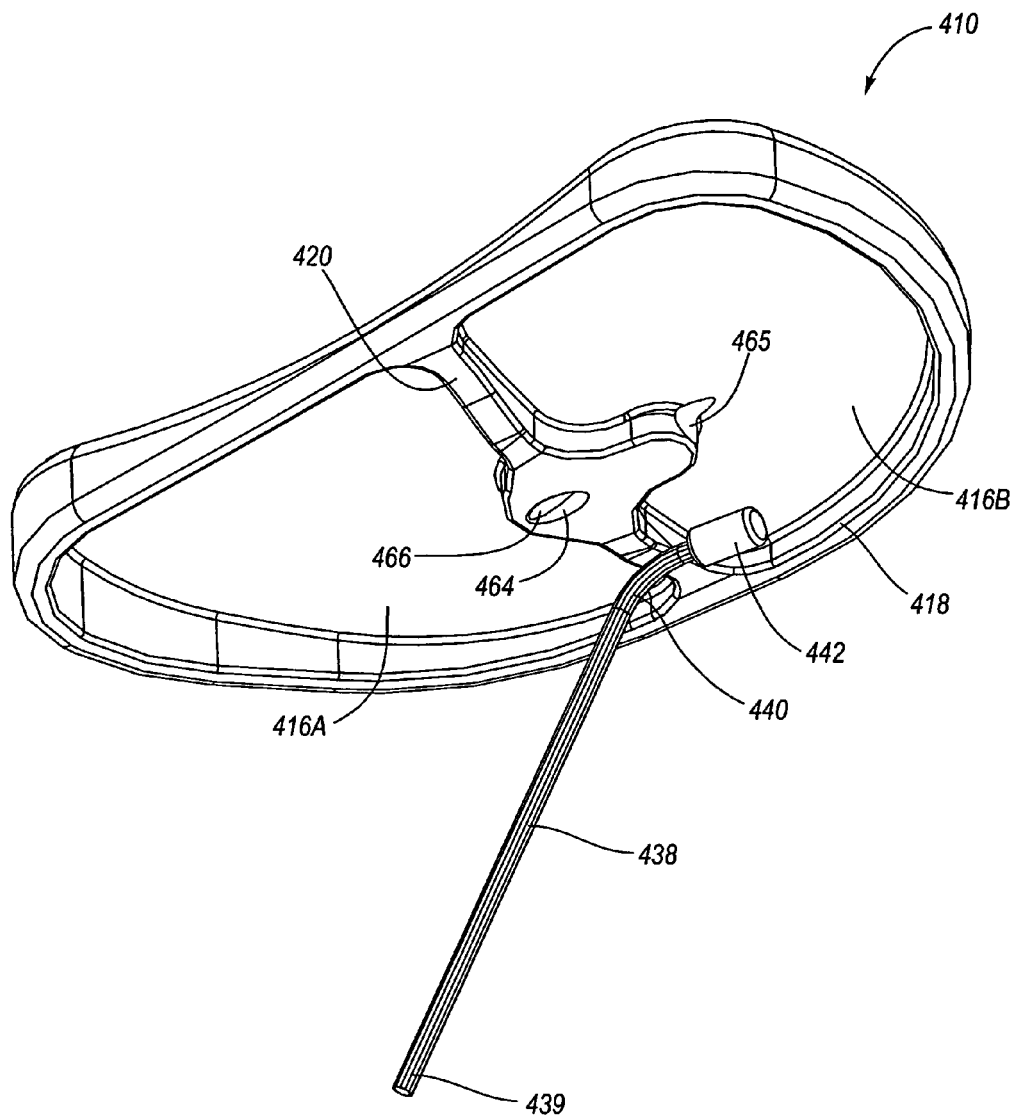
FIG. 6B is a bottom perspective view of the implant shown in FIG. 6A with a line for connecting thereto.

Depicted in FIG. 6B is another embodiment of the means for connecting a line to an implant. In this embodiment a passage 464 extends through bridge 420. Passage 464 has an entrance 465 formed on a side wall of bridge 420 and an exit 466 formed on a bottom surface of bridge 420. Again, passage 464 constricts as it extends from entrance 465 to exit 466. Line 438 is shown having an enlarged substantially cylindrical head 442 formed on second end 440. Head 442 is larger than the constricted portion of passage 464. Head 442 can be crimped, welded, or otherwise formed on line 438. Head 442 can also be integrally formed with line 438. During assembly, first end 439 of line 438 is passed through passage 464 from entrance 465 to exit 466. Line 438 is advanced through passage 464 until head 442 is captured and securely retained within constricted passage 464. Inlays 422A and B can then be positioned within pockets 416A and B. In yet other embodiments, rather than constricting passage 464, it is appreciated that head 442 can be wedge shaped so that head 442 is captured within passage 464.

Depicted in FIGS. 9-14 are a variety of still other embodiments of the means for connecting a line to an implant. Specifically, depicted in FIG. 9 is a stem 450 mounted to implant 300 which can be selectively crimped so as to catch head 442 within stem 450. In one embodiment this can be accomplished by forming slots along stem 450. Depicted in FIG. 10, a hook 452 is formed projecting from the bottom surface of body 301 of implant 300. In contrast to having head 442, a loop 454 is formed at the second end of line 438. Loop 454 is looped around hook 452. Inlay 320 is then mounted on the bottom surface of body 301 so as to prevent loop 454 from accidentally sliding off of hook 452.

Depicted in FIG. 11, a channel 456 can be formed extending through implant 300 from top surface 306 to bottom surface 308. Channel 456 is enlarged at top surface 306 so as to receive head 442 of line 438 but constricts toward bottom surface 308 so as to capture head 442 within channel 456. The opening to channel 456 on top surface 306 can be rounded to prevent unwanted wear on the femoral condyle. In other embodiments, a plug can be inserted within channel 456 so as to occlude the opening to channel 456. In still another alternative, instead of forming the opening to channel 456 top surface 306, a constricted slot can be formed that inwardly extends from the side of implant 300.

Depicted in FIG. 12, a set screw 458 is screwed into the side of a tubular stem 459 to capture head 456 therein. Finally, depicted in FIG. 13, rather than having a threaded retainer 444 as discussed above, a tubular retainer 460 can be provided with outwardly projecting barbs 461. Retainer 460 can simply be pushed into a socket 462 having threads or barbs thereon so that retainer 460 is captured therein. It is also noted that in FIG. 13 line 438 is shown comprising a resiliently stretchable spring 468. It is appreciated the spring 468 can be directly connected to the implant or disposed along line 438. Spring 468 can also come a variety of different shapes and sizes and be made from different materials. As will be discussed below in greater detail, spring 468 helps maintain the desired tension force on line 438 so that the implant is securely held in position.

Figure 14:
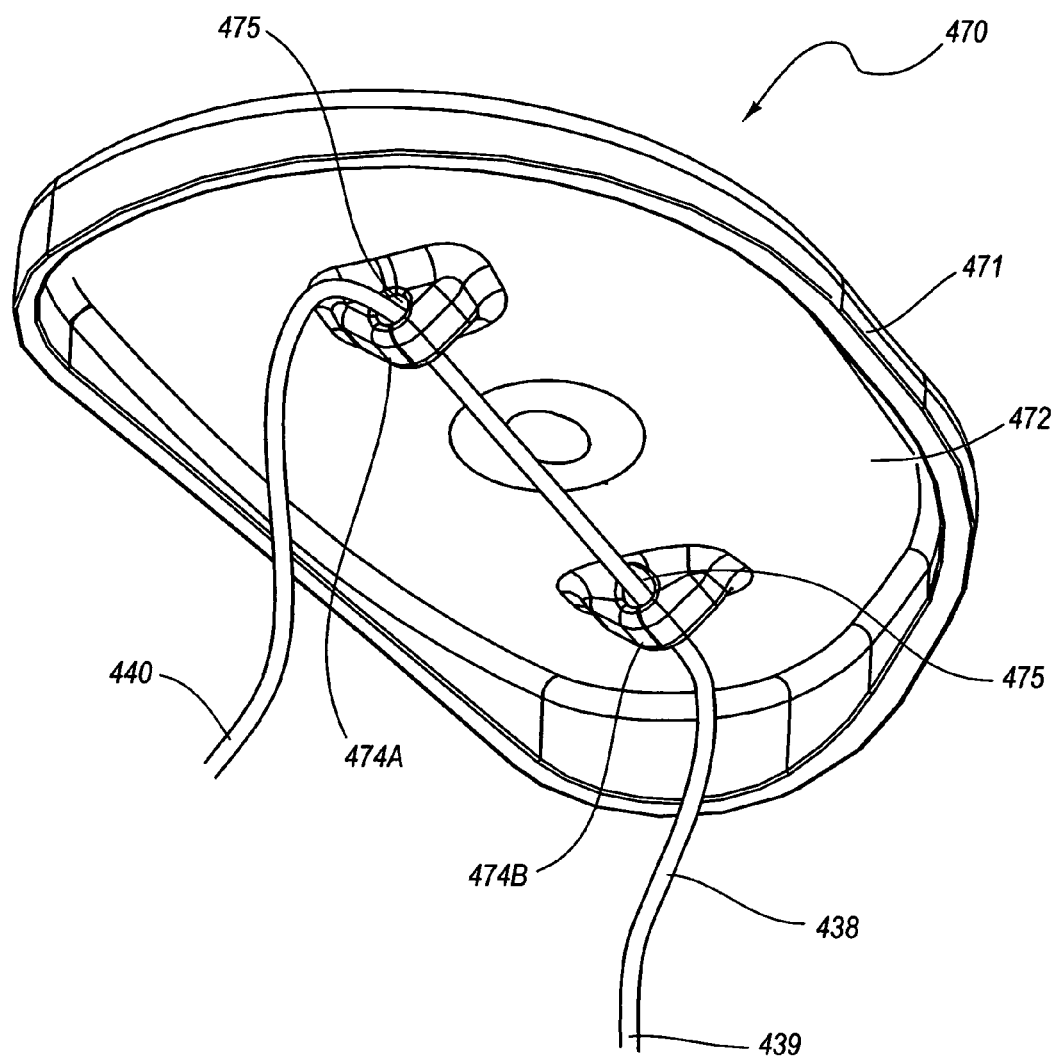
FIG. 14 is a bottom perspective view of an alternative embodiment of an implant having a line slidably connected thereto.

In the embodiment depicted in FIG. 14, an implant 470 has a body 471 with a bottom surface 472. A pair of spaced apart projections 474A and B project from bottom surface 472. A passage 475 extends through each projection 474A and B. Line 438 is passed through each passage 475 so that line 438 is slidably connected to implant 470 with both ends 439 and 440 of line 438 being freely disposed. As will be discussed below in greater detail, in this embodiment both ends 439 and 440 of line 438 are separately connected to the bone. Since line 438 is slidably connected to implant 470, this embodiment functions like a pulley in that a tensioning force applied to one end of line 438 is magnified as is passes through the passages 474. As such, greater force can be used to secure the implant without increasing the load on line 438.

Furthermore, by connecting line 438 to implant 470 at two spaced apart locations the implant is secured in a more stable configuration that prevents unwanted sliding or rotation on the bone. In other embodiments, it is appreciated that line 438 can be connected to only a single projection 474. It is also appreciated that a first line can be connected to projection 474A while a second line is connected to projection 474B. In like manner, it is appreciated that in all embodiment disclosed herein, two or more discrete lines can be connected two each of the implants using any of the methods disclosed herein. It is also appreciated that there are still a large number of other ways in which line 438 can be secured to an implant. For example, the line can be welded, press fit, or attached by a variety of different types of fasteners such as bolts, rivets, or clamps. Examples of still other condylar implants having a line connected thereto are also disclosed in the '941 application.

Figure 15:
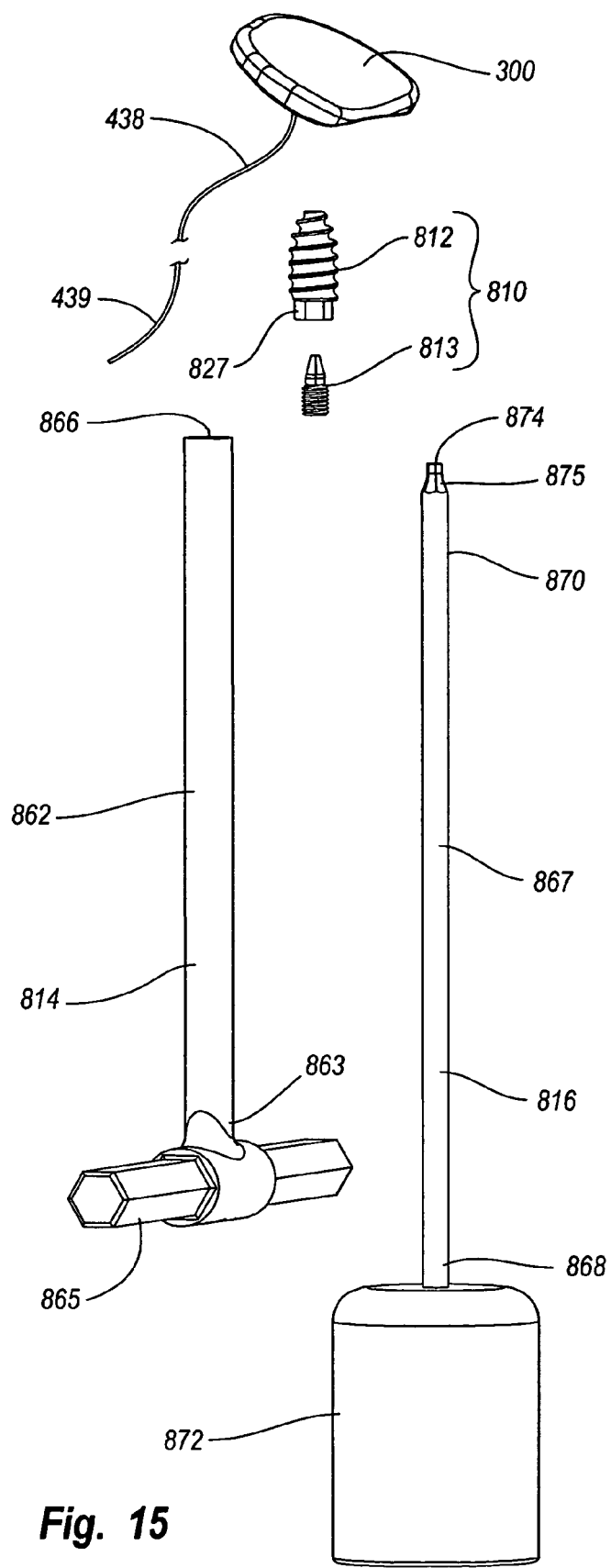
FIG. 15 is an exploded view of an anchor assembly for securing a condylar implant to a tibia.

Depicted in FIG. 15 is one embodiment of an anchor assembly 810 used to secure condylar implant 300 to tibia 12. Anchor assembly 810 comprises a bone anchor 812 that operably connects with a lock 813. As discussed below in greater detail, bone anchor 812 is selectively placed by a first drive 814 while lock 813 is selectively placed by a second driver 816.

Figure 16:
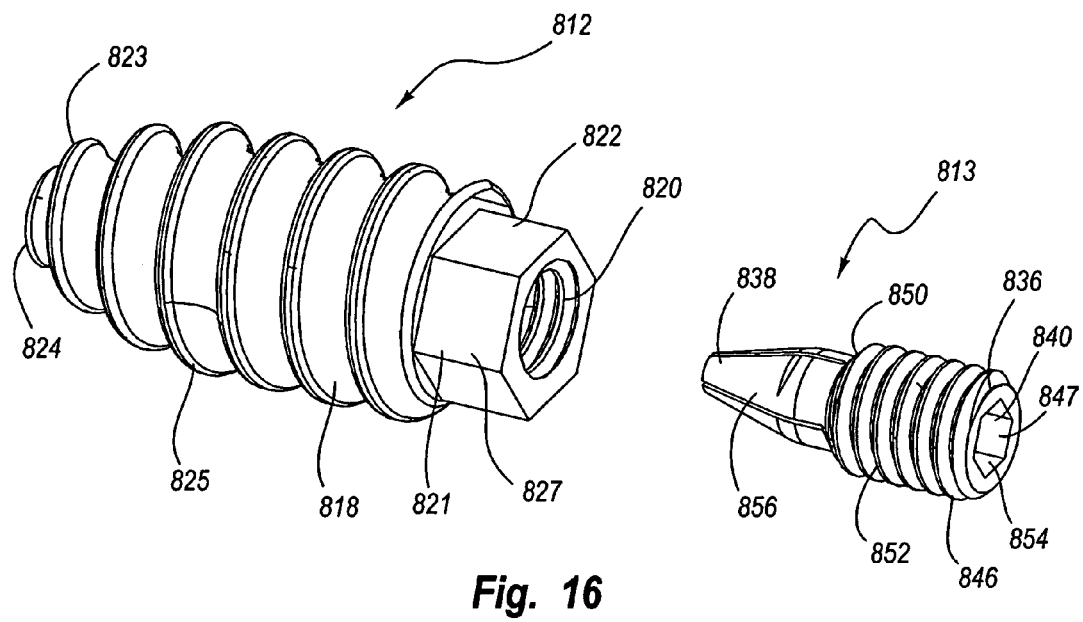
FIG. 16 is an enlarged perspective view of the anchor assembly shown in FIG. 15 including a bone anchor and a lock.

Turning to FIG. 16, bone anchor 812 comprises a tubular body 818 having a substantially cylindrical configuration. Body 818 includes an interior surface 820 and an exterior surface 821 that each extend between a proximal end 822 and an opposing distal end 823. Distal end 823 tapers to a reduced nose 824. Formed at proximal end 822 is an engaging head 827 having an exterior surface with a transverse cross section that is polygonal or any other non-round configuration. As a result, first driver 814 can connect with engaging head 827 to selectively rotate bone anchor 812. Encircling and radially outwardly projecting from exterior surface 821 are one or more helical threads 825. Threads 825 can be conventional or self-taping and extend radially outward beyond the outer perimeter of engaging head 827. In alternative embodiments, threads 825 can be replaced by ridges, barbs, or other bone engaging structures used in conventional bone anchors. Bone anchor 825 can be formed of a biocompatible metal, a bioabsorbable polymer, a bioactive ceramic, or any other desired material.

Figure 17:
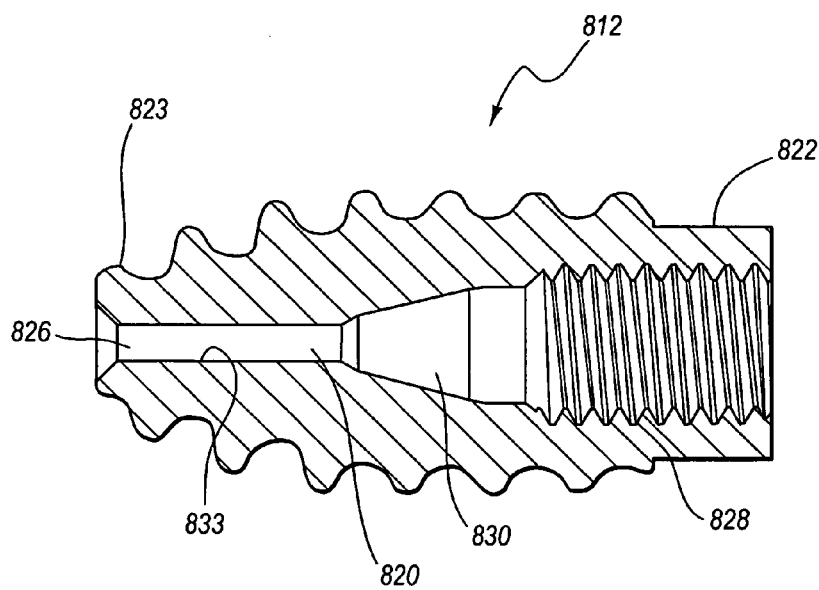
FIG. 17 is a cross sectional side view of the bone anchor shown in FIG. 16.

As depicted in FIG. 17, interior surface 820 bounds a channel 826 longitudinally extending through bone anchor 812. Extending proximal to distal, interior surface 820 comprises a threaded portion 828, a frustoconical tapered portion 830, and a constricted cylindrical portion 833.

Returning to FIG. 16, in the embodiment depicted, lock 813 comprises a collet. In general, lock 813 has a proximal end 836, an opposing distal end 838, and a channel 840 extending therebetween. More specifically, lock 813 comprises a tubular body 846 extending from proximal end 836 to a second end 850. Encircling and radially, outwardly projecting from body 846 are one or more helical threads 852. Threads 852 are configured to engage with threaded portion 828 of bone anchor 812. At least a portion of channel 840 extending through body 846 is bounded by an interior surface 847 having a polygonal or other non-circular transverse cross section so that second driver 816 (FIG. 15) can be secured therein for selective rotation of lock 813.

Figure 18:
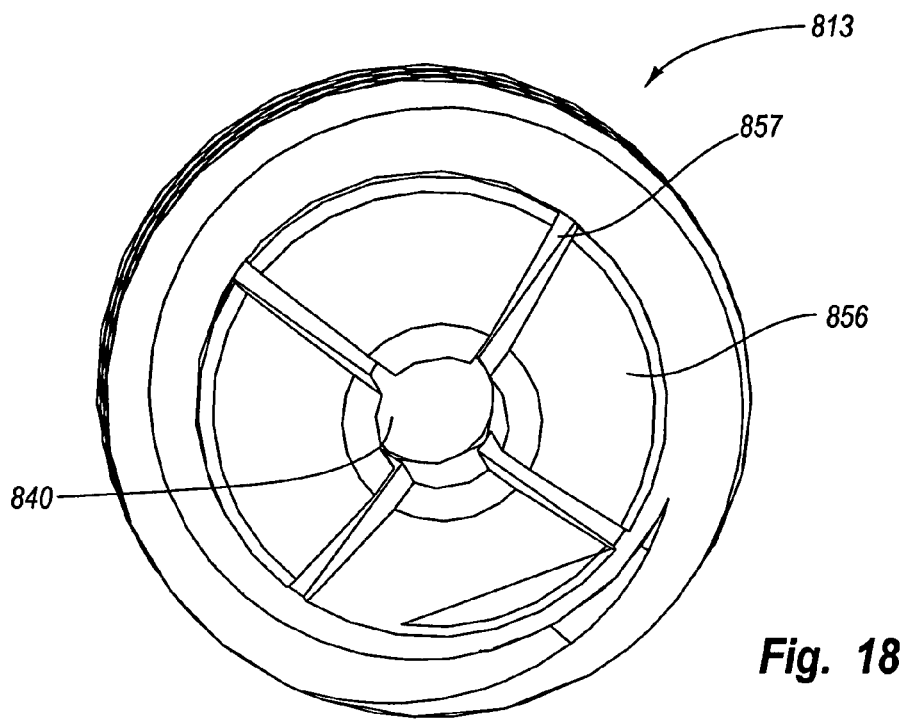
FIG. 18 is an elevated front view of the lock shown in FIG. 16.

Projecting from second end 850 of body 846 are a plurality of flexible fingers 856. As depicted in FIG. 18, four finger 856 are provided with each finger 856 being separated by a slot 857 extending along the length of fingers 856. In alternative embodiments, two or more fingers 856 can be used. The distal end of each finger 856 is radially, inwardly tapered.

Figure 19:
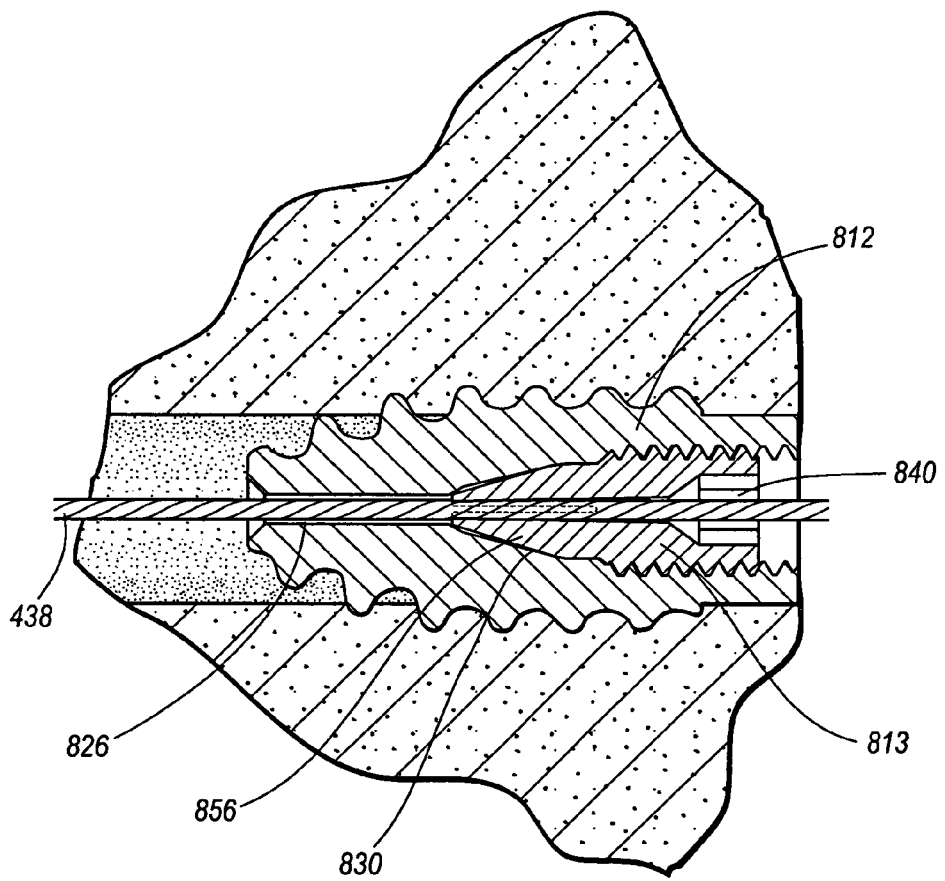
FIG. 19 is a cross sectional side view of the assembled anchor assembly shown in FIG. 16 having a line extending therethrough.

As depicted in FIG. 19, during operation lock 813 is partially screwed into proximal end 822 of bone anchor 812. In this position, with fingers 856 unflexed, line 438 is passed through channels 826 and 840. As discussed below in greater detail, when it is desired to secure line 438 relative to bone anchor, lock 813 is advanced further into bone anchor 812 until tightly secured therein. In so doing, fingers 856 of lock 813 bias against tapered portion 830 of bone anchor 812 which causes fingers 856 to radially, inwardly constrict and securely engage line 438. In this position, line 438 is prevented from being pulled in either direction. However, line 438 can again be freely moved by simply unscrewing lock 813 from within bone anchor 812 so that fingers 856 are able to freely, outwardly flex.

Returning to FIG. 15, first driver 814 comprises a tubular shaft 862 having a proximal end 863 and an opposing distal end 864. A handle 865 is formed at proximal end 863. A passage 866 extends through shaft 862 and handle 865 so that line 438 can pass completely through first driver 814. Passage 866 at distal end 864 has an interior surface that is complementary to the exterior surface of engaging head 827 of bone anchor 812. As such, first driver 814 can be selectively coupled with bone anchor 812 for selective rotation of bone anchor 812.

Second driver 816 also comprises a tubular shaft 867 having a proximal end 868 and an opposing distal end 870. A tubular handle 872 is mounted proximal end 868. As such, a passage 874 extends the length of second driver 816 so that line 438 can extend completely therethrough. Distal end 870 of shaft 867 terminates at a tip 875. Tip 875 has a configuration complementary to channel 840 at proximal end 836 of lock 813. As such, second driver 816 can be selectively coupled with lock 813 for selective rotation of lock 813.

Figure 20:
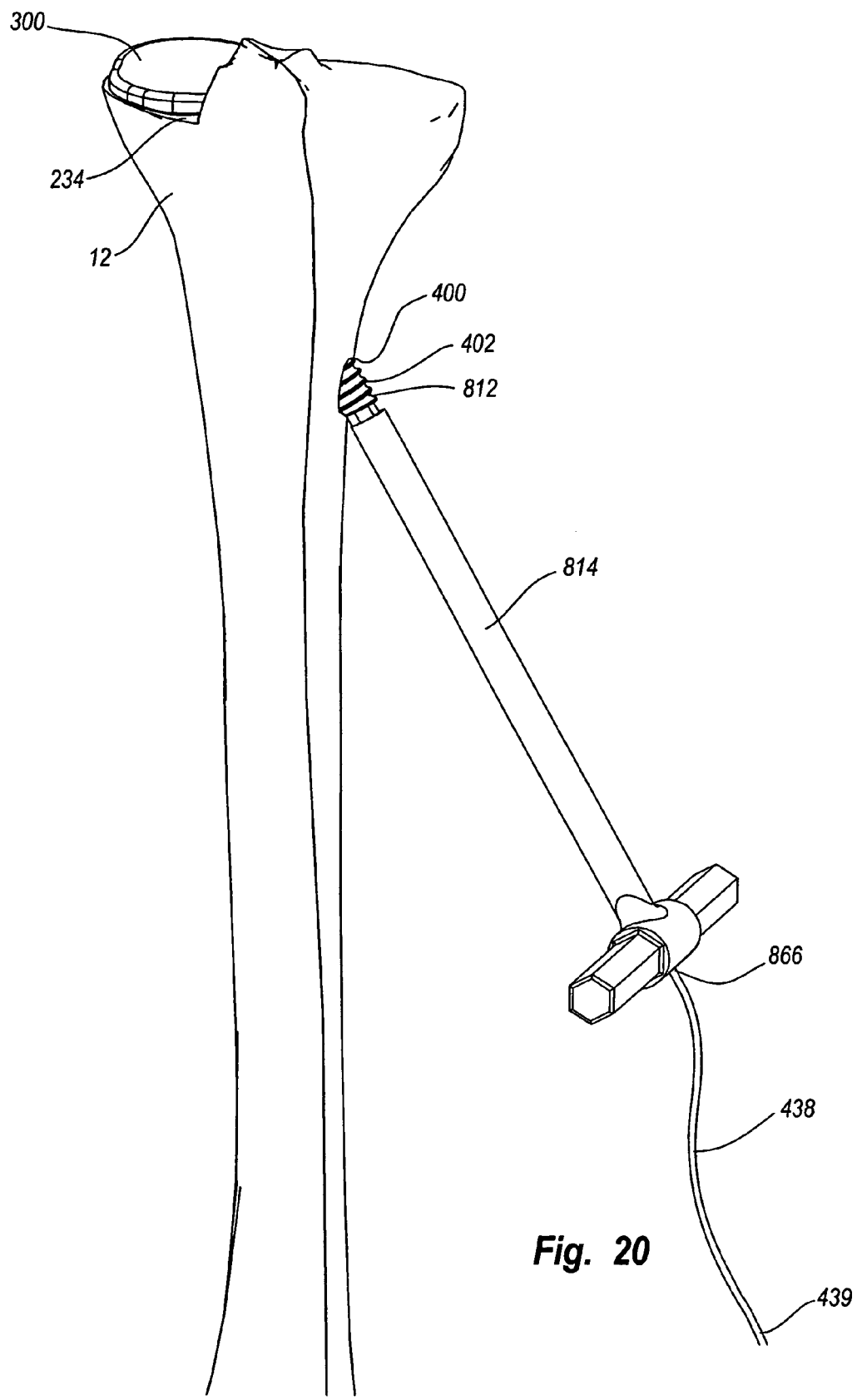
FIG. 20 is a perspective view of an implant mounted on a tibia with the anchor assembly of FIG. 19 being mounted to the tibia.

Turning to FIG. 20, to facilitate mounting of condylar implant 300, with the second end of line 438 connected to implant 300, first end 439 of line 438 is passed through tunnel 400 from second end 404 (FIGS. 3 and 4) to first end 402. In one embodiment this is accomplished by passing an instrument up through tunnel 400 from first end 402 to second end 404. The instrument is then used to grab first end 439 of line 438 and pull it down through tunnel 400. Other techniques can also be used.

Line 438 is continually pulled through tunnel 400 to remove all slack. With the slack removed, condylar implant 300 is slid onto resected surface 234 so as to fit within pocket 194. Here it is noted that because condylar implant 300 has a relatively low profile, condylar implant 300 can be easily passed through the relatively small incision that was originally formed over the medial meniscus. This is in contrast to other conventional procedures where larger incisions must be made to either allow placement of an implant having a large stem that is embedded within the bone for securing or to provide access room to enable securing the implant by passing screws down through the top of at least a portion of the implant.

Once implant 300 is positioned, bone anchor 812 is fed onto line 438. Specifically, with lock 813 partially inserted into bone anchor 812, as discussed above with reference to FIG. 19, first end 439 of line 438 is passed distal to proximal through channels 826 and 840 of bone anchor 812 and lock 813. First end 439 of line 438 then is passed distal to proximal through passage 866 of first driver 814 so that first driver 814 can removably couple with bone anchor 812. It is appreciated that the above steps can be performed in a variety of different sequences. For example, line 428 can be passed through bone anchor 812 and lock 813 separately before they are connected together.

First driver 814 is then used to screw bone anchor 812, having lock 813 therein, into first end 402 of tunnel 400. Bone anchor 812 is advanced until proximal end 822 passes into tibia 12. In one embodiment, a tap, not shown, is used to initially thread the interior surface of tunnel 400 at first end 402. Alternatively, bone anchor 812 can be self-tapping.

Figure 21:
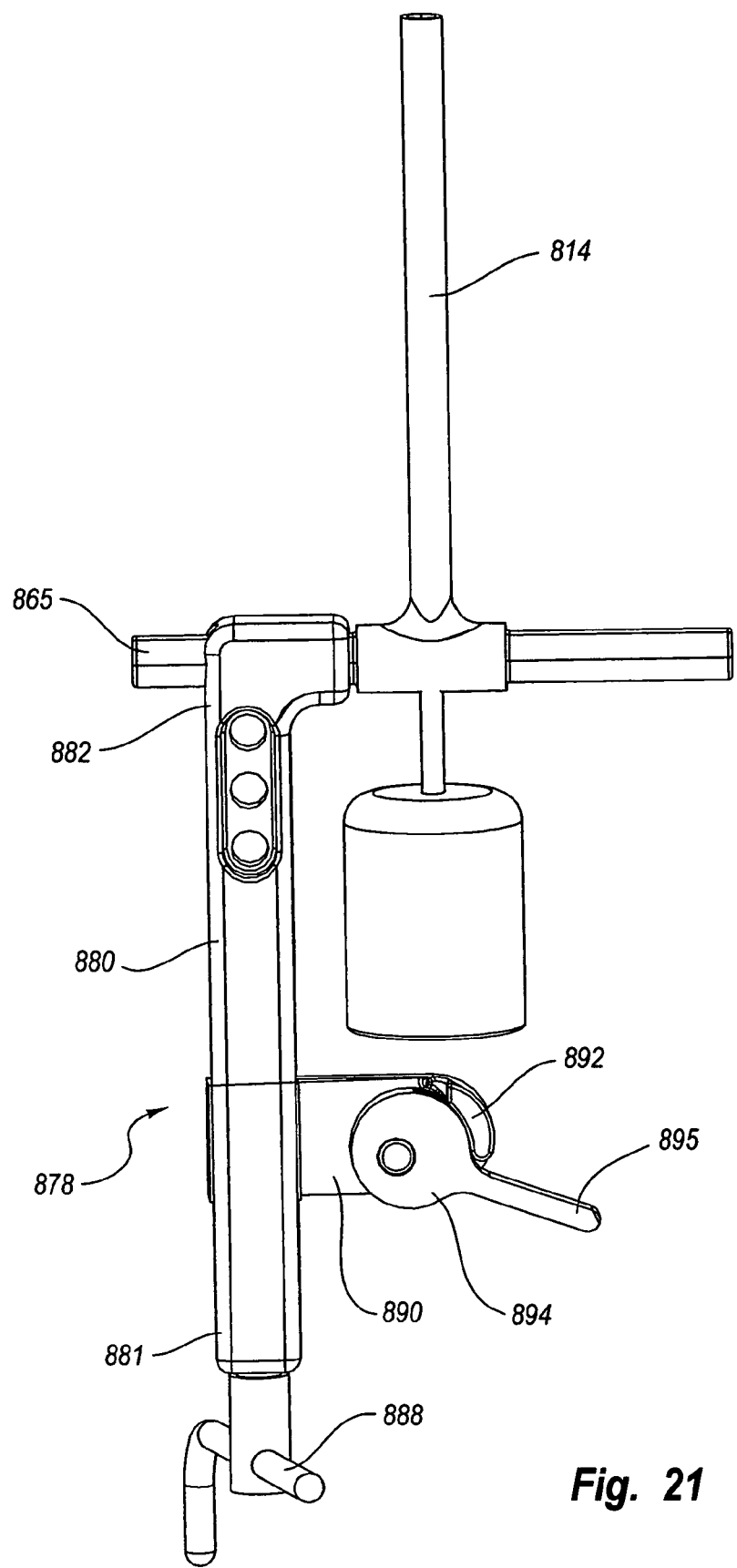
FIG. 21 is an elevated front view of a tensioner.
Figure 22:
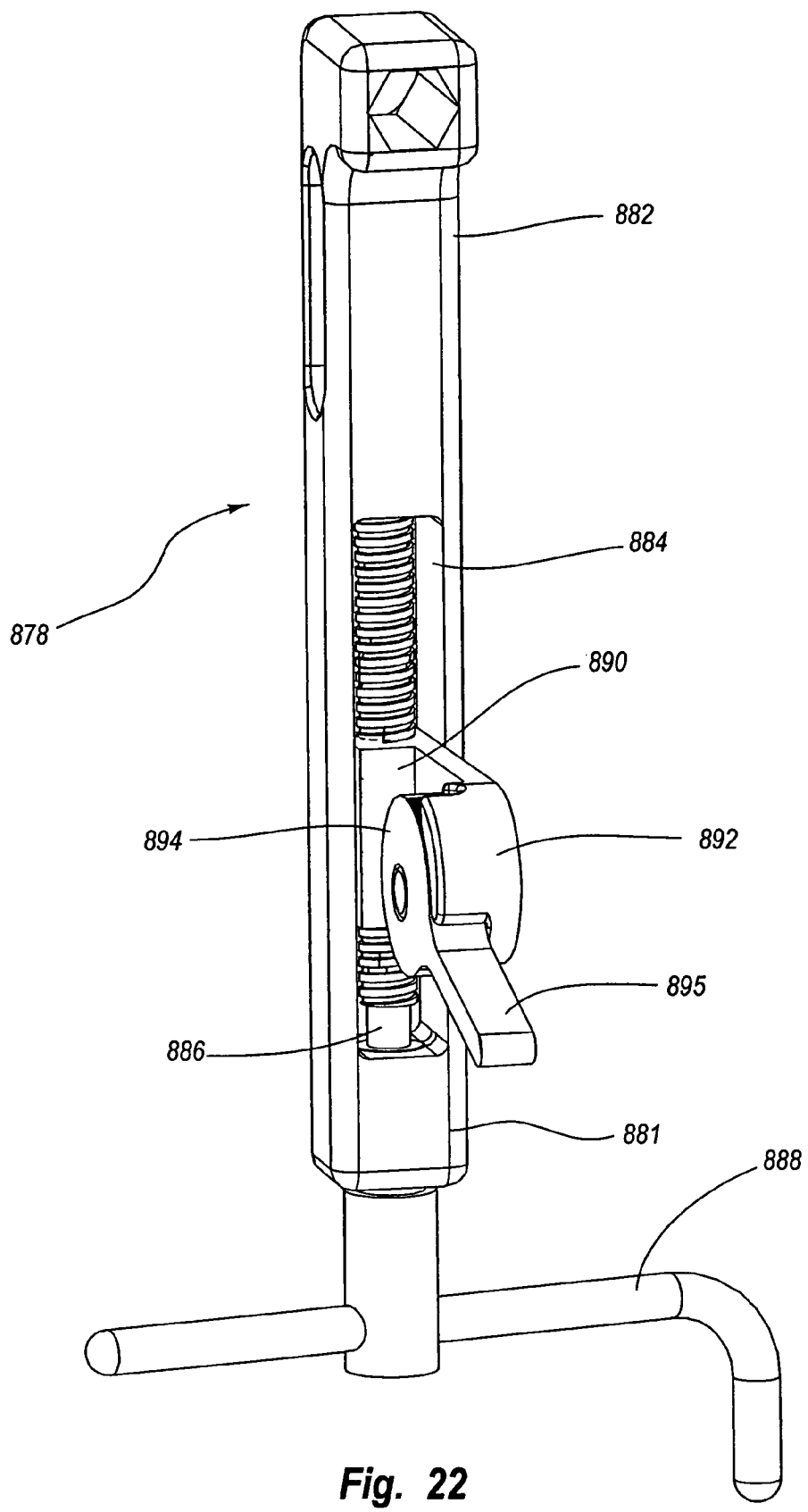
FIG. 22 is an elevated side view of the tensioner shown in FIG. 21.

Next, a tensioner 878 is used to tension line 438. As depicted in FIGS. 21 and 22, tensioner 878 comprises a frame 880 having a proximal end 881 and an opposing distal end 882. Distal end 882 removably connects to handle 865 of fist driver 814. A channel 884 is formed within a portion of frame 880. Rotatably disposed within channel 884 is a threaded shaft 886. A portion of shaft 886 extends beyond proximal end 881 and has a handle 888 connected thereto. Mounted on threaded shaft 886 within channel 884 is a clamp arm 890. Clamp arm 890 is mounted such that rotation of shaft 886 by rotation of handle 888 causes clamp arm 890 to selectively advance along shaft 886 depending on the direction of rotation.

Positioned on clamp arm 890 is a stop plate 892. An eccentrically mounted cam 894 is rotatably mounted to clamp arm 890 and is spring biased against stop plate 892. A handle 895 projects from cam 894. Depressing handle 895 causes cam 894 to rotate away from stop plate 892. Line 438 can then be placed between cam 894 and stop plate 892. When handle 895 is released, cam 894 spring biases against stop plate 892 causing line 438 to be secured therebetween. Because cam 894 is eccentrically mounted, the more tension on line 438 toward first driver 814, the greater the force applied by cam 894 to secure line 438 in place.

Figure 23:
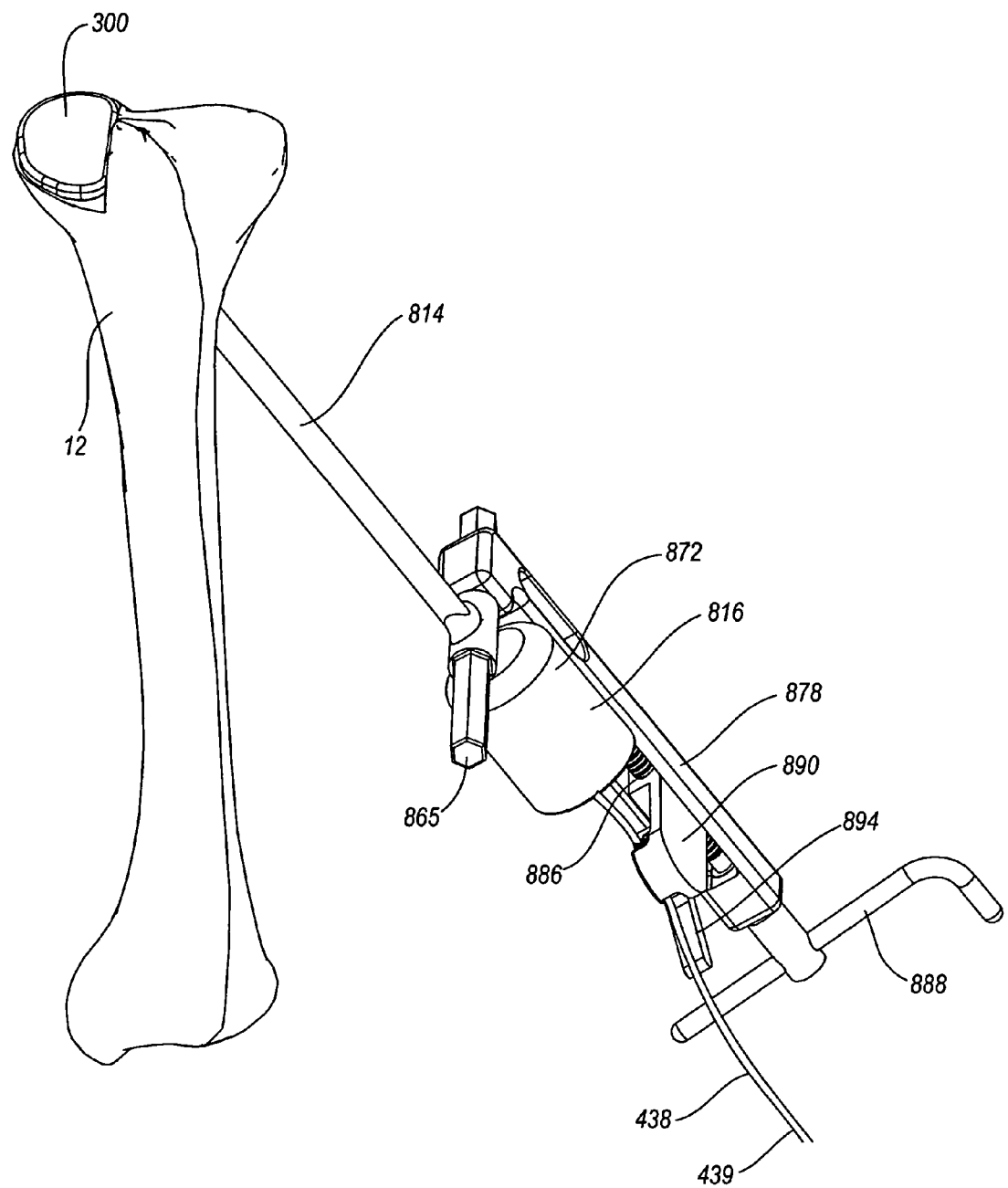
FIG. 23 is a perspective view of the tensioner shown in FIGS. 21 and 22 coupled with the mounted anchor assembly shown in FIG. 20.

Turning to FIG. 23, once bone anchor 812 has been mounted to tibia 12, first end 439 of line 438 is passed distal to proximal through passage 874 in second driver 816. Proximal end 870 of second driver 816 is then advanced proximal to distal through passage 866 of first driver 814. Second driver 816 is advanced until distal tip 875 couples with lock 813. Next, tensioner 878 is connected with handle 865 of first driver 814. Line 438 extending from second driver 816 is then connected to clamp arm 890 by cam 894 as discussed above. Handle 888 of tensioner 878 is then rotated so that clamp arm 890 is moved along threaded shaft 886 away from second driver 816. In so doing, a tension force is applied to line 438.

A force measuring device, such as a transducer, can be coupled with tensioner 878 for measuring the tension force applied to line 438. In turn, the tension force on line 438 is the same force used to bias implant 300 against tibia 12. When a sufficient tension force is applied to line 438, handle 872 of second driver 872 is rotated, thereby causing lock 813 to secure line 438 within bone anchor 812. In one embodiment, the tension force applied to line 438 is in a range between about 25 pounds (110 N) to about 300 pounds (1,335 N) with about 150 pounds (670 N) to about: 250 pounds (1,110 N) being more common. Other forces can also be applied.

Once lock 813 is secured in place, tensioner 878, second driver 816 and first driver 814 are removed. One of the unique features of this embodiment of the present invention is that should the surgeon wish to make some modification to the implant or related anchor system, lock 813 can simply be loosened using second driver 816 to allow the desired movement or adjustment. The above process can then be repeated to resecure implant 300 in place. Once properly position and secured, line 438 is severed just proximal of lock 813. Even after line 438 is severed, however, further tension can be applied to line 438 by backing bone anchor 812 back toward first end 402 of tunnel 400 using first driver 814. Closing procedures for the tissue are then performed.

It is appreciated that many of the mounting steps can be modified or performed in an alternative order. For example, in one method condylar implant can be positioned in pocket 194 prior to having line 438 connected thereto. As previously discussed with regard to FIG. 5, a driver can then be used to secure line 438 to implant 300 by passing retainer 444 through tunnel 400 from first end 402 to second end 404 where retainer is then screwed into implant 300, thereby securing line 438 to implant 300.

In one embodiment of the present invention means are also provided for securing line 438 to bone anchor 812. One example of such means comprises lock 813. In alternative embodiments lock 813 can have a variety of different configurations or be replaced with a variety of different structures. For example, any number of different wedges, cleats, or cams can be placed in bone anchor 812 so that line 438 can be pulled one way through bone anchor 812 but is prevented from being pulled back. In yet other embodiments, once line 438 is tensioned, a lock can be crimped or otherwise secured to line 438. The lock would then bias against bone anchor 812 to prevent line 438 from being pulling back through bone anchor 812. Examples of various locks which can be used are disclosed in U.S. Pat. No. 5,702,397, issued Dec. 30, 1997 and U.S. patent application Ser. No. 09/970,559, filed Oct. 3, 2001. The bone anchors with related line locking structures disclosed in U.S. Pat. No. 5,702,397 and application Ser. No. 09/970,559 are incorporated herein by specific reference.

Figure 24A:
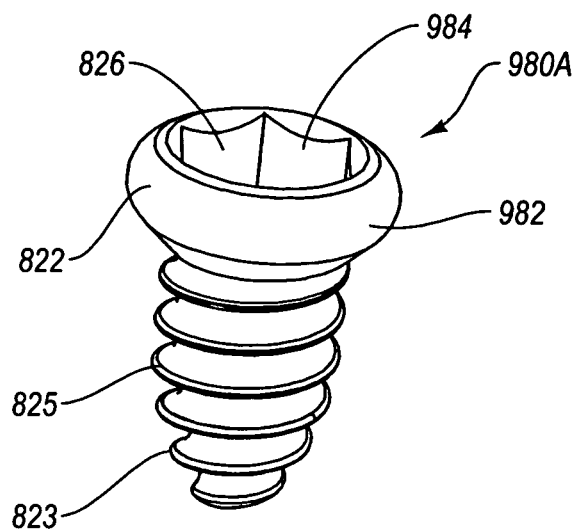
FIGS. 24A and 24B are perspective views of alternative embodiments of bone anchors.
Figure 24B:
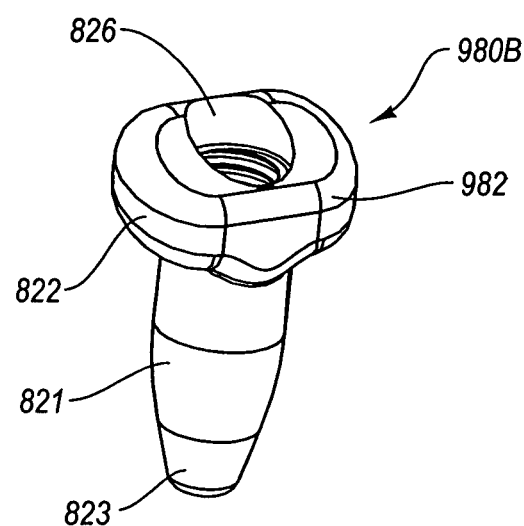

In still other embodiments, it is appreciated that bone anchor 812 can have a variety of different configurations. For example, depicted in FIGS. 24A and 24B are alternative bone anchors 980A and B, respectively. Like elements between the different bone anchors are identified by like reference characters. Each of bone anchors 980A and B is tubular having channel 826 extending therethrough. Likewise, threaded portion 828 and tapered portion 830 (FIG. 17) are formed within each channel 826. In contrast to the polygonal engaging head 827 of bone anchor 812, bone anchor 980A has an enlarged, rounded head 982 formed at proximal end 822. Head 982 has a maximum outer diameter larger than the maximum outer diameter of threads 825. In an alternative embodiment, threads 825 can extend the full length of bone anchor 980A. To facilitate engagement of bone anchor 980A with a driver, a polygonal socket 984 is formed at proximal end 822.

Bone anchor 980B is similar to bone anchor 980A except that helical threads 825 have been completely removed. In this embodiment, exterior surface 821 extending between proximal end 822 and distal end 823 is smooth. Bone anchor 980B is designed to be slid or wedged within the bone tunnel and held in place by the taper along the length thereof and/or the enlarged head 982. By increasing the exterior taper of bone anchor 980B, it is also appreciated that enlarged head 982 can be removed. Because bone anchor 980B is not threaded into the bone, socket 430 at proximal end 416 need not be polygonal to engage a driver but can be round. In alternative embodiment, the interior or exterior surface of head 982 can have a polygonal or other non-circular configuration so as to facilitate positive engagement with a driver.

Figure 25:
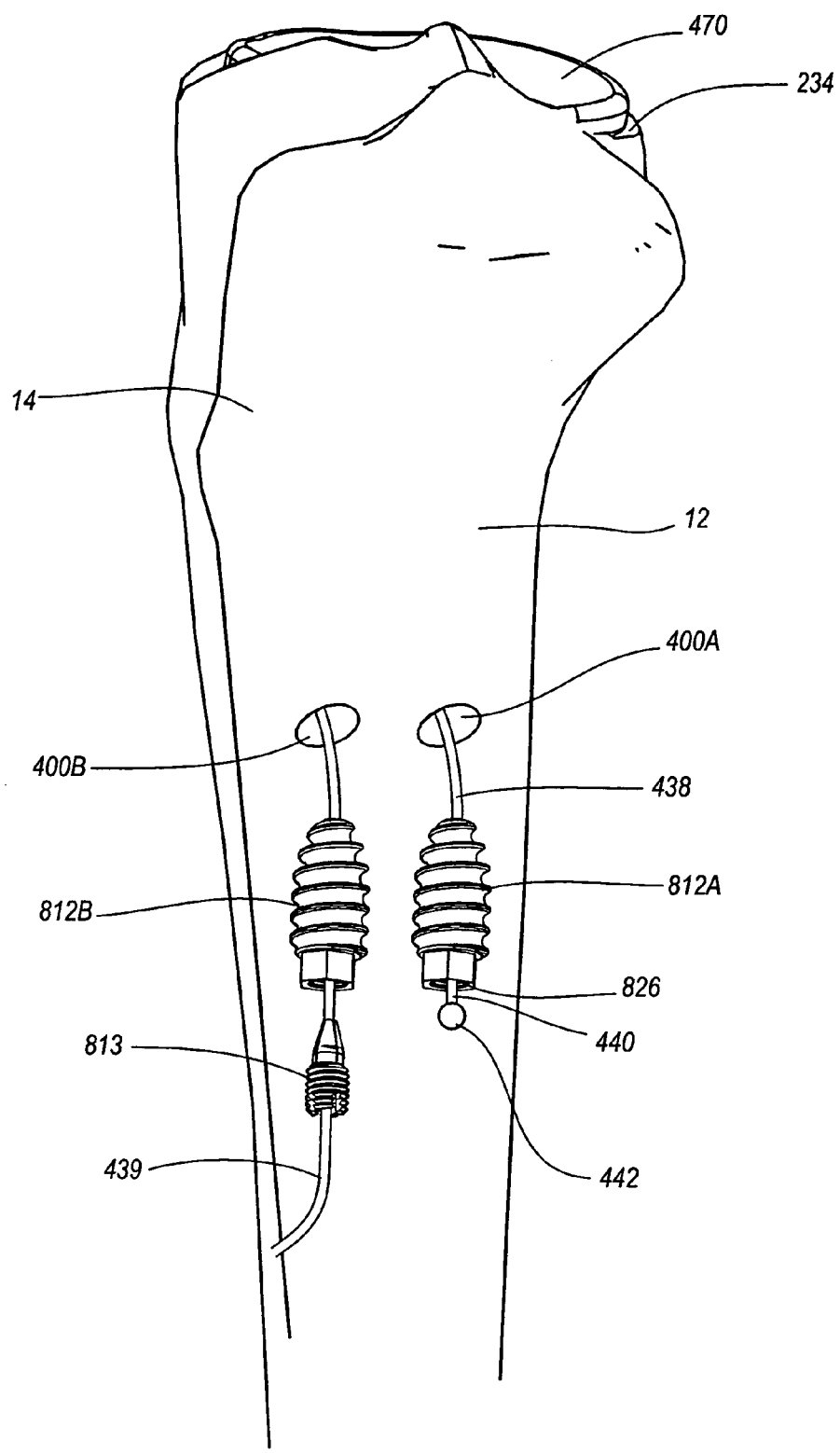
FIG. 25 is a perspective view of a system used to secure the implant shown in FIG. 14 to the tibia.
Figure 26:
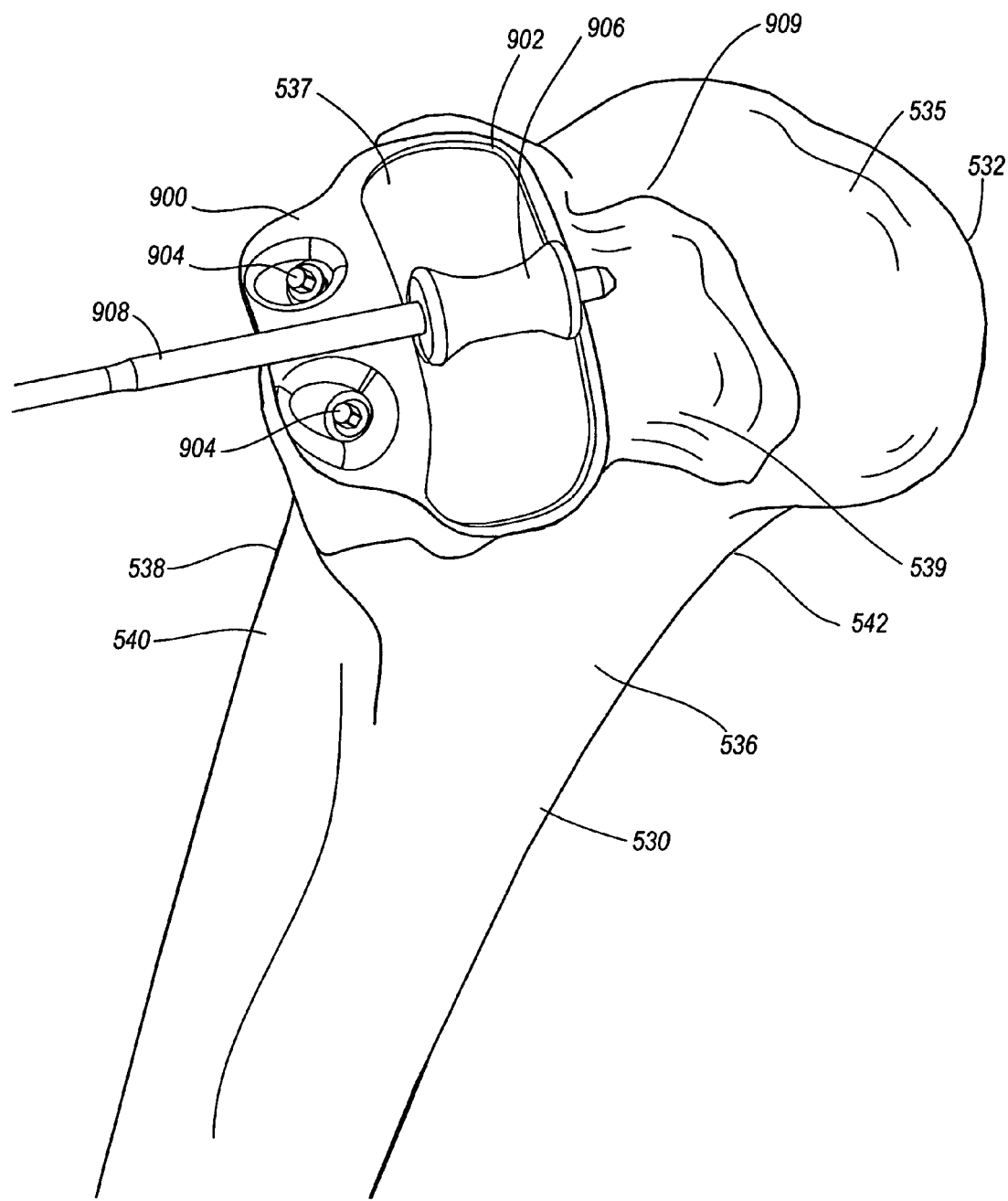
FIG. 26 is a perspective view of a guide template mounted on a medial condyle of a femur and a milling head disposed within an opening of the guide template.

Depicted in FIG. 25 is one embodiment of a system used for mounting implant 470 as previously discussed with regard to FIG. 14. In this embodiment, two a tunnels 400A and 400B extend from lateral side 14 of tibia 12 to resected surface 234. Tunnels 400A and B can be formed having parallel alignment or any desired angle.

To secure implant 470 to tibia 12, first end 439 of line 438 is passed proximal to distal through channel 826 in first bone anchor 812A. First end 439 is then passed up through first tunnel 400A, though passages 475 on implant 470 (FIG. 14), down through second tunnel 400B, and finally through second bone anchor 812B and lock 813. First driver 814 is used to drive bone anchors 812A and B into corresponding tunnels 400A and B. Line 438 is pulled down through second tunnel 400B so as to remove the slack therefrom. In so doing, enlarged head 442 on second end 440 of line 438 is advanced into first bone anchor 812A where head 442 is securely wedged within tapered portion 830 of channel 826 (FIG. 17). With second end 440 of line 438 secured to bone anchor 812A, the same process previously discussed with regard to FIG. 23 is used tension line 438 and secure line 438 to second bone anchor 812 using lock 813.

It is appreciated that first bone anchor 812A can be replaced with a variety of alternative structures that prevent second end 440 of line 438 from being pulled through first tunnel 400A. For example, the first bone anchor can simply comprise an enlarged washer that captures enlarged head 442 but is too big to pass through tunnel 400A. In yet other embodiment, the first bone anchor can simply comprise an enlarged tubular wedge that wedges into tunnel 400A but cannot pass therethrough. In still other embodiments, line 438 can be formed without enlarged head 442. In this embodiment, lock 813 or other wedging or locking type structure can be used to secure second end 440 of line 438 to the first bone anchor. Where two separate lines 438 are connected to an implant, each line is extended through a corresponding tunnel. The process discussed with regard to FIG. 23 is then separately performed for each separate line.

Line 438 and anchor assembly 810 is one embodiment of means for securing an implant to a bone. It is appreciated, however, that other anchoring techniques can also be used. For example, another system for securing an implant to a bone is disclosed in U.S. patent application Ser. No. 10/798,665, filed Mar. 11, 2004 which is incorporated herein by specific reference.

By using the above discussed implants and anchor assemblies with the corresponding methods and instruments, it is appreciated that the implants can be securely mounted to tibia 12 using procedures that are minimally invasive. Furthermore, because the implants are only secured in place after they are positioned on the proximal end of the tibia, the surgeon can easily switch out different sizes of implants when trying to determine an appropriate fit. Likewise, because the anchoring assemblies are operated through the first end of the tunnel which is remote from the implant, the inventive anchoring assemblies enable the surgeon to easily adjust the placement of the implant during initial positioning and to subsequently remove the implant should a replacement be required at a later date.

Furthermore, as a result of using a flexible line to secure the implants, the surgeon can select the best location for forming the tunnel and mounting the bone anchor at the time of the operation. That is, the surgeon is not limited to forming the tunnel at a predefined location based on structural limitations imposed by the implant. In addition, because the line can be relatively small, the size of the required tunnel can be minimized, thereby minimizing the amount of bone that needs to be removed when forming the tunnel. Replacement of a worn or damaged implant is also relatively easily achieved by cutting the line.

Because the inventive implants, anchor assemblies, tissue preparation instruments, and corresponding methods each produce independently unique benefits, it is appreciated that theses various features can be used independently with other conventional apparatus and techniques. For example, in one embodiment a larger incisions can be made at the knee of a patient and the proximal end of tibia 12 resected using conventional resection techniques. In this embodiment, tunnel 400 can be formed either before or after the resection of tibia 12. Once the tibia is resected and the tunnel formed, the above procedure can then be used to secure condylar implant 300. In another alternative, tunnel 400 can be formed and tibia 12 resected as discussed above. However, once tibia 12 is resected, a conventional implant can be mounted on tibia 12 using conventional techniques.

The above discussed embodiments relate to mounting a condylar implant on tibia 12. As previously mentioned, however, the present invention can also be used to mount other types of implants on other articulation surface so as to achieve one or more of the same benefits. For example, the '941 application also discloses a full tibial implant and methods for mounting.

Figure 45:
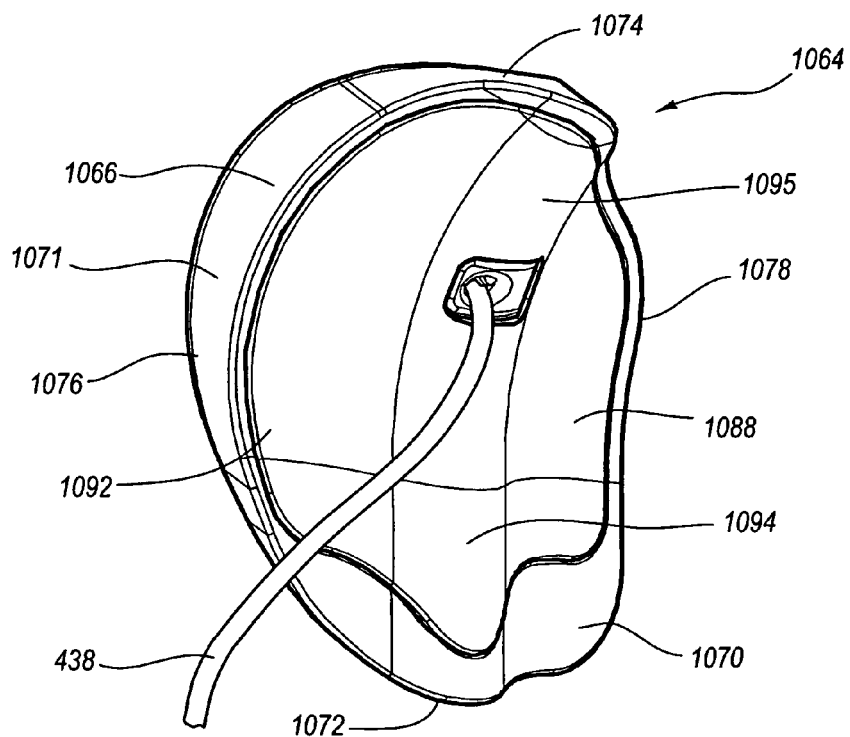
FIG. 45 is a back perspective view of the trochlear groove implant shown in FIG. 43 with a line connected thereto.

Features of the present invention can also be used for mounting a femoral implant on the distal end of a femur. Like elements between different embodiments are identified by like reference characters. For example, depicted in FIG. 45 is a distal end 532 of a femur 530 having a medial side 540 and a lateral side 542 that extend between an anterior side 538 and a posterior side 536. Distal end 532 of femur 530 terminates at a lateral condyle 535 and a medial condyle 537 with a trochlear groove 539 disposed therebetween.

Mounted on medial condyle 537 is a guide template 900. Guide template bounds an elongated opening 902 that extends therethrough and which is configured to closely fit over a predefined portion of an articulation surface of medial condyle 537. Opening 902 bounds the area where the bone is to be resected and a condylar implant mounted. Guide template is curved and comes in a variety of different sizes and shapes so that a proper fit can be made on medial condyle 537. Once a proper sized and fitting guide template 900 is positioned, guide template 900 is secured in place by spaced apart screws 904 that are screwed through mounting holes in guide template 900 and into the medial side of femur 530.

In one embodiment, a milling head 906 is used to facilitate resection of medial condyle 537 bounded by guide template. Milling head 906 has a substantially hour-glass configuration and has an elongated handle 908 projecting from one side and a stem 909 projecting from the other. Milling head 906 is positioned within opening 902 in a medial-lateral orientation with handle 908 projecting from medial side 540 of femur 530. In this orientation, milling head 906 is rapidly rotated and then selectively moved within opening 902 anterior-posterior. This movement is guided by the sides of guide template 900 bounding opening 902. Milling head 906 grinds away the bone bounded within opening 902 until handle 908 and stem 909 rest against guide template 900, thereby preventing milling head 906 from descending further into the bone.

Because guide template 900 is curved anterior-posterior, the milled pocket formed by milling head 906 is outwardly arched anterior-posterior. Likewise, because milling head 906 is curved lateral-medial, the milled pocket is also outwardly arched lateral-medial. As such, the recessed pocket produced by milling head 906 is arched anterior-posterior and lateral-medial. Again, this pocket configuration enables the formation of a low profile implant having substantially uniform thickness and strength. Furthermore, the pocket formation produces a stable platform for the implant having a complementary configuration. In alternative embodiments, it is again appreciated that milling head 906 can have a variety of different configurations.

Figure 27:
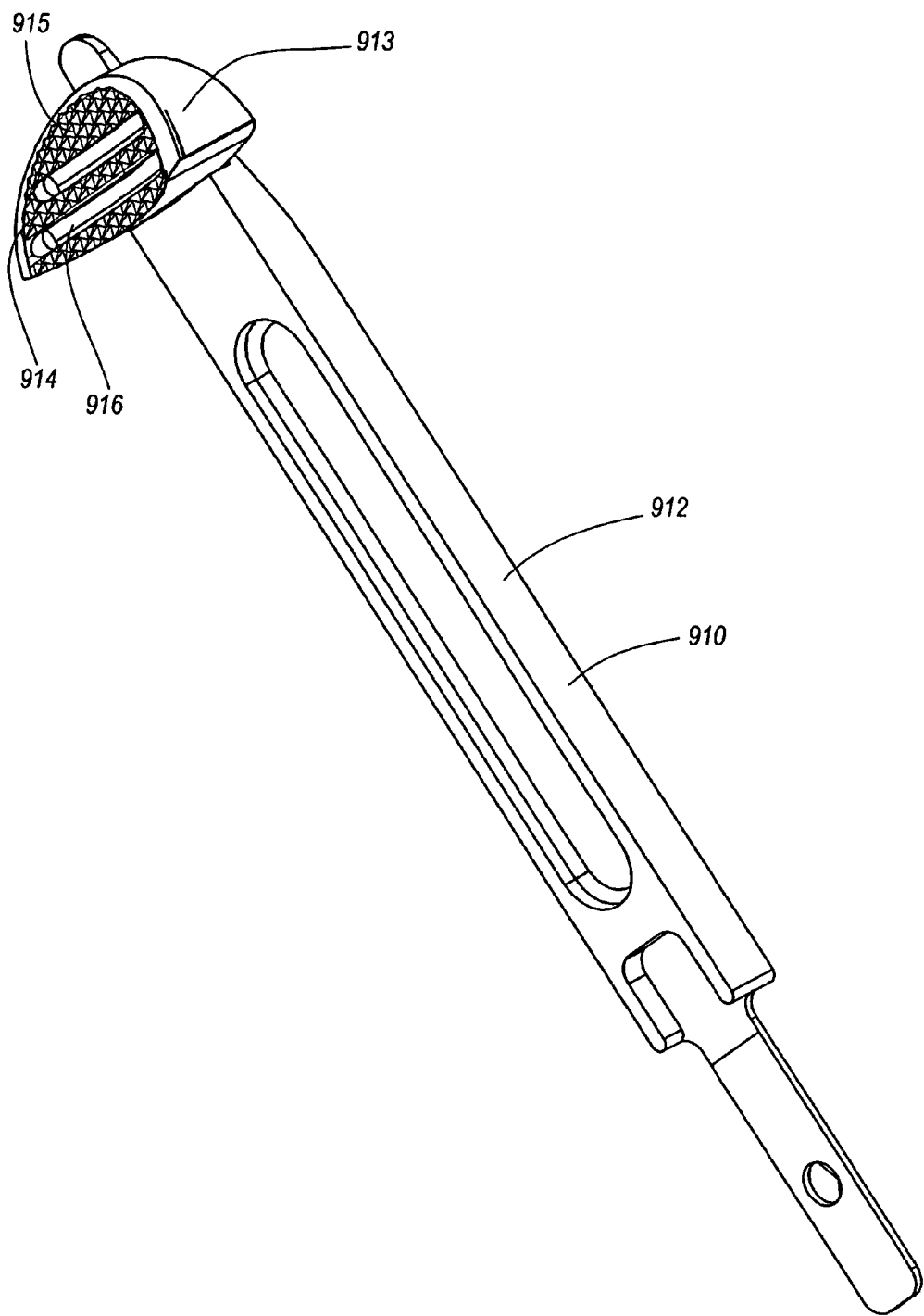
FIG. 27 is a perspective view of a rasp that is selectively used with the guide template shown in FIG. 26.
Figure 28:
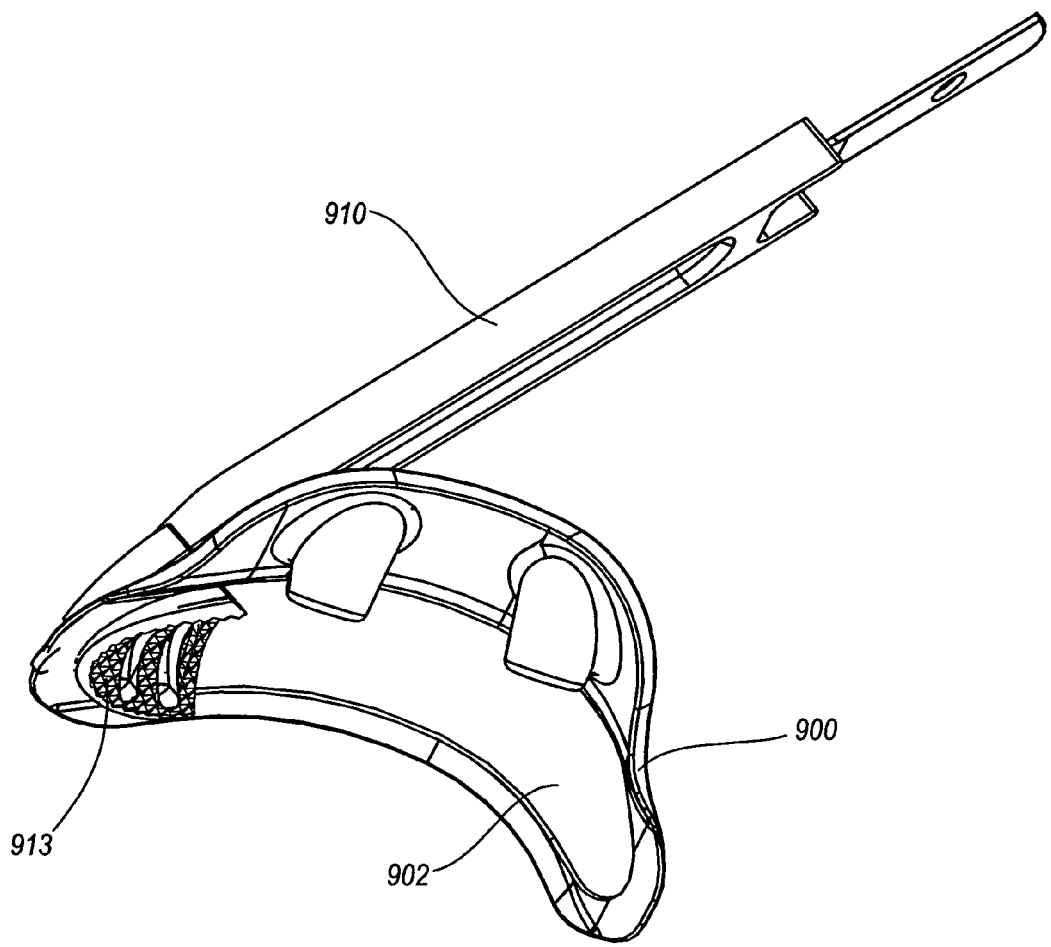
FIG. 28 is a perspective view of the rasp shown in FIG. 46 being used with the guide template of FIG. 26.

As depicted in FIGS. 27 and 28, a rasp 910 can be used to form rounded ends for the recessed pocket. Rasp 910 comprises an elongated handle 912 having a cutting mount 913 mounted on the end thereof. Cutting mount 913 has a generally semi-circular transverse cross section with a concave cutting surface 914. Formed on cutting surface 914 are a plurality of cutting teeth 915. Extending through cutting mount are a plurality of slots through which bone fragments can be removed. Cutting mount 913 is configured to be reciprocally moved within the opposing ends of opening 902 of guide template 900 so as to form rounded ends on the pocket formed to receive the implant.

Once the recessed pocket is finished, a tunnel guide can be used to form tunnel 400 extending from lateral side 542 of femur 530 to the recessed pocket. Examples of such tunnel guides and corresponding method of use are disclosed in the '941 application. Alternatively, tunnel 400 can be drilled starting at the recessed pocket and extending to the lateral or medial side of the femur. Because it is less critical where tunnel exits on the lateral or medial side, a tunnel guide is not required but could, if desired, still be used. This process can also be used on the tibial side.

Figure 29:
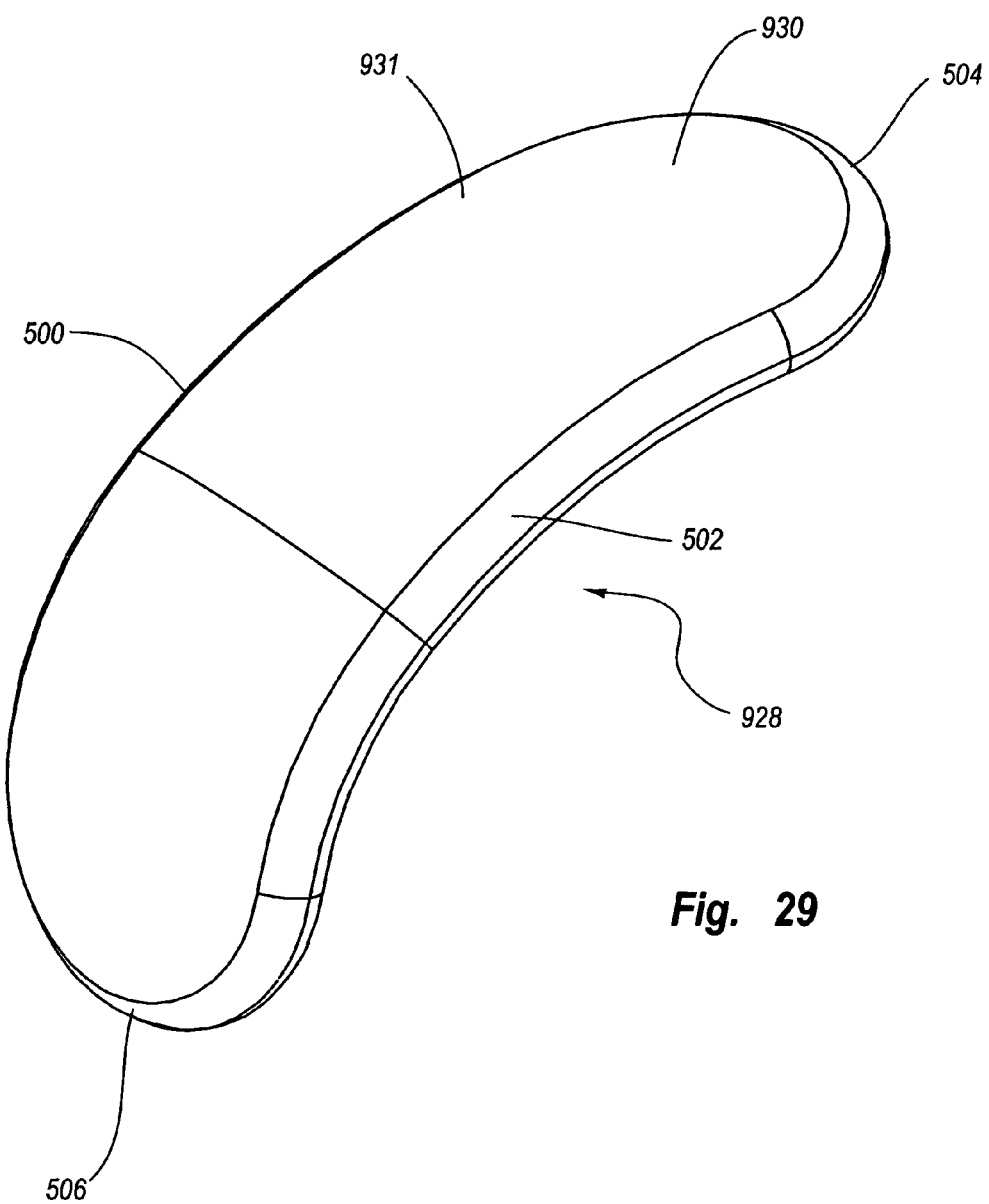
FIG. 29 is a top perspective view of a femoral condylar implant.
Figure 30:
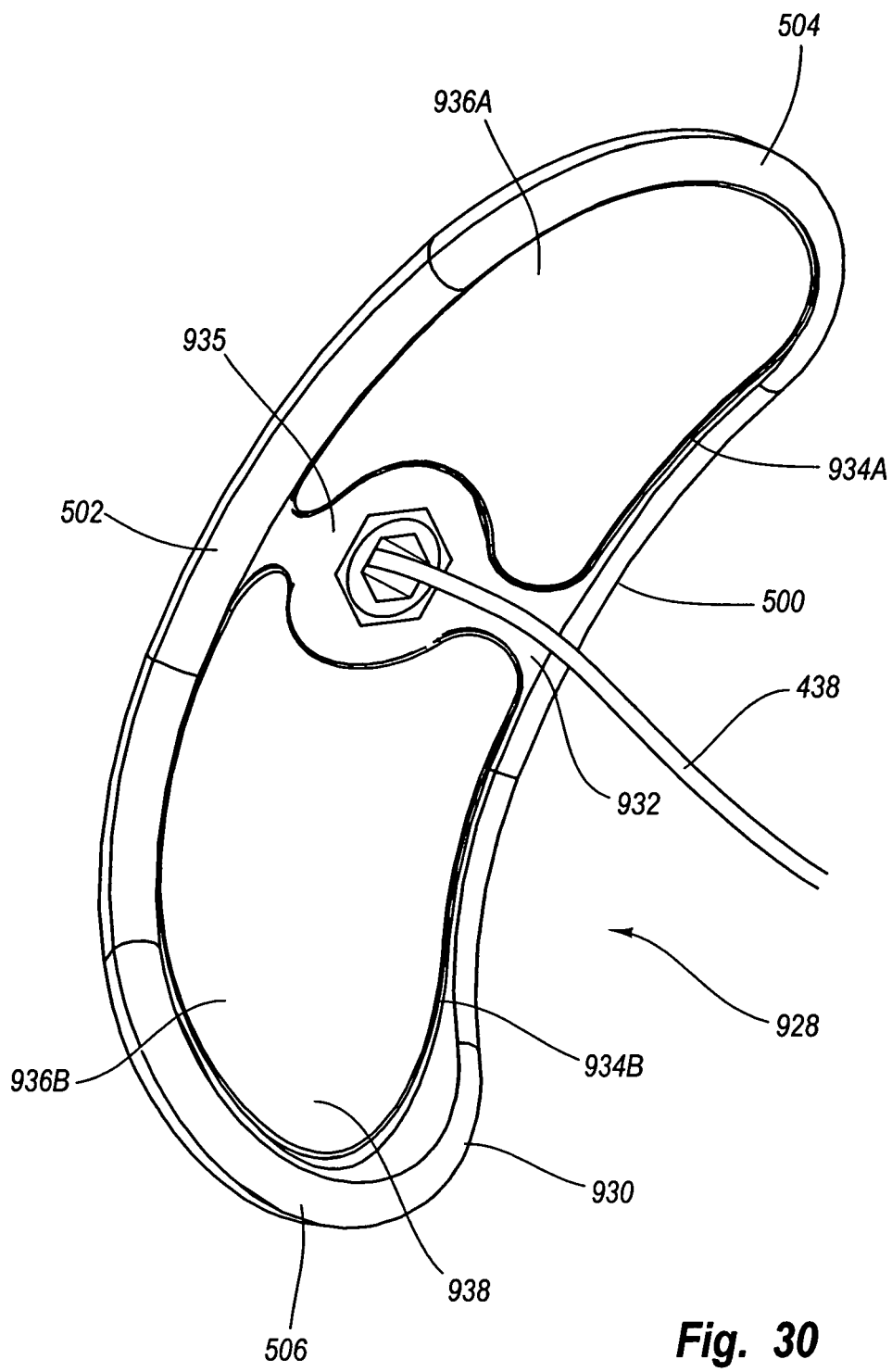
FIG. 30 is a bottom perspective view of the femoral condylar implant shown in FIG. 29 having a line connected thereto.

Once tunnel 400 is formed, a femoral condylar implant 928 is then positioned within the recessed pocket. As depicted in FIGS. 29 and 30, in one embodiment femoral condylar implant 928 comprises an elongated body 930 having a first side 500 and an opposing second side 502 that extends between opposing ends 504 and 506. Body 920 also has a curved articular surface 931 and an opposing bottom surface 932. In one embodiment, articular surface 931 can have a continuous convex curvature which extends between opposing sides 500 and 502 and a continuous convex curvature which extends between opposing ends 504 and 506.

A pair of pockets 934 A and B are formed on bottom surface 932 and are separated by a bridge 935. Disposed within each pocket 934A and B is an inlay 936A and B of porous bone ingrowth material. Bridge 935 and inlays 936A and B substantially comprise a bone apposition surface 938. Bone apposition surface 938 can have a configuration complementary to the formation of the recessed pocket formed on medial condyle 537. Bone apposition surface 938 can also have a configuration complementary to articular surface 931. In one embodiment, bone apposition surface 938 can have a continuous concave curvature which extends between opposing sides 500 and 502 and a continuous concave curvature which extends between opposing ends 504 and 506. As a result, condylar implant can have a substantially uniform thickness along its length.

Connected to bridge 935 is line 438. It is appreciated that the various alternatives as previously discussed with regard to the tibial condylar implants and the methods for connecting line 438 thereto are also applicable to femoral condylar implant 928.

Figure 31:
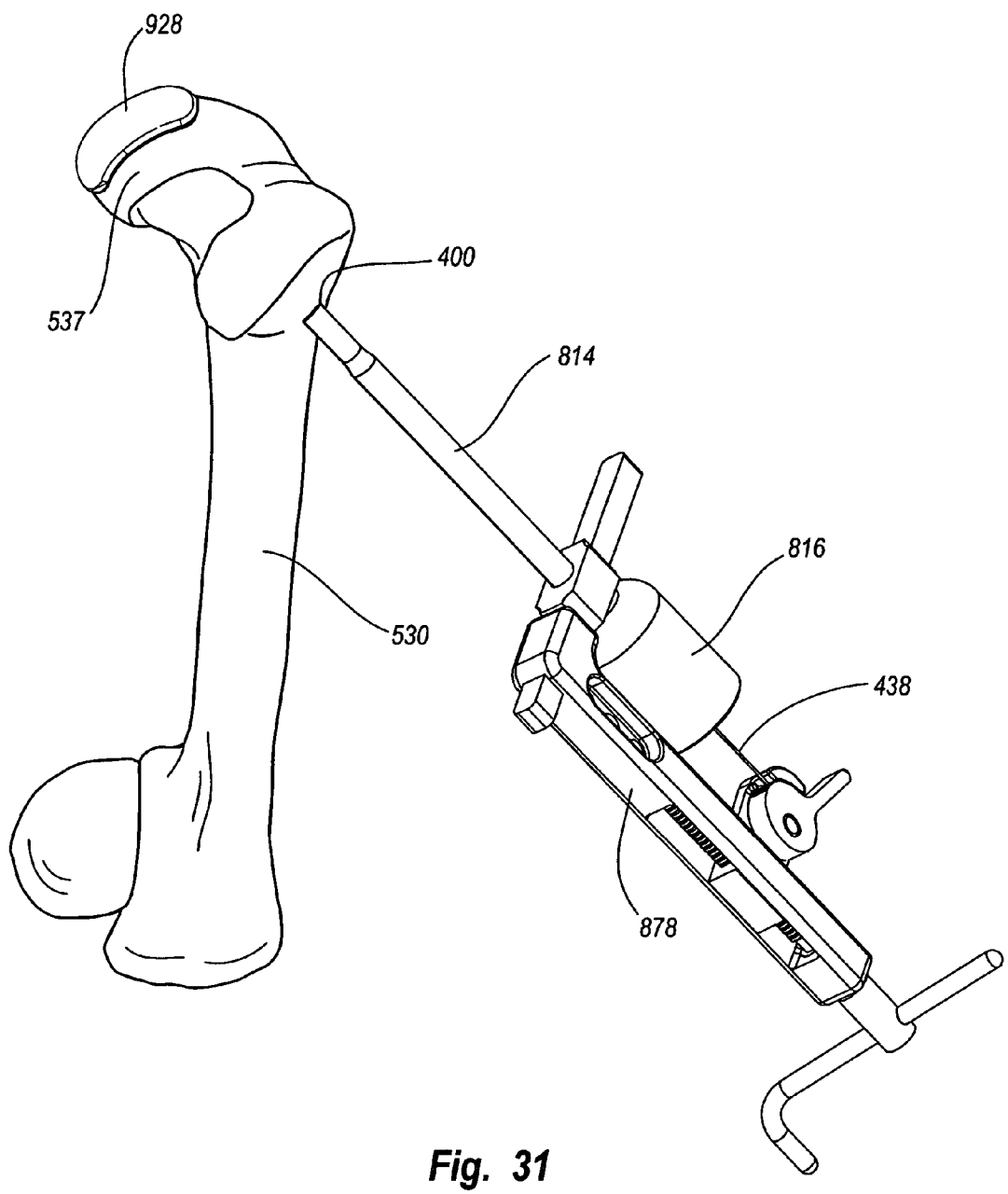
FIG. 31 is a perspective view of the system shown in FIG. 23 being used to secure the femoral condylar implant of FIG. 29 to the femur.

Finally, turning to FIG. 31, femoral condylar implant 928 is secured to femur 530 using anchor assembly 810 (FIG. 15) and the instruments and techniques as previously discussed with regard to FIGS. 15-25. The same alternatives as previously discussed with regard to FIGS. 15-25 are also applicable to the attachment of femoral condylar implant 928. For example, two separate tunnels can be formed on femur 530 that intersect with the recessed pocket on medial condyle 537. Opposing ends of a single line 438 slidably connected to implant 928 can be passed through the separate tunnels and secured with corresponding bone anchors. Alternatively, two separate and discrete lines 438 can be connected to femoral condylar implant 928, each line being disposed in a separate tunnel.

Figure 32:
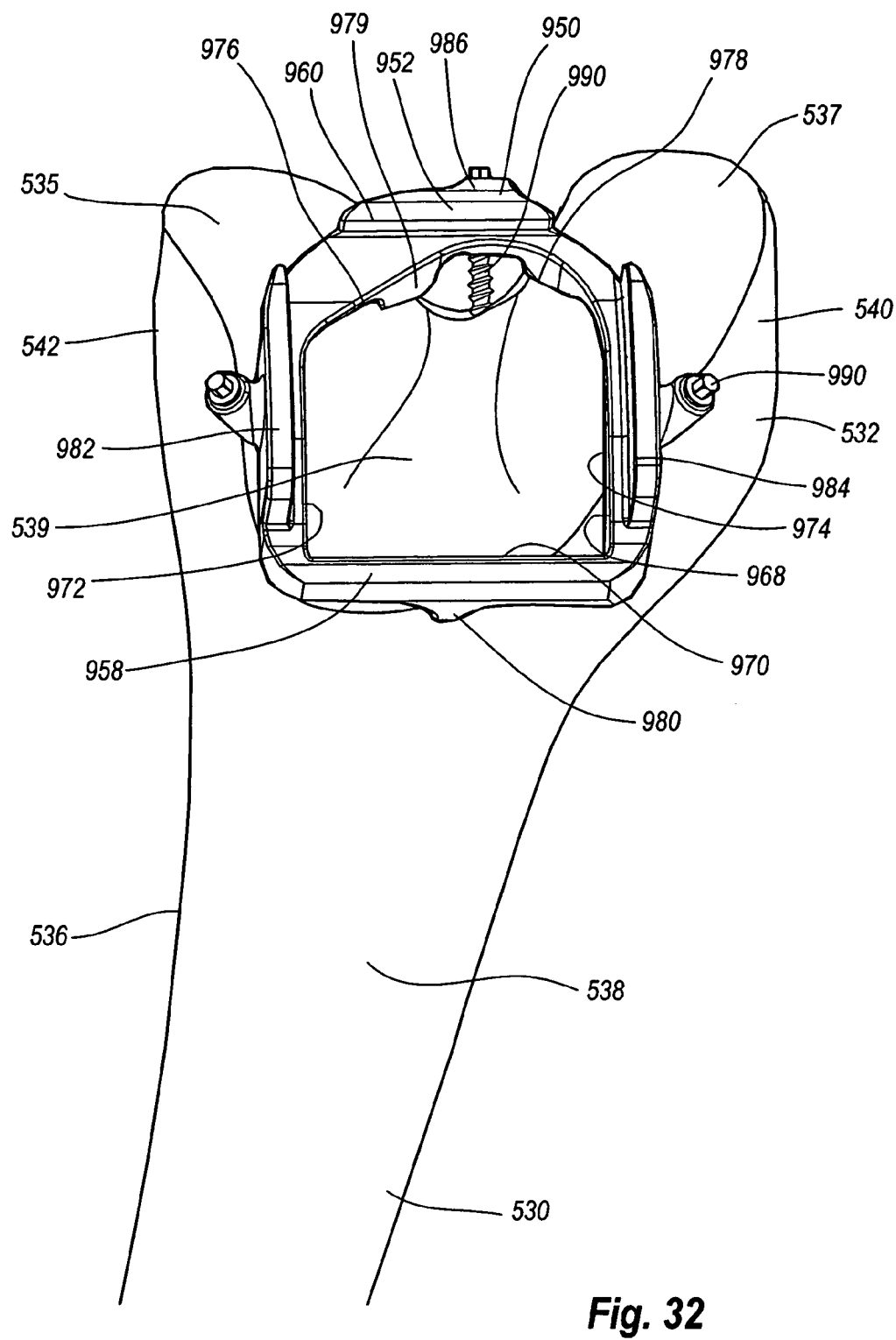
FIG. 32 is a perspective view of guide template mounted on the distal end of the femur.
Figure 33:
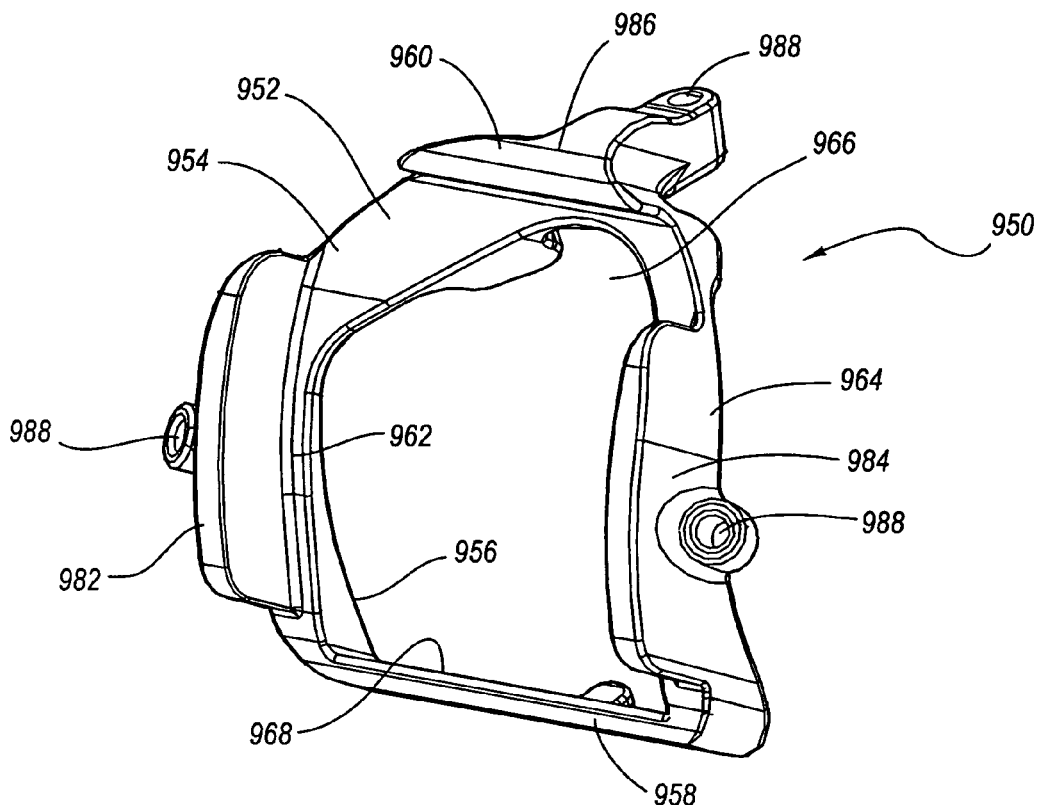
FIG. 33 is a top perspective view of the guide template shown in FIG. 32.
Figure 34:
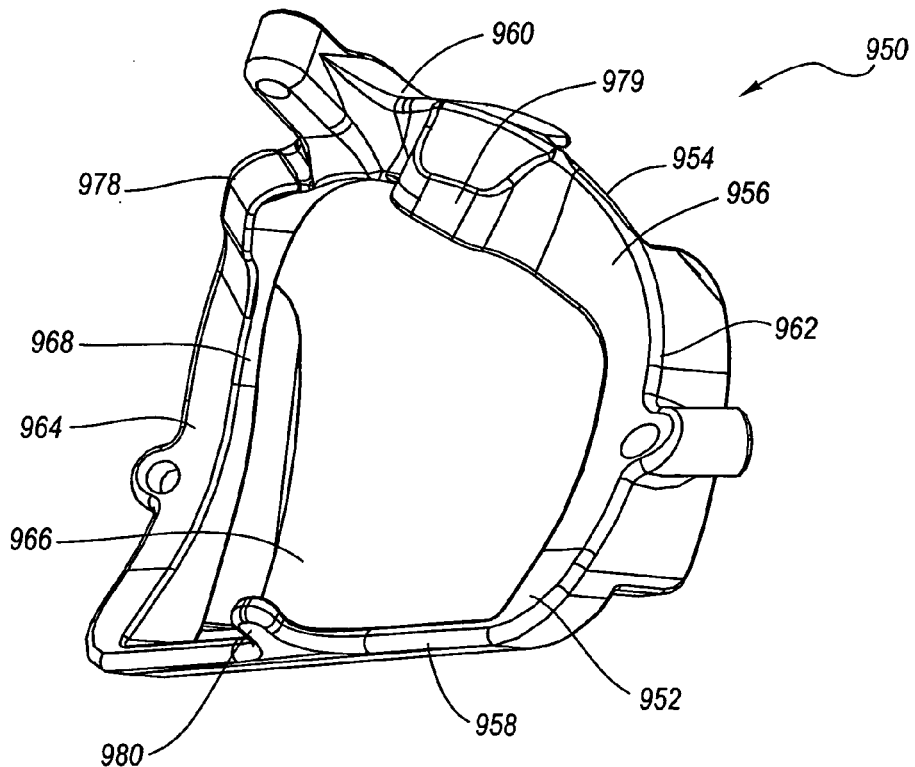
FIG. 34 is a bottom perspective view of the guide template shown in FIG. 32.

The present invention can also be used for mounting a trochlear implant on femur 530. For example, depicted in FIG. 32 is a guide template 950 incorporating features of the present invention. Guide template 950 is mounted on distal end 532 of femur 530 so as to be disposed over at least a portion of trochlear groove 539. As depicted in FIGS. 33 and 34, guide template 950 comprises a body 952 having a top surface 954 and an opposing bottom surface 956. Body 952 also has a proximal end 958 and an opposing distal end 960 which each extend between opposing sides 962 and 964. Top surface 954 has a convex arch or curve that extends between opposing ends 958 and 960 while bottom surface 956 has a concave arch or curve that extends between opposing ends 958 and 960.

Extending through body 952 between top surface 954 and bottom surface 956 is an enlarged opening 966. Opening 966 is configured to overlay the bone which is to be removed so as to form a pocket in which the trochlear implant is received. The portion of the bone that is removed includes all or a portion of the bone forming trochlear groove 539 and, optionally, additional surrounding bone. In one embodiment, opening 966 has or covers an area in a range between about 3 cm$^2$ to about 20 cm$^2$ with about 9 cm$^2$ to about 16 cm$^2$ being more common. Other dimensions can also be used.

It is appreciated that opening 966 can have a variety of different configurations. In the embodiment depicted, opening 966 is bounded by an interior surface 968. As perhaps best depicted in FIG. 32, interior surface 968 comprises two substantially linear side section 972 and 974 that extend between opposing ends 958 and 960 in substantially parallel alignment. A linear proximal section 970 extends between sides sections 972 and 974 at proximal end 958. An arched distal section 976 extends between side sections 972 and 974 and distal end 960. Distal section 976 is asymmetrically arched. As such opening 966 has an asymmetrical configuration. This asymmetry is a result of the irregular anatomical configuration of distal end 932 of femur 530. In alternative embodiments, anterior section 970 can also be arched. Furthermore, in still other embodiments arched posterior section 976 can by symmetrical.

Turning again to FIG. 34, downwardly projecting from bottom surface 956 of body 952 are three spaced apart supports 978, 979, and 980. Supports 978 and 979 are located at or toward distal end 960 while support 980 is located at or toward proximal end 958. Supports 978, 979, and 980 are configured to support body 952 off of femur 530. Specifically, as depicted in FIG. 32, body 952 is supported on femur 530 as a result of support 978 resting against medial conidial 937, support 979 resting against lateral conidial 535, and support 980 resting against anterior side 538, such as within or adjacent to trochlear groove 539.

Because the area surrounding trochlear groove 539 has an irregular configuration, the use of three supports 978-980 provides a stable platform that can be easily designed so as to rest in a stable fashion on a plurality of differently sized and shaped femurs. In alternative embodiments, it is appreciated that the supports can be positioned at different locations on body 952 and can have a variety of different sizes and shapes. Furthermore, fewer or more supports can also be used. For example, guide template 950 can be designed with two supports so that the two supports and a portion of body 952 rest directly against femur 930. In yet other embodiments, four or more supports can be formed projecting from body 952.

As depicted in FIGS. 32 and 33, upwardly projecting from top surface 954 of body 952 is an elongated first guide rail 982 and an elongated second guide rail 984. First guide rail 982 upwardly extends from side 962 while second guide rail 984 upwardly extends from side 964. Guide rails 982 and 984 extend between opposing ends 958 and 960 in substantially parallel alignment and are formed so that a portion of the top surface 952 is openly exposed between each of the guide rails and opening 966. As will be discussed below in greater detail, this portion of top surface 952 is designed for engagement with a rasp. A catch 986 also upwardly projects from top surface 954 at distal end 960.

The present invention also includes means for securing body 952 to femur 530. By way of example and not by limitation, spaced apart mounting holes 988 are formed on or extend through body 952. Screws 990 or other fasteners can be passed through mounting holes 988 so as to secure guide template 950 to femur 930 once guide template 950 is positioned in the desired location. In the embodiment depicted, three mounting holes and screws are used to secure guide template 950. As in prior embodiments, however, alternative numbers of screws and mounting holes or other types of fastening techniques can also be used. Furthermore, the mounting holes 988 can be positioned at a variety of different locations on body 952 and can have a variety of different orientations so as to better stabilize body 952 when the screws are received therein. Likewise, mounting holes 988 are positioned and oriented so that screws 990 only enter the bone outside of the articulation surface, i.e., articular cartilage or on a non-function peripheral edge thereof.

Figure 35:
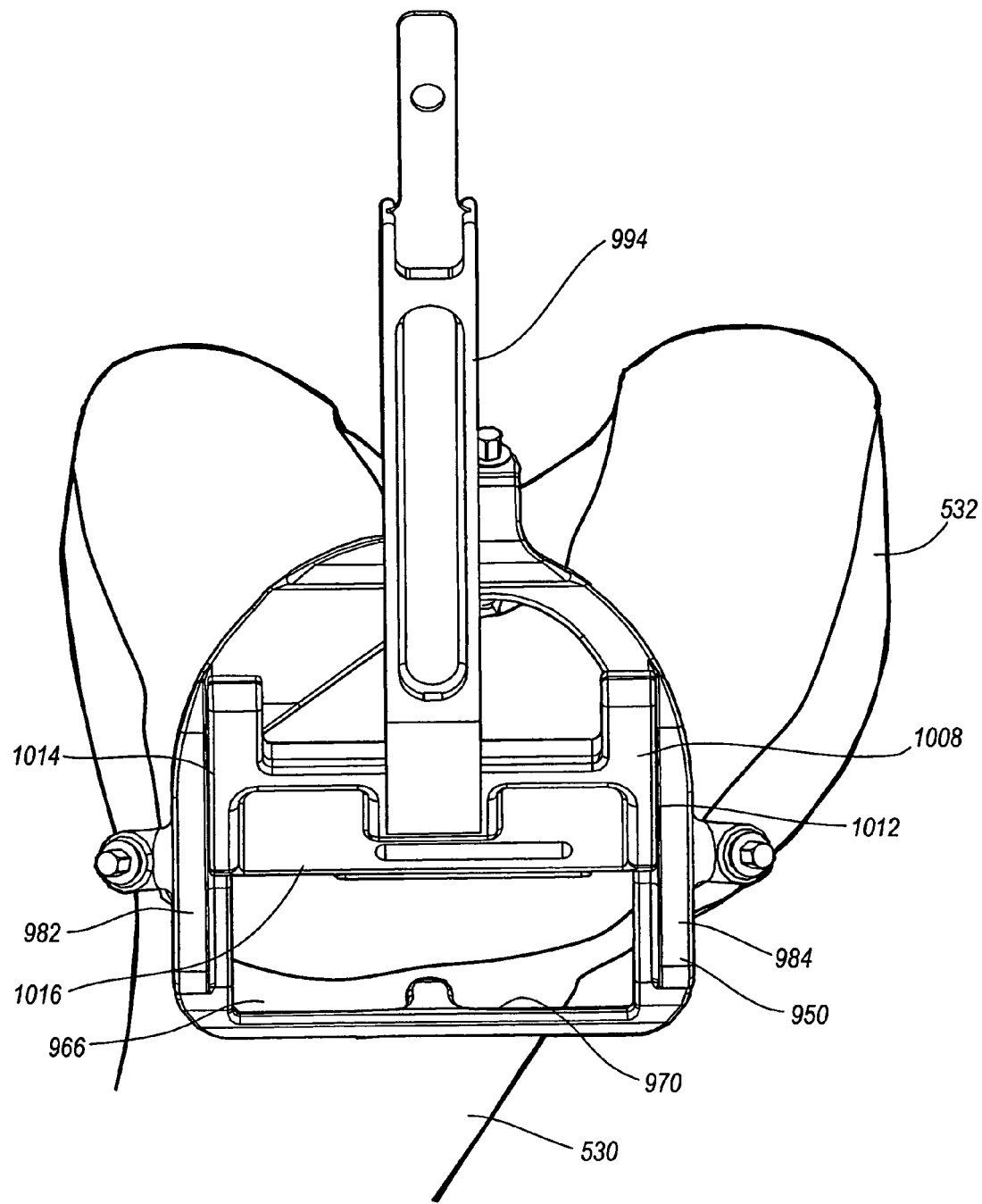
FIG. 35 is a perspective view of the rasp mounted on the guide template show in FIG. 32.
Figure 36:
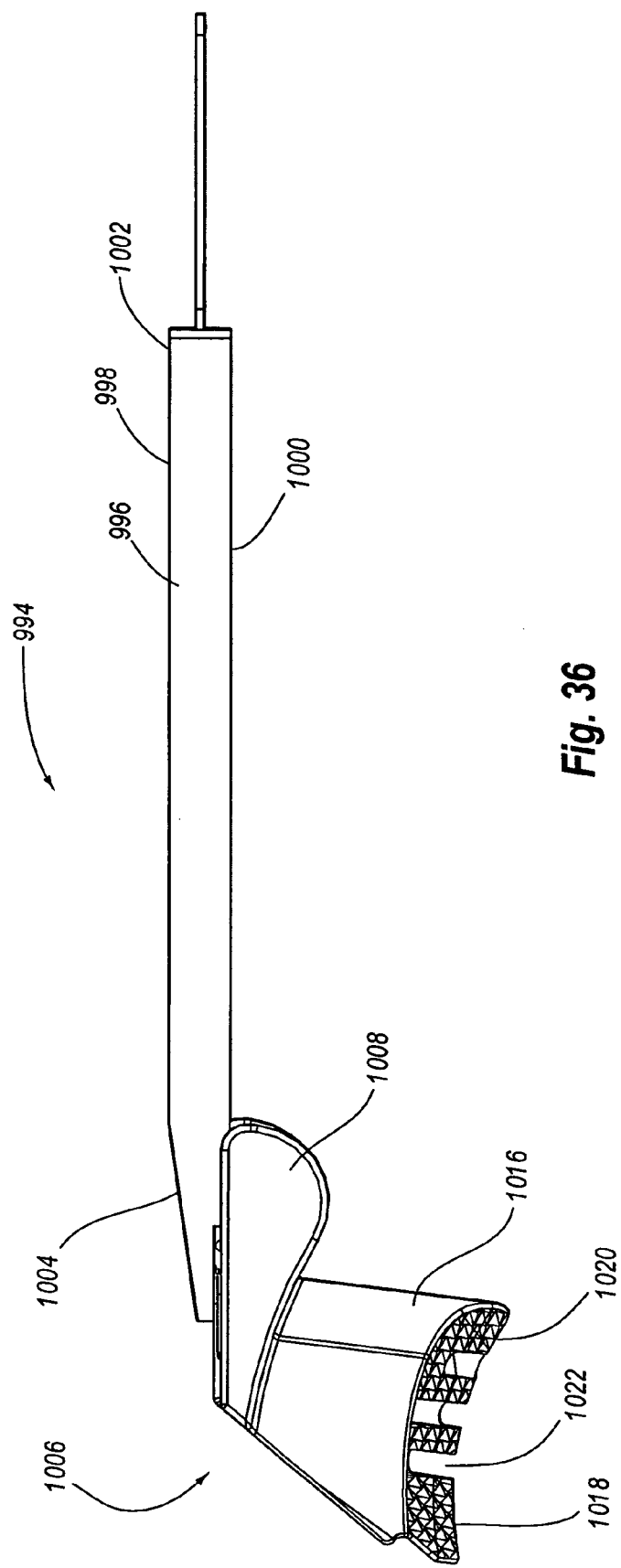
FIG. 36 is an elevated side view of the rasp shown in FIG. 35.
Figure 37:
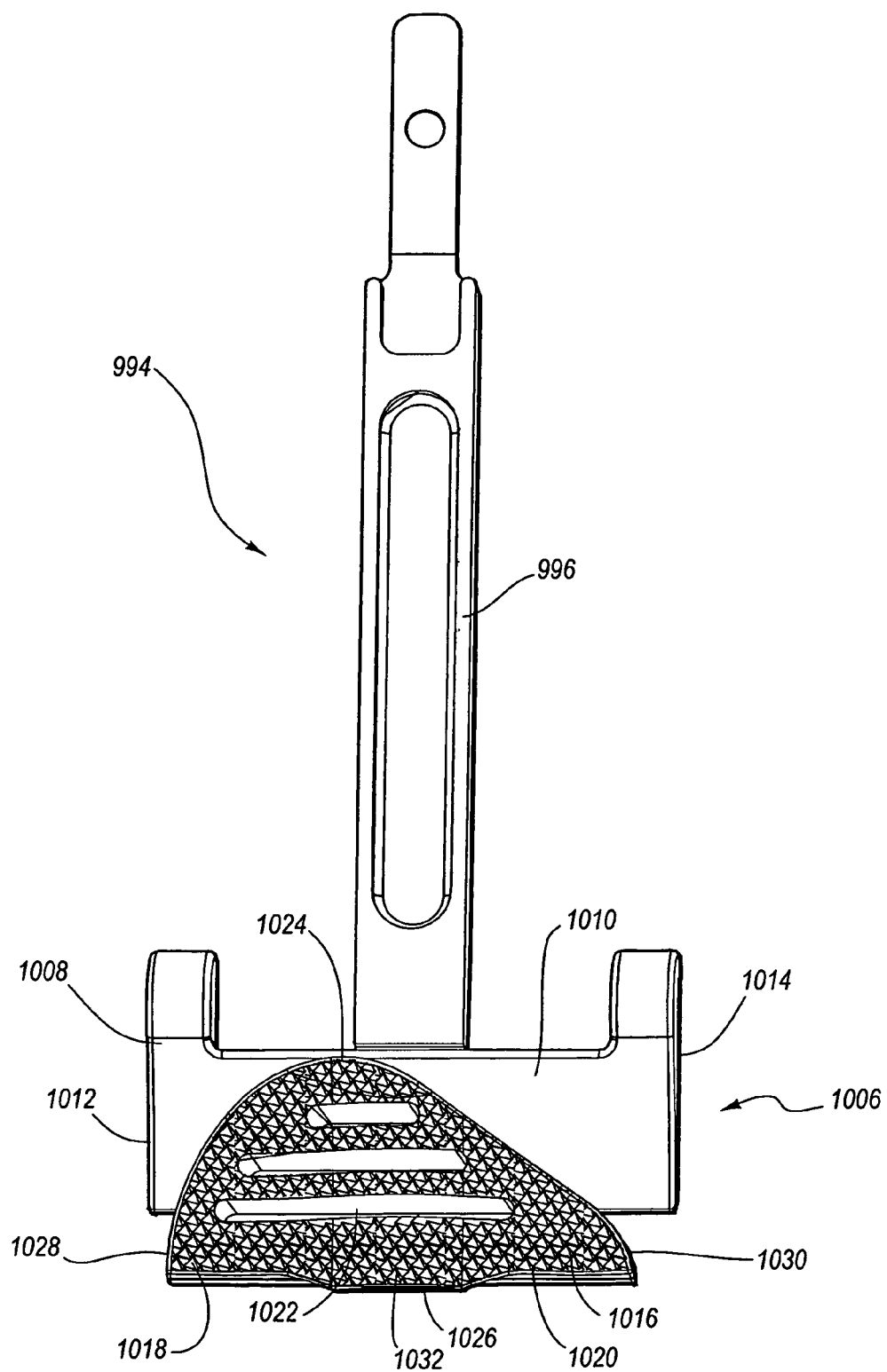
FIG. 37 bottom plan view of the rasp shown in FIG. 35.
Figure 38:
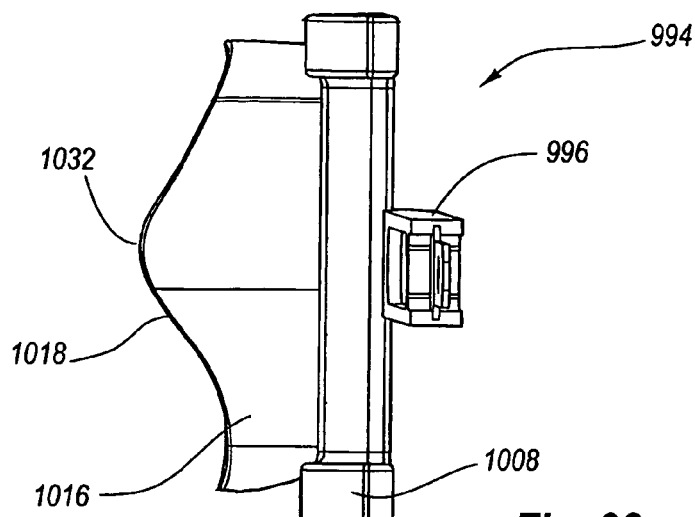
FIG. 38 is an elevated back view of the rasp shown in FIG. 35.

Turning to FIG. 35, once guide template 950 is secured in place, a rasp 994 is used to facilitate resection of the portion of femur 932 bounded by opening 966. As depicted in FIGS. 36-38, rasp 994 comprises an elongated handle 996 having a top surface 998 and an opposing bottom surface 1000 each extending between a first end 1002 and an opposing second end 1004. Mounted at second end 1004 is a head 1006. Head 1006 comprises an elongated slide rest 1008 having a contact surface 1010 extending between a first end face 1012 and an opposing second end face 1014.

Figure 39:
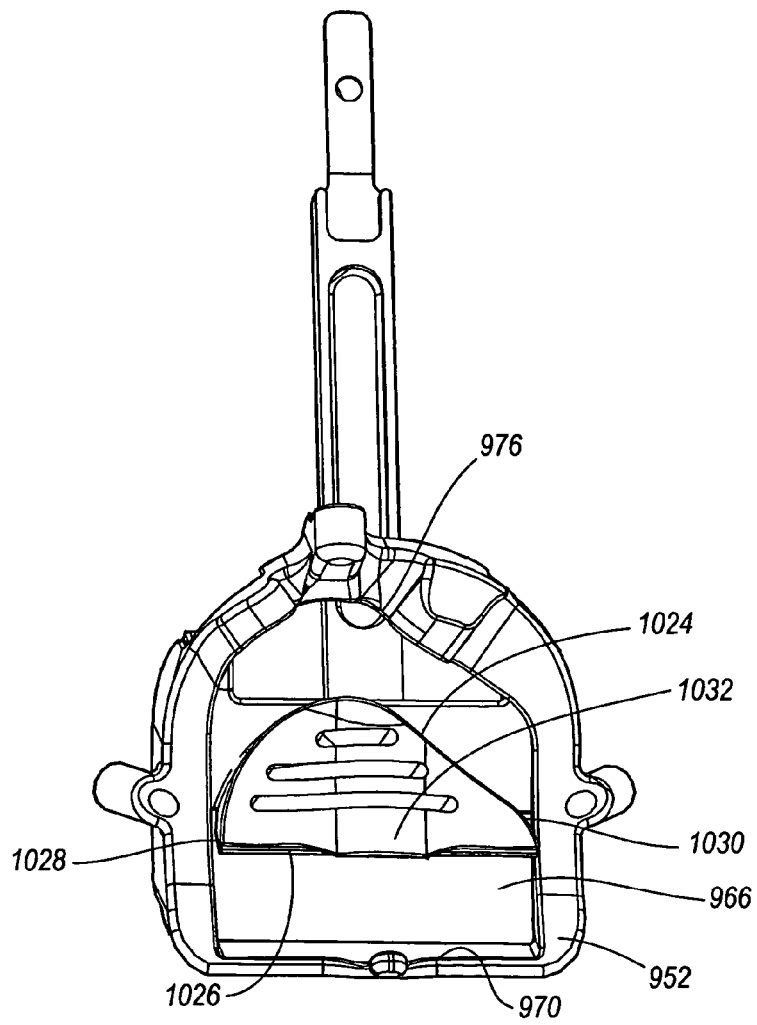
FIG. 39 is a bottom plan view of the rasp and guide template shown in FIG. 35.

Projecting from contact face 1010 of slide rest 1008 is a cutting mount 1016. Cutting mount 1016 comprises a cutting surface 1018 formed by a plurality of cutting teeth 1020. (It is noted that in FIGS. 38, 39, 41, 51 52, and 58 that cutting teeth 1020 have been removed for ease in illustration.) A plurality of channels 1022 extend through cutting mount 1016 and facilitate removal of bone fragments that are resected by a rasp 994. As shown in FIG. 37, cutting mount 1016 has a proximal end 1024 and an opposing distal end 1026 which each extend between opposing sides 1028 and 1030. The distance between opposing sides 1028 and 1030 is substantially equal to the width of opening 966 of guide template 950. Turning to FIG. 39, distal end 1026 is generally linear and is complementary to proximal section 970 of body 952 bounding opening 966. Likewise, proximal end 1024 is asymmetrically arched and is complementary to distal section 976 of body 952 bounding opening 966.

As depicted in FIGS. 37 and 38, cutting surface 1018 comprises a rounded, outwardly projecting ridge 1032 that extends between proximal end 1024 and distal end 1026 at a location substantially central between opposing sides 1028 and 1030. Furthermore, as depicted in FIG. 36, cutting surface 1018, including ridge 1032, is curved along its longitudinal axis in a concave arch that curves away from handle 996. This figure also shows ridge 1032 having an apex extending along the length thereof having a concave arch.

During operation as depicted in FIG. 35, cutting mount 1016 of rasp 994 is received within opening 966 of guide template 950 such that opposing side faces 1012 and 1014 of slide rest 1008 are disposed between and adjacent to guide rails 984 and 982, respectively. The interaction between guide rails 984, 982 and slide rest 1008 limits and guides the movement of cutting mount 1016 in a linear path between the opposing ends of opening 966. First end 1002 of handle 996 is coupled with a reciprocating driver so to facilitate rapid reciprocating of cutting mount 1016 within opening 966. Reciprocating cutting surface 1018 of cutting mount 1016 against the portion of femur 530 bounded by opening 966 progressively removes the bone by rasping. As the bone is progressively removed by teeth 1020, cutting mount 1016 continues to descend within opening 996 until the opposing ends of slide rest 1008 rest against top surface 954 of body 952 on opposing sides of opening 966.

Figure 40:
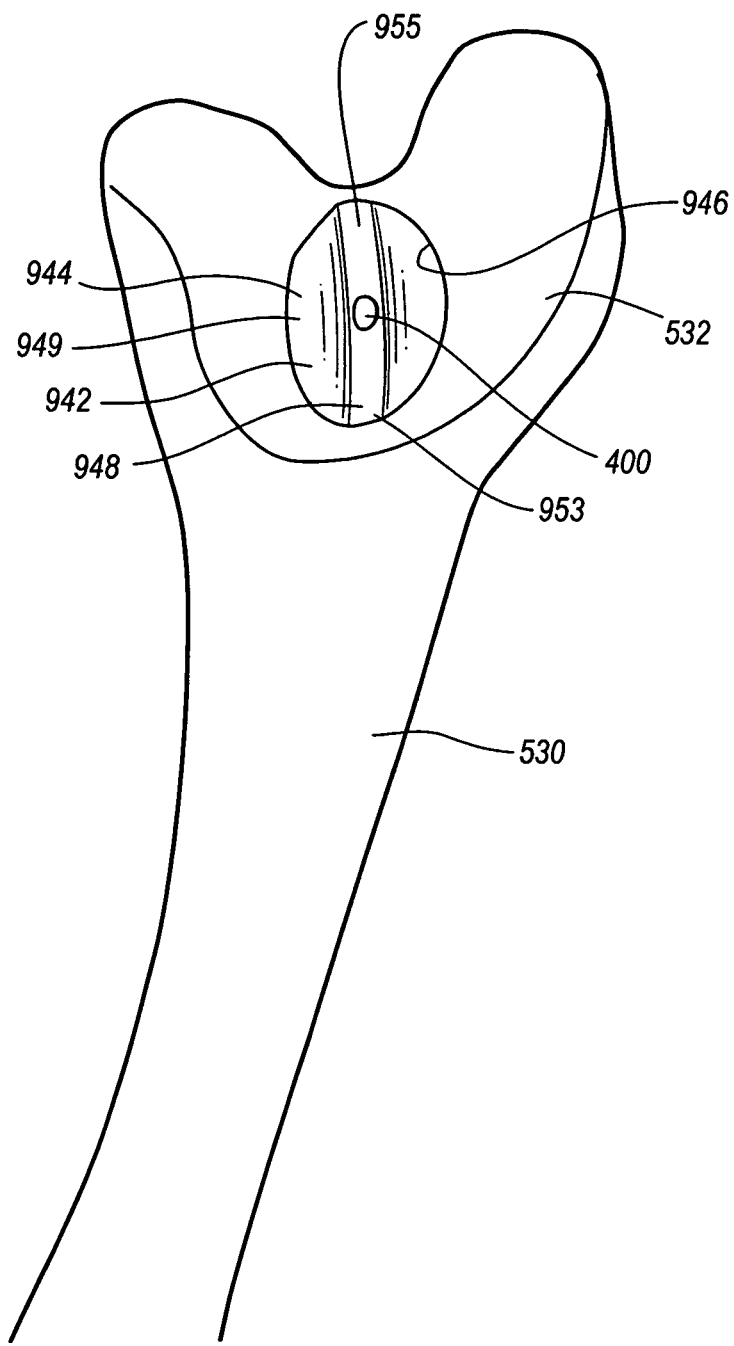
FIG. 40 is a perspective view of the femur shown in FIG. 35 having a recessed pocket formed by the rasp.

Once slide rest 1008 reaches top surface 954, the bone has been removed to the desired depth. Here it is noted that the curvature of top surface 954 causes rasp 994 to move in a curved path as slide rest 1008 slides along top surface 954. Rasp 994 is then removed so as to reveal, as depicted in FIG. 40, a recessed pocket 942. Pocket 942 is bounded by a floor 944 having an encircling side wall 946 upstanding around the perimeter thereof. Pocket 942 has opposing sides 949 and 951 that extend between a proximal end 953 and an opposing distal end 955.

Due to the configuration of cutting mount 1016, a rounded, elongated channel 948 is recessed along floor 944 in substantial alignment with where trochlear groove 539 was previously disposed. That is, channel 948 extends between opposing ends 953 and 955. Floor 944 also has a convex curvature that extends between opposing ends 953 and 955. As will be discussed below in greater detail, the configuration of recessed pocket 942 enables the formation of a low profile trochlear implant having substantially uniform thickness. Furthermore, the formation of pocket 942 produces a stable platform for the implant having a complementary configuration.

Figure 41A:
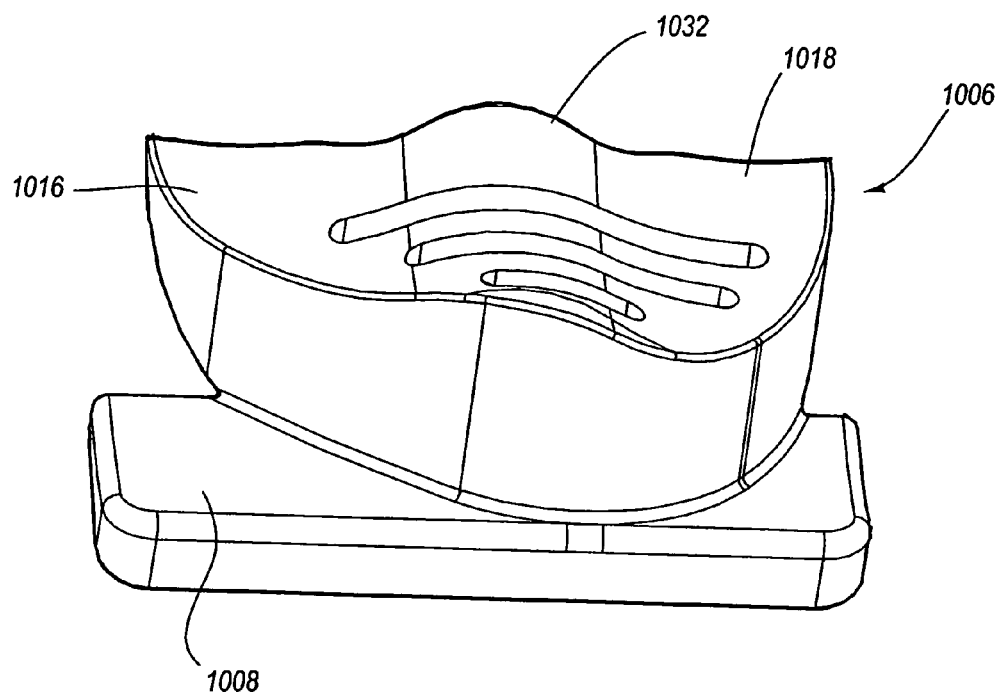
FIG. 41A is a back perspective view of the cutting mount for the rasp shown in FIG. 36.
Figure 41B:
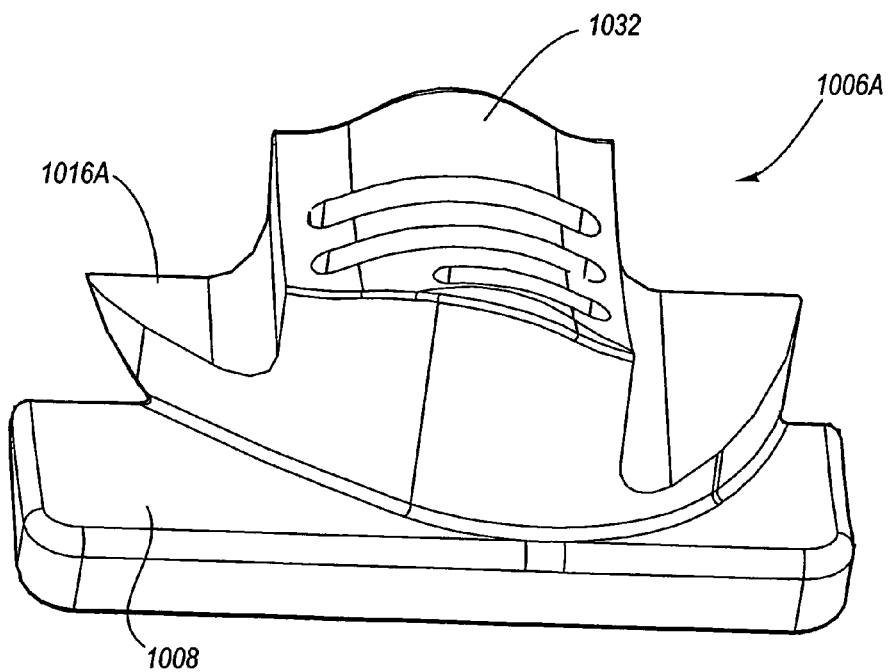
FIG. 41B is a back perspective view of an alternative embodiment of the cutting mount shown in FIG. 41A.

In one alternative embodiment, it is appreciated that recessed pocket 942 can be formed by using two or more different rasps. For example, instead of trying to remove all of the bone material using a single rasp, a smaller rasp can initially be used to form channel 948 within recessed pocket 942. By way of an illustrated example, depicted in FIGS. 41A and 41B are cutting head 1006, as previously discussed, and a cutting head 1006A, respectively. Cutting head 1006A comprises slide rest 1008 and a cutting mount 1016A projecting therefrom. Cutting mount 1016A is substantially the same as cutting mount 1016 except that cutting surface 1018 has been resected on each side of ridge 1032. As a result, cutting head 1006A can initially be used to form channel 948 of recessed pocket 942. Cutting head 1006 can then be used to remove the rest of the bone so as to form recessed pocket 942. It is appreciated that any number of different rasps can be configured to removed different portions of recessed pocket 942.

Figure 42:
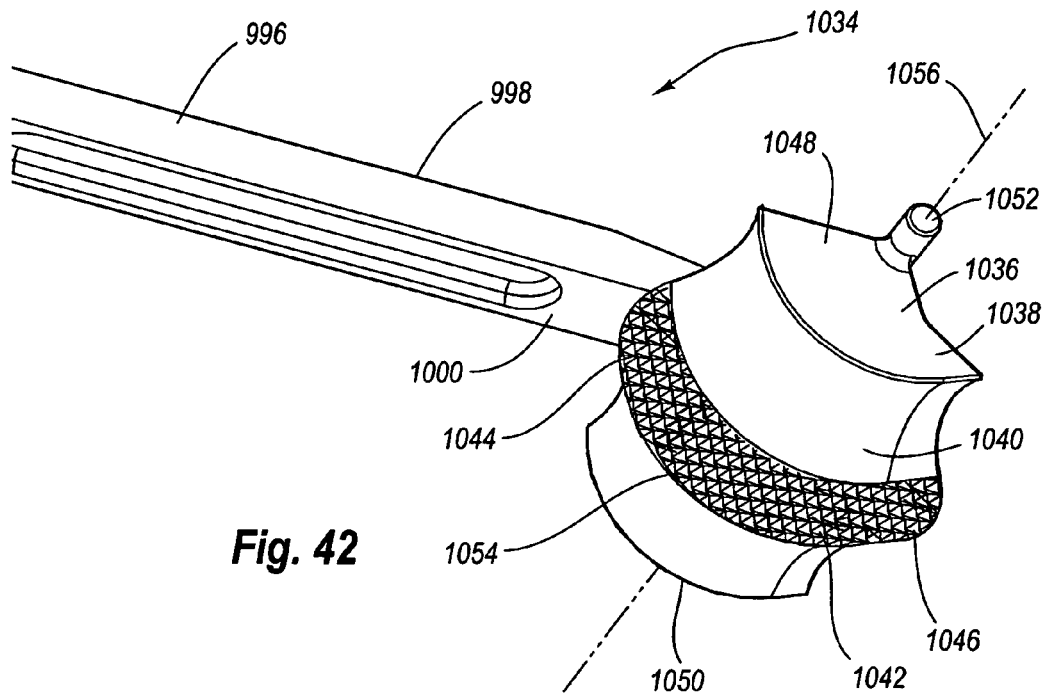
FIG. 42 is an alternative embodiment of a rasp.

Depicted in FIG. 42 is another alternative embodiment of a rasp 1034 incorporating features of the present invention. Rasp 1034 comprises handle 996 as previously discussed and a cutting head 1036 mounted on the end thereof. Cutting head 1036 comprises a cutting mount 1038 having a cutting surface 1040 comprised of a plurality of cutting teeth 1042. Cutting surface 1040 has a proximal end 1044 and an opposing distal end 1046 which each extend between opposing side faces 1048 and 1050. (For ease in illustration, cutting teeth 1042 have only been depicted on the central portion of cutting surface 1040. Cutting teeth actually extend over all of surface 1040 between side faces 148 and 1050.) In one embodiment, opposing ends 1048 and 1046 have a length in a range between about 1.5 cm to about 6 cm with about 2 cm to about 4 cm being more common. Other dimensions, however, can also be used. Outwardly projecting from each side face 1048 and 1050 is a corresponding slide rest 1052. In this embodiment, each slide rest 1052 rounded, such as by having a substantially cylindrical configuration.

Cutting surface 1040 substantially comprises a surface of rotation which curves between proximal end 1044 and distal end 1046 about a common rotational axis 1056. Of course, the surface of rotation has some variation due to the fact that it is formed from the plurality of teeth 1042. In one embodiment, cutting surface 1040 can extend about axis 1056 over an angle greater that 300°. More commonly however, cutting surface 1040 extend over an angle in a range between about 15° to about 180° with about 25° to about 100° being more common. Other angles can also be used.

Cutting surface 1040 is also depicted as having a non-linear contour when viewed in a plane extending between side faces 1048 and 1050 and intersection with rotational axis 1056 along the length thereof. Specifically, cutting surface 1040 has a rounded, outwardly projecting ridge 1054 which extends between opposing ends 1044 and 1046 substantially centrally between opposing side faces 1048 and 1050. Ridge 1054 is used to form channel 948 of recessed pocket 942. It is appreciated that rasp 1034 can be used to form recessed pockets for other types of implants and that in such alternative uses, the contour of cutting surface 1040 can have a variety of different configurations.

Rasp 1034 is configured so that cutting mount 1038 can be disposed within opening 966 of guide template 950 so that as rasp 1034 is reciprocated, cutting surface 1040 reciprocates against the bone surface. In turn, teeth 1042 on cutting surface 1040 progressively resect the bone surface until slide rests 1052 bear against top surface 954 of guide template 950. Rasp 1034 can thus also be used to form recessed pocket 942 having channel 948. One of the benefits of rasp 1034 is that because of the unique configuration of cutting surface 1040, cutting surface 1040 can be rotated or positioned at any desired angle about axis of rotation 1056 and still produce recessed pocket 942 having the same contour. As a result, the operator of rasp 1034 is able to selectively position or repeatedly position the orientation of handle 996 for the most convenient orientation of reciprocating without jeopardizing the desired configuration for recessed pocket 942.

During the rasping process, it is noted that the rasp can cause slight vibration or movement of guide template 950 which is typically formed from a metal or other rigid material. In turn, this movement can cause supports 978 and 979, which are typically integrally formed with body 952, to wear against the articulation surface. To prevent unwanted wear, flexible pads can be positioned between supports 978 and 979 and the articulation surface. In other embodiments, all or portions of the supports 978 and 979 can be formed from a flexible material that will not damage the articulation surface. Such flexible materials can comprise a polymeric or rubber material. In yet other embodiments as discussed below in greater detail, the supports can be removed during the rasping process to as to avoid damage to the articulation surface.

Once recessed pocket 942 is finished, the rasp is removed and tunnel 400 is formed extending from pocket 942 to a location spaced apart from the articulation surface, such as the lateral or medial side of femur 530. As disclosed in various embodiments depicted in the '941 application, guide template 950 can be used in association with a centering template and tunnel guide to facilitate formation of tunnel 400. In an alternative embodiment, it is again appreciated that the centering template and tunnel guide can be eliminated. That is, tunnel 400 can be drilled after removal of guide template 950 by starting at recessed pocket 942 and extending to the lateral or medial side of the femur 530. Because it is less critical where tunnel exits on the lateral or medial side, a tunnel guide is not required but could, if desired, still be used.

Figure 43:
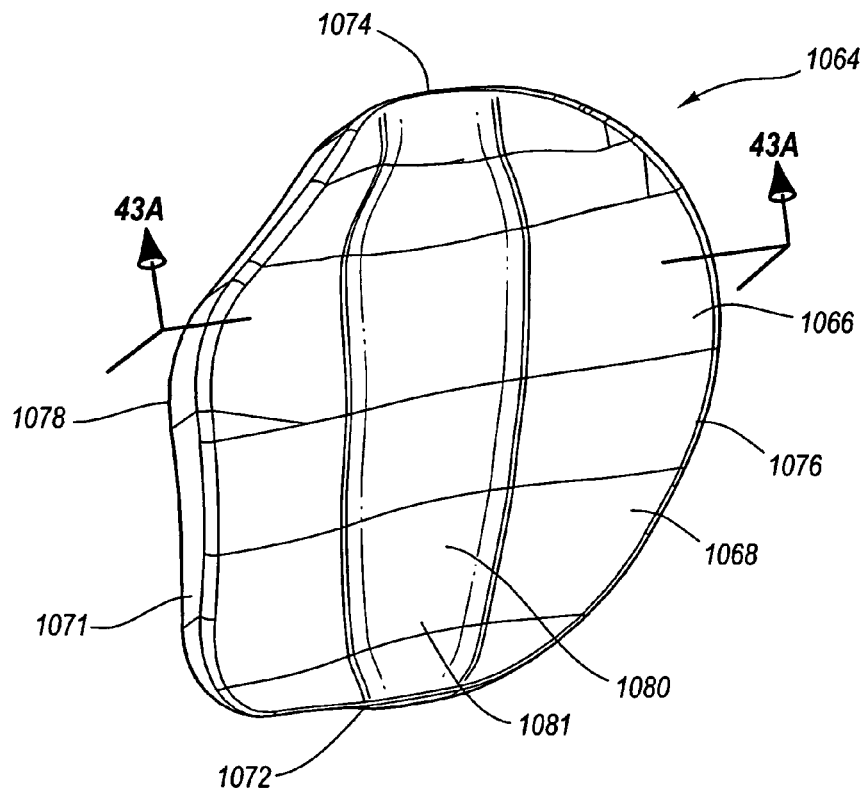
FIG. 43 is a top perspective view of a trochlear groove implant with FIG. 43A being a cross section thereof.
Figure 44:
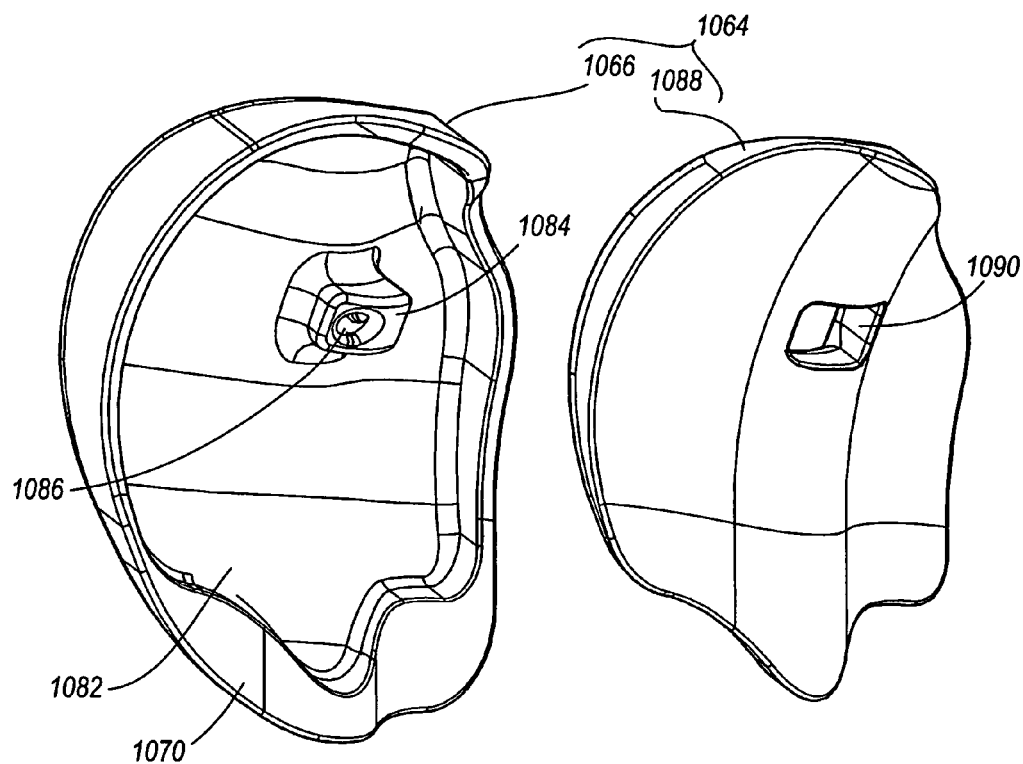
FIG. 44 is a back perspective view of the trochlear groove implant shown in FIG. 43 in a disassembled state.

Once tunnel 400 is formed, a trochlear implant is then secured within the recessed pocket 942. Depicted in FIGS. 43 and 44 is one embodiment of a trochlear implant 1064 incorporating features of the present invention. Trochlear implant 1064 comprises a body 1066 having an articular surface 1068 and an opposing bottom surface 1070 that each extend to a perimeter edge 1071. Body 1066 is further defined as having an proximal end 1072 and a distal end 1074 each extending between a lateral side 1076 and a medial side 1078. Articular surface 1068 is formed having an elongated channel 1080 extending between proximal end 1072 and distal end 1074 substantially centrally between sides 1076 and 1078. Channel 1080 forms a least a portion of the resurfaced trochlear groove in which the patella rides.

Figure 43A:
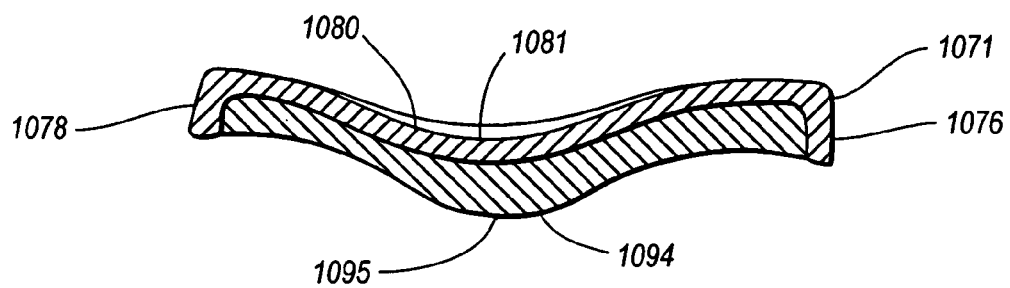

In one embodiment viewed in a plane extending between sides 1076 and 1078 (FIG. 43A), channel 1080 has a bottom 1081 with a concave curvature. The surfaces extending from the concave curvature at bottom 1081 to perimeter edge 1071 at each side 1076 and 1078 are typically not concave. Rather, these surfaces are typically substantially flat so as to form a substantially V-shaped transverse cross section with rounded bottom or have a substantially convex curvature. It is also appreciated that articular surface 1068 has a smooth continuous convex curvature that extends between opposing ends 1072 and 1074.

Depicted in FIG. 44, formed on bottom surface 1070 is a pocket 1082. It is appreciated that flexible line 438 can be secured to trochlear implant 1064 using any of the techniques previously discussed. In the embodiment depicted, a post 1084 projects from within pocket 1082. A constricting passage 1086 extends through post 1084 and is configured to hold flexible line 438 such as previously discussed. Secured within pocket 1082 is an inlay 1088 of a porous bone ingrowth material. Inlay 1088 has an opening 1090 formed thereon through which post 1084 extends.

As depicted in FIG. 45, bottom surface 1070 and inlay 1088 combine to form a bone apposition surface 1092 of trochlear implant 1064. Bone apposition surface 1092 has a configuration complementary to the formation of the recessed pocket 942 formed on femur 530. Bone apposition surface 1092 also typically has a configuration complementary to articular surface 1068. Specifically, bone apposition surface 1092 is formed having a rounded, outwardly projecting ridge 1094 that extends between proximal end 1072 and distal end 1074, substantially centrally between sides 1076 and 1078. When viewed in a plane extending between sides 1076 and 1078 (FIG. 43A), ridge 1094 terminates at an apex 1095 having a convex curvature. The side surfaces of ridge 1094 extending to sides 1076 and 1078 are typically substantially flat or have a concave curvature.

Ridge 1094 is typically aligned with channel 1080 so that trochlear implant 1064 can have a substantially uniform thickness. For example, in one embodiment bone apposition surface 1092 can be substantially complementary to articular surface 1068 so that implant 1064 has a substantially uniform thickness between surfaces 1068 and 1092. In other embodiments, implant 1064 may be slightly tapered along perimeter edge 1071. Thus, at all locations at least 2 mm in from the perimeter edge 1071, body 1066 has a thickness extending between the bone apposition surface 1092 and the articular surface 1068 that does not vary by more than 30%, 20%, or more commonly 15%. Other percentages can also be used. The actual thickness depends on the desired implant and is typically in a range between about 3 mm to about 10 mm.

Ridge 1094 is also configured to be complementarily received within channel 948 formed on recessed pocket 942. Bone apposition surface 1092 thus also has a continuous concave curvature extending between opposing ends 1072 and 1074. Because of the unique method in which pocket 942 can be formed, bone apposition surface 1092 can be formed having a smooth surface with no stepped shoulders or corners as required in many conventional implants. Implant 1064 can also be modified in the same manner as the other implants disclosed herein. For example, spikes or other forms of projections can be formed projecting from bone apposition surface 1092.

Because implant 1064 is configured to fit within pocket 942, implant 1064 has an outer perimeter having an asymmetrical configuration. In one embodiment, articular surface 1068 of implant 1064 has a centroidal location. Articular surface 1068 has a maximum radius extending from the centroidal location to perimeter edge and a minimum radius extending from the centroidal location to the perimeter edge, the minimum radius not being less than 70% and more commonly not being less than 80% of the maximum radius. Other dimensions can also be used. It is also appreciated that the alternatives as previously discussed with regard to implant 300 are also applicable to implant 1064.

Figure 46:
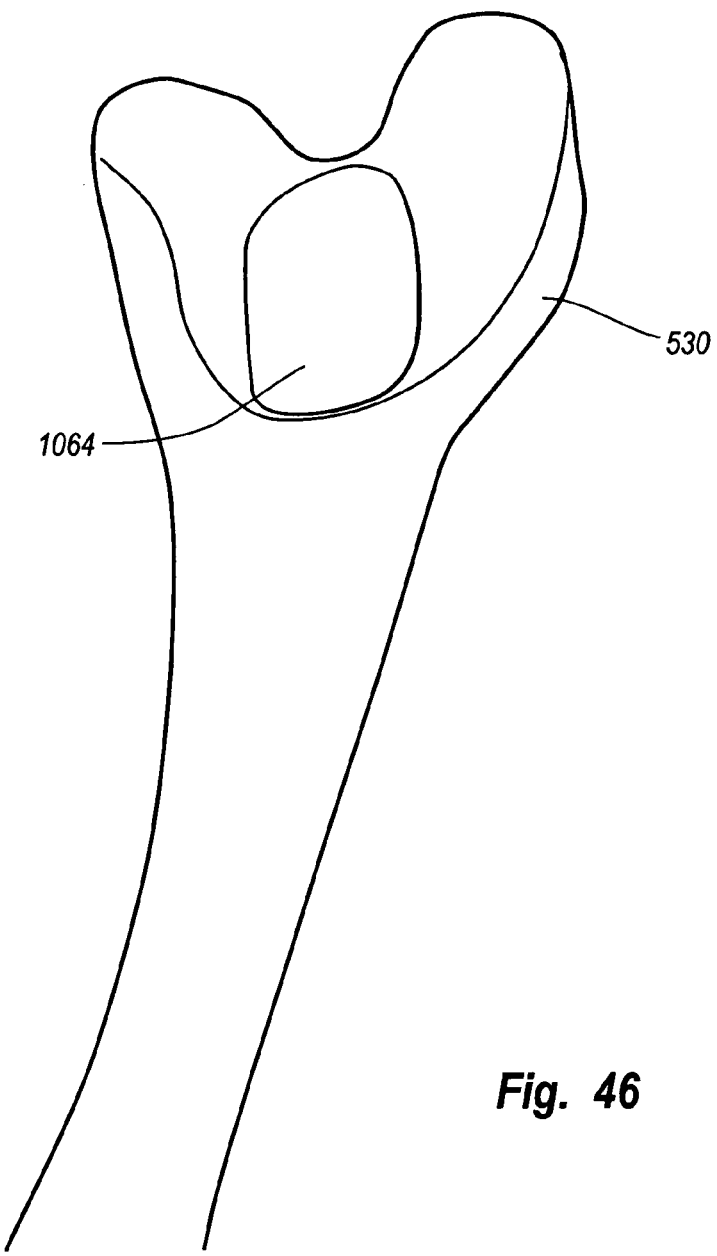
FIG. 46 is a perspective view of the femur shown in FIG. 40 with the implant shown in FIG. 43 mounted in the pocket thereof.

Turning to FIG. 46, trochlear implant 1064 is secured within recessed pocket 942 of femur 530 using anchor assembly 810 (FIG. 15) and the instruments and techniques as previously discussed with regard to FIGS. 15-25. The same alternatives as previously discussed with regard to FIGS. 15-25 are also applicable to the attachment of trochlear implant 1064. For example, two separate tunnels can be formed on femur 530 that intersect with the recessed pocket 942. Opposing ends of a single line 438 slidably connected to trochlear implant 1064 can be passed through the separate tunnels and secured with corresponding bone anchors. Alternatively, two separate and discrete lines 438 can be connected to trochlear implant 1064, each line being disposed in a separate tunnel. Likewise, other means can also be used to secure implant 1064 to femur 530 such as those disclosed in U.S. patent application Ser. No. 10/798,665 which was previously incorporated by reference.

Figure 47:
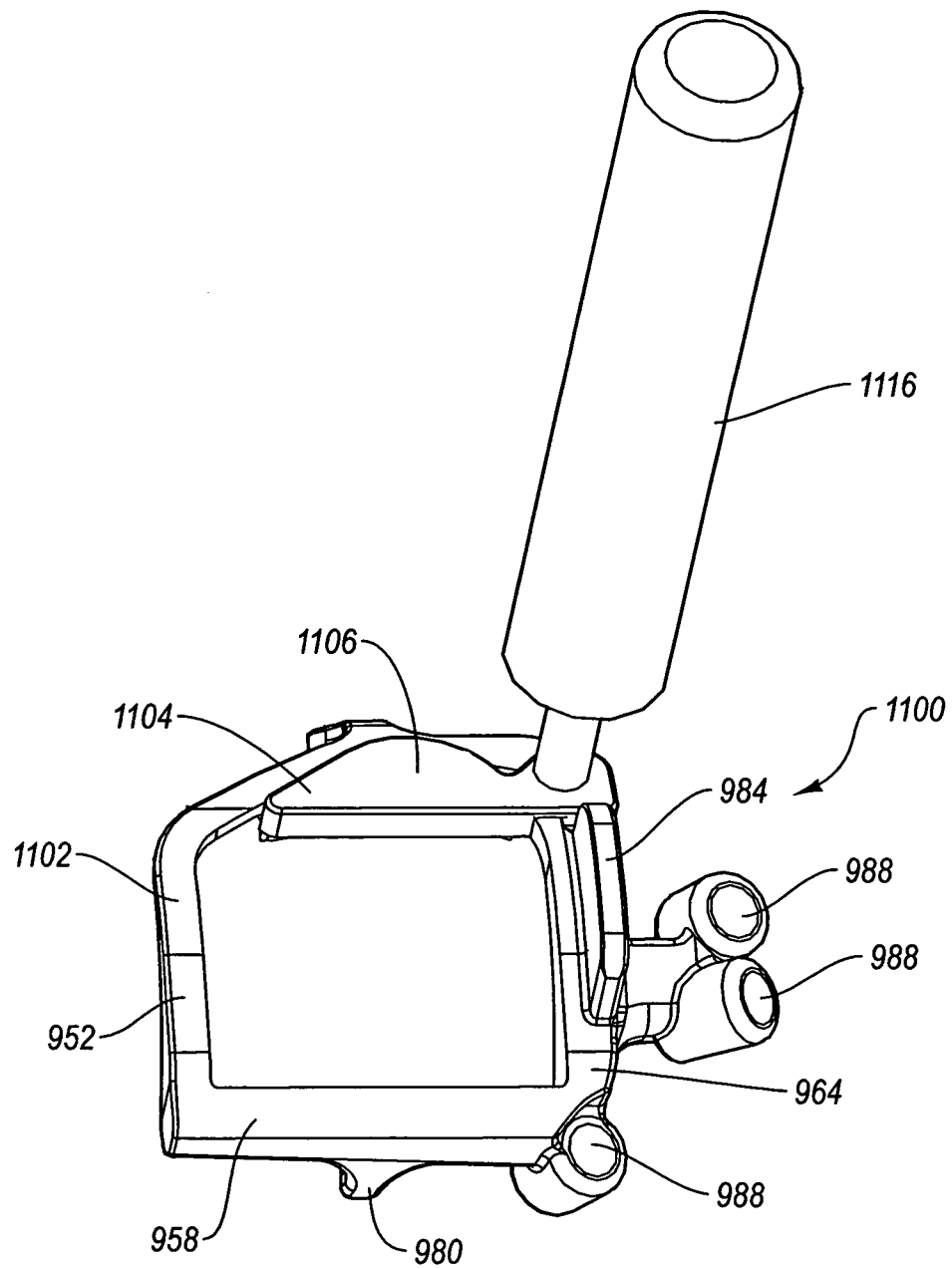
FIG. 47 is a top perspective view of an alternative embodiment of the guide template shown in FIG. 32.

Depicted in FIG. 47 is an alternative embodiment of a guide template 1100 which can be used for forming pocket 942 to receive trochlear implant 1064. Like elements between guide templates 950 and 1100 are identified by like reference characters. In contrast to guide template 950 where the supports are shown integrally formed with the body, guide template 1100 comprises a modular template. Specifically, guide template 1100 comprises a base 1102 and a mount 1104 removable connected to base 1102.

Base 1102 comprises body 952, as previously discussed, having support 980 projecting from proximal end 958. First guide rail 982 has been eliminated but second guide rail 984 still upwardly projects from top surface 952 at side 964. As will be discussed below in greater detail, three mounting holes 988 are formed on side 964 while one mounting hole 988 is formed at distal end 960. A coupling hole 1103 (FIG. 49) is also formed on body 952 at or toward distal end 960.

Figure 48:
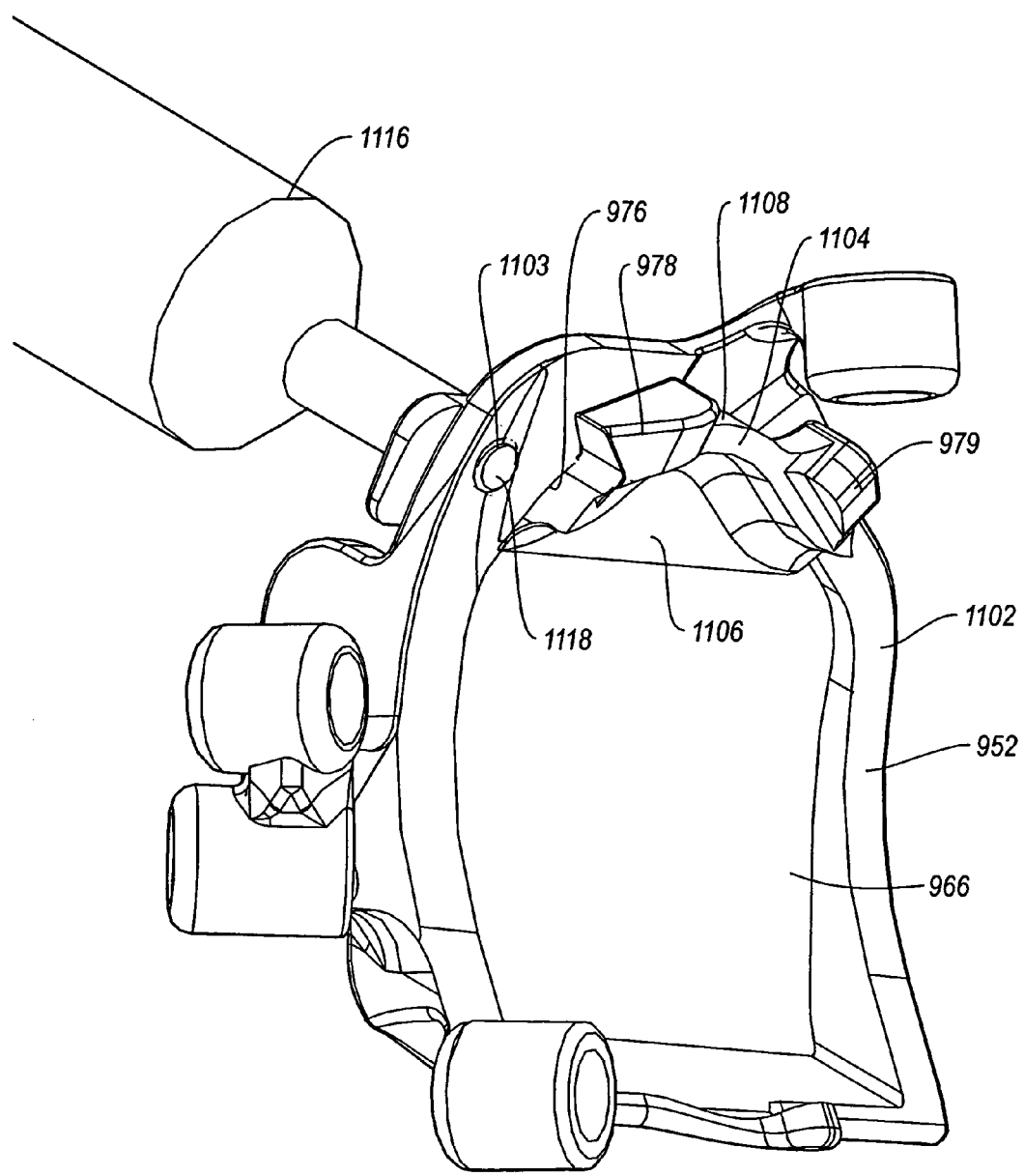
FIG. 48 is a bottom perspective view of the guide template shown in FIG. 47.
Figure 49:
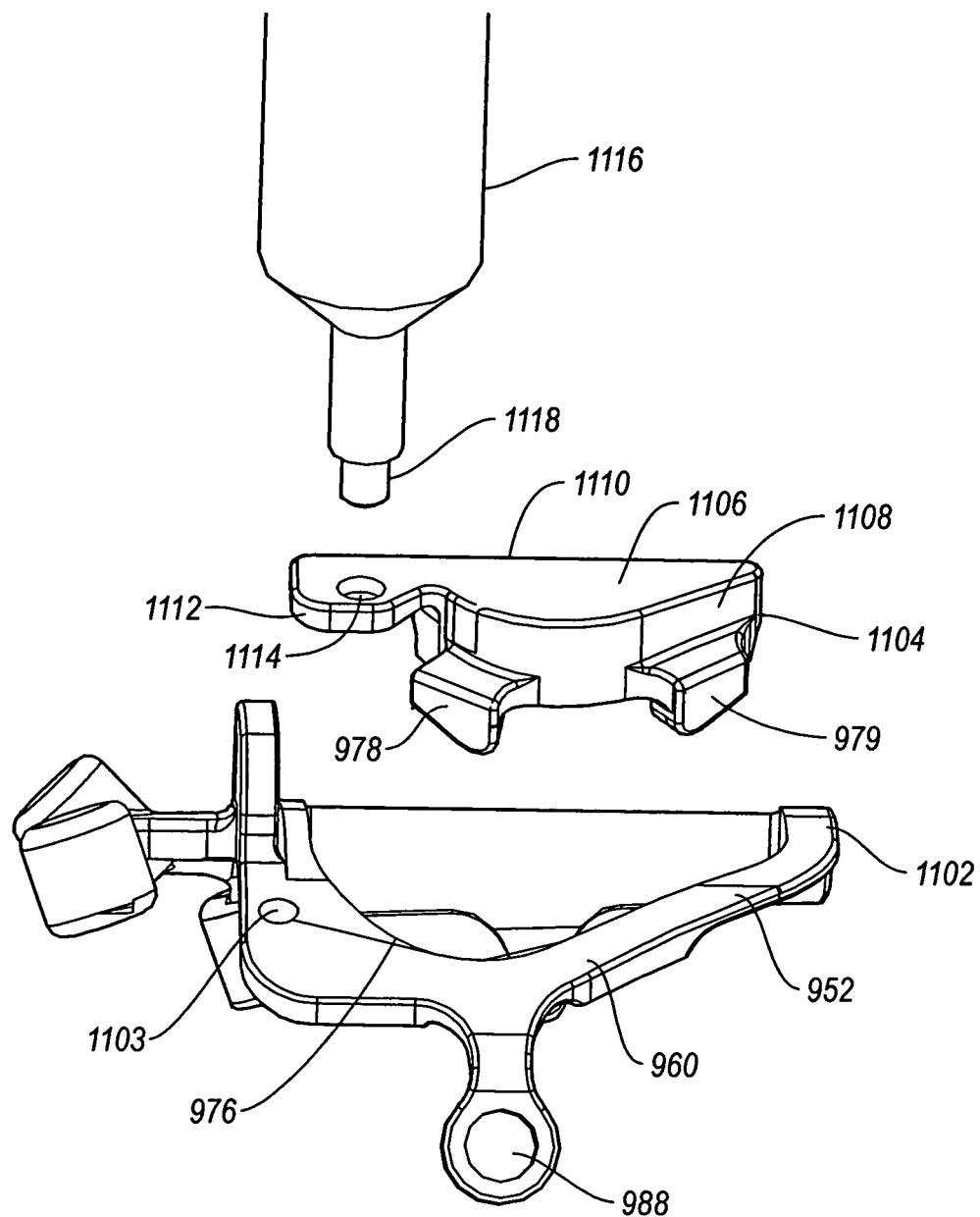
FIG. 49 is a disassembled view of the guide template shown in FIG. 47.

As depicted in FIG. 49, mount 1104 comprises a brace 1106 having a front face 1108 and a back face 1110. Front face 1108 has a contour complementary to distal section 976 of body 952. Projecting forward and down from front face 1108 are supports 978 and 979. A flange 1112 also projects out from brace 1106 and has a coupling hole 1114 extending therethrough. As depicted in FIGS. 47 and 48, mount 1104 is removably coupled with base 1102 by positioning front face 1108 of mount 1104 against distal section 976 of body 952 so that supports 978 and 979 extend below body 952. In this position, coupling holes 1103 and 1114 are aligned. A threaded tip 1118 of a handle 1116 is screwed into coupling holes 1103 and 1114 so as to selectively secure base 1102 and mount 1104 together. It is appreciated that any number of alternative fastening techniques can be used to selectively secure base 1102 and mount 1104 together.

Figure 50:
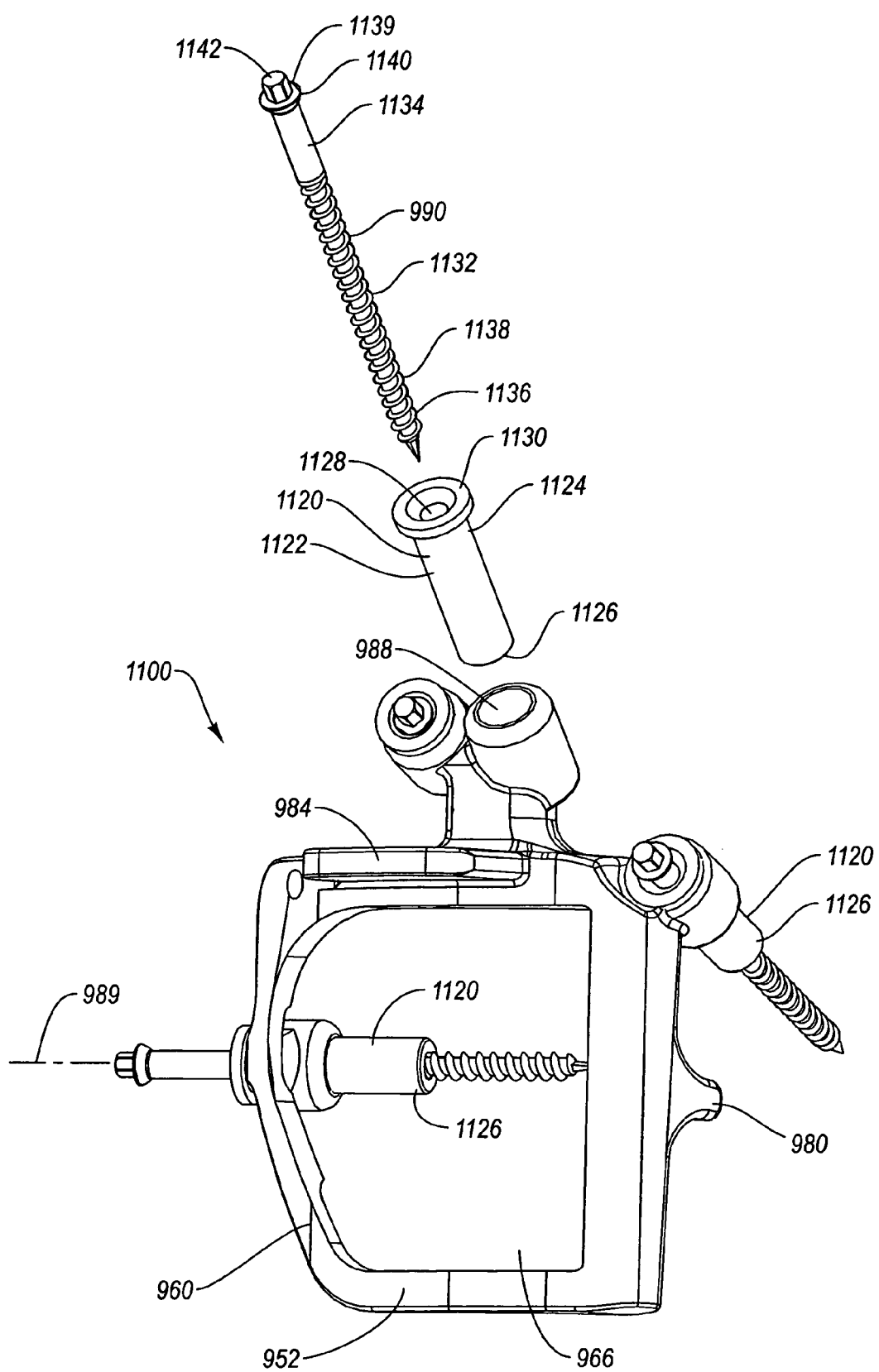
FIG. 50 is a perspective view of the base of the guide template shown in FIG. 46 with guide sleeves and screws.

In the above assembled configuration, guide template 1100 is positioned onto the distal end of femur 530 in substantially the same orientation as previously discussed with regard to FIG. 32. That is, supports 978 and 979 are positioned directly on the articulation surface of femur 530 so that guide template 1100 is stably supported thereon. A plurality of guide sleeves and screws or other fasteners are then use to secure guide template 1100 onto femur 530. Specifically, as depicted in FIG. 50, implant 1100 also comprises a tubular guide sleeve 1120 for each mounting hole 988. Each guide sleeve 1120 comprises a tubular stem 1122 having, a first end 1124 and an opposing second end 1126. A passage 1128 centrally extends through stem 1122 between opposing ends 1124 and 1126. A circular flange 1130 encircles and radially outwardly projects from first end 1124. Each guide sleeve 1120 is configured so that second end 1126 can be received within and slid through a corresponding mounting hole 988. Flange 1130 is larger than mounting hole 988 and thus functions as a stop.

Each screw 990 comprises an elongated shaft 1132 having a first end 1134 and an opposing second end 1136. Threads 1138 are formed on second end 1136 while an enlarged head 1139 is formed at first end 1134. In the embodiment depicted, enlarged head 1139 comprises a flange 1140 that encircles and radially outwardly projects from first end 1134. An engagement head 1142 extends above flange 1140 and has a polygonal or non-circular cross section so that a driver can be connected to engagement head 1142 for selective rotation of screw 990. It is appreciated that enlarged head 1139 of screw 990 can come in a variety of different configuration. For example, enlarged head 1139 can be formed with a socket, slot(s) or other engaging surfaces to engage with other types of drivers. Each screw 990 is configured so that second end 1136 can be received within and slid through a corresponding passage 1128 of a guide sleeve 1120. Enlarged head 1139 is larger than passage 1128 and thus functions as a stop.

During mounting of guide template 1100, guide template 1100 with mount 1104 secured to base 1102 is positioned on the distal end of femur 530 in the same orientation as depicted in FIG. 32 so that opening 966 is disposed over at least a portion of trochlear groove 539. Each guide sleeve 1120 is positioned within a corresponding mounting hole 988 either before or after positioning guide template onto femur 530. As previously discussed, supports 978-980 bias against femur 530 so as to suspend body 952 off of femur 530 and thus off of the articulation surface. Support 980 is positioned against femur 530 just off of the articular cartilage but in alignment with the trochlear groove. In this position, each guide sleeve 1120 is advanced through the corresponding mounting hole 988 so that the second end 1126 of each guide sleeve butts against the femur 530. Here it is noted that mounting holes 988 are positioned and orientated so that guide sleeves 1120 and screws 990, which pass therethrough, intersect with femur 530 either adjacent to but off of the articulation surface or around the perimeter of the articulation surface. In either event, mounting holes 988 are positioned so that any wear or damage caused by guide sleeves 1120 and screws 990 will not detrimentally affect wear or operation of the articulation surface during normal use of the knee joint.

Furthermore, each mounting hole 988 has a central longitudinal axis 989 along with each screw 990 is intended to extend. Mounting holes 988 are oriented at different angles relative to each other so that merely screwing screws 990 into femur 530 through guide sleeves 1120 positioned within mounting holes 998 causes guide template 1100 to be locked in place. That is, it is not necessary for screws 990 to directly bias guide template 1100 against femur 530. Due to the off-set angles of screws 990 and thus the off-set angles of guide sleeves 1120, it is sufficient if screws 990 merely secure guide sleeves 1120 in place to lock guide template 1100 in place.

Once guide sleeves 1120 are properly positioned, screws 990 are passed down through guide sleeves 1120 and screwed into femur 530. Screws 990 are advanced until flange 1140 biases against first end 1124 of each guide sleeves 1120, thereby securely fixing each guide sleeve 1120 to femur 530. It is noted that flange 1130 of guide sleeves 1120 need not bias against body 952 bounding mounting holes 988. Flanges 1130 primarily function to prevent guide sleeves 1120 from falling through mounting holes 988 during placement of guide template 1100, and in alternative embodiments flanges 1130 can be eliminated.

In part, guide sleeves 1120 function as guides for screws 990. That is, as a result of supports 978-980, the bottom of the mounting holes 988 are spaced above femur 530. This configuration helps ensure proper fitting of guide template 1100 without interference by body 952. However, as a result of the spacing between mounting holes 988 and femur 530, there is the potential for screws 990 to become misaligned from the central longitudinal axis of each corresponding mounting hole 988 as the screw 990 is passed from mounting hole 988 to femur 530. This misalignment can cause binding of the screw 990 against guide template 1100 which in turn can cause unwanted displacement or improper securing of guide template 1100. By using guide sleeves 1120 which extend from mounting holes 988 to or adjacent to femur 530, guide sleeves 1120 help maintain proper orientation and alignment of each screw 990.

Once all of screws 990 are secured in place so that the guide sleeves 1120 are secured in place, guide template 1100 is locked in place. In this position, mount 1160 is removed from base 1102 as depicted in FIG. 50. This is accomplished by rotating handle 1116 so that tip 1118 is unscrewed from body 952 (FIG. 48). Handle 1116 which is still secured to mount 1160 can then be used to remove mount 1160. As a result, supports 978 and 979 are now removed from the articulation surface of femur 530 so that distal end 960 of body 952 is freely suspended over the articulation surface. Again, body 952 is locked in this suspended orientation by the angled placement of screws 990 and guide sleeves 1120. By using modular guide template 1100, this method facilitates proper positioning of guide template 1100 by using the supports but removes any structure from directly contacting the functioning portion of the articulation surface prior to rasping so that the articulation surface is not damaged.

Figure 51:
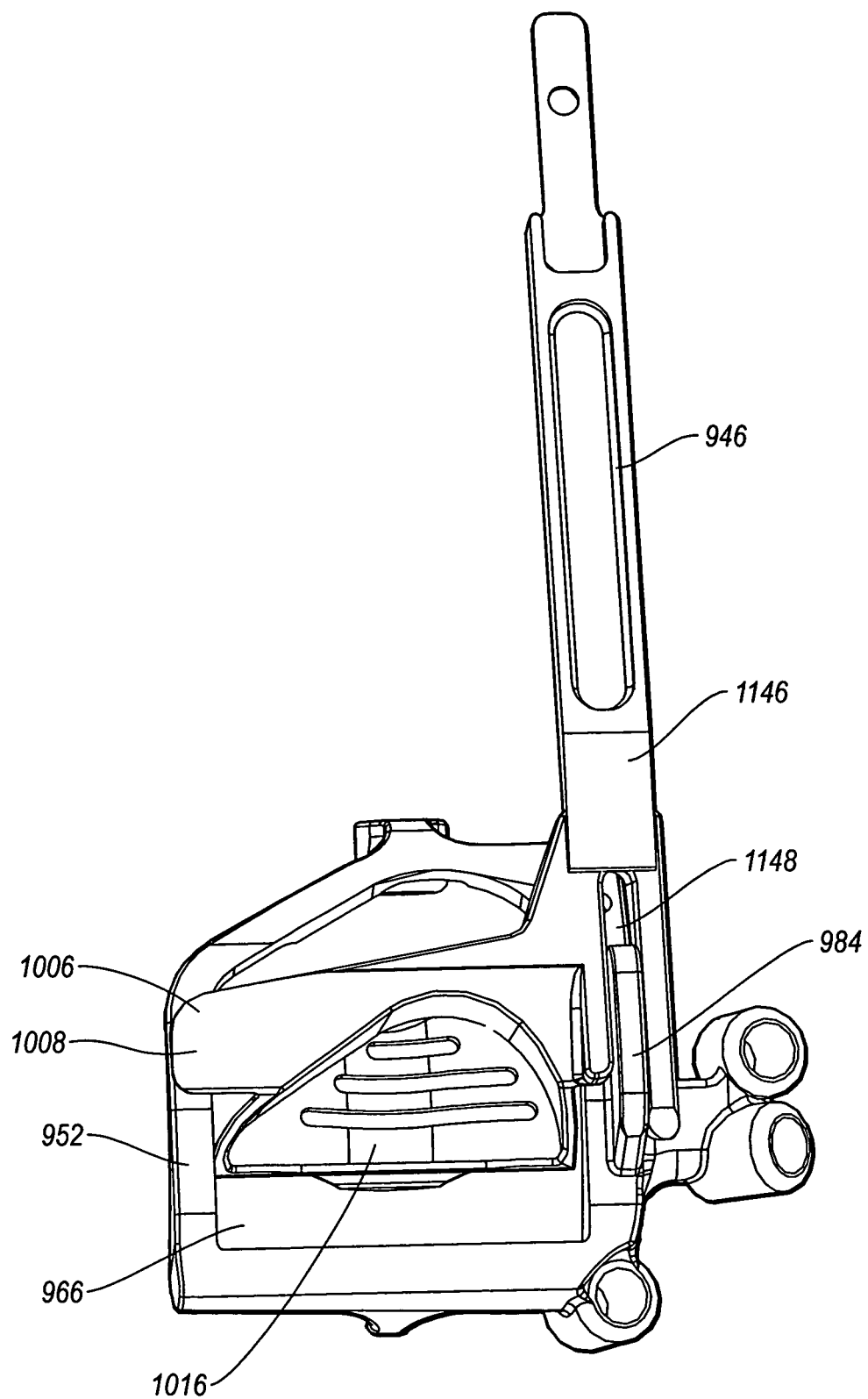
FIG. 51 is a top plan view of the base shown in FIG. 50 with a rasp mounted thereon.
Figure 52:
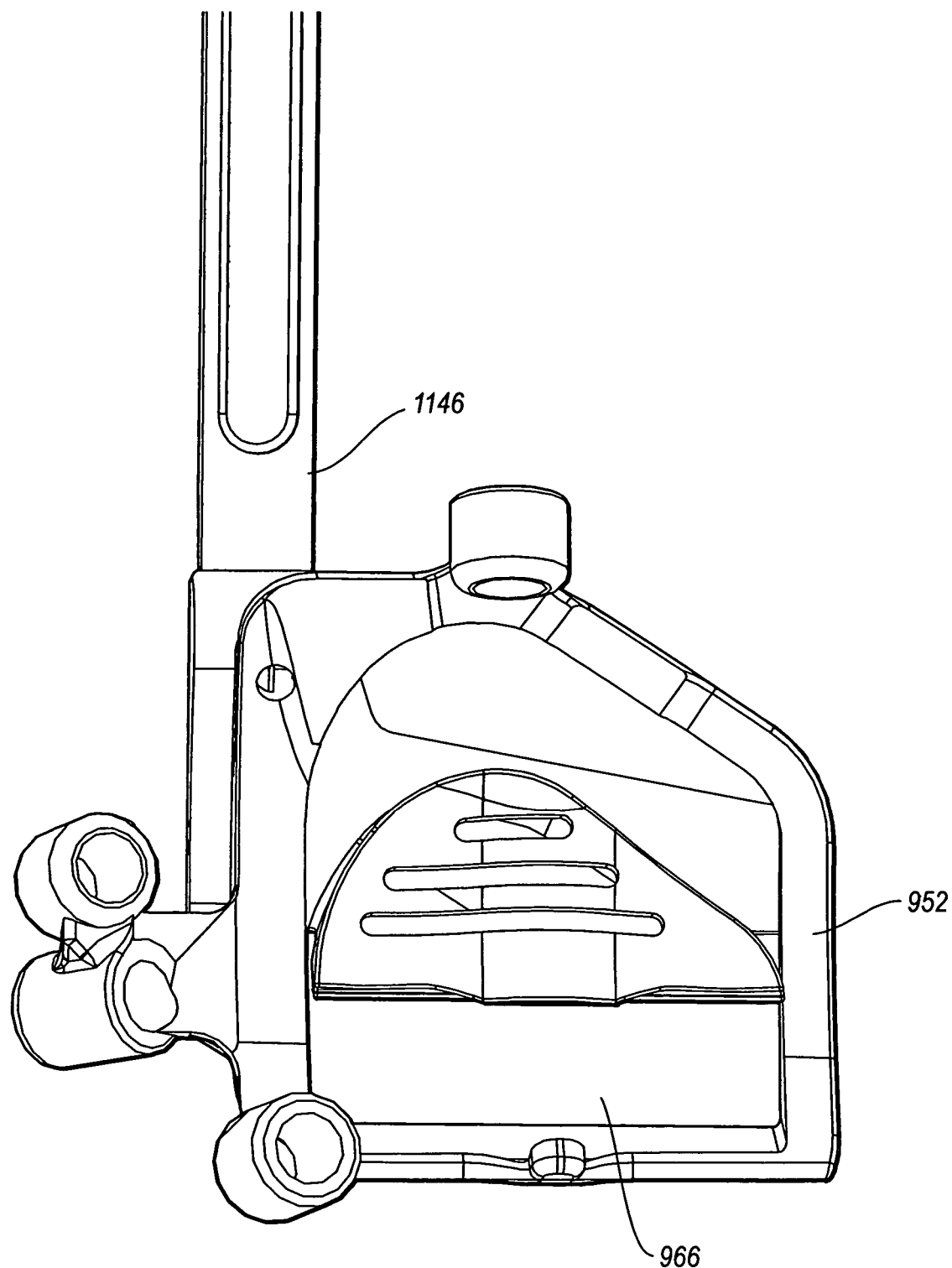
FIG. 52 is a bottom plan view of the base and rasp shown in FIG. 51.

Once mount 1160 is removed, a rasp 1146 as depicted in FIGS. 51 and 52 is positioned on body 952 of guide template 1100 so as to selectively resect the portion of femur 530 bounded by opening 966, thereby forming recessed pocket 942 as depicted in FIG. 40. Rasp 1146 is substantially the same as rasp 994 in that rasp 1146 includes handle 996 and head 1006 which includes slide rest 1008 and cutting mount 1016. However, in contrast to rasp 994, handle 996 is not centrally mounted on head 1006 but is mounted toward a side thereof for more convenience during use. Furthermore, a elongated slot 1148 is formed on head 1006 in alignment with handle 996. During use, cutting mount 1016 is positioned within opening 996 so that guide rail 984 is received within slot 1148. The interaction of guide rail 984 and slot 1148 thus function as a guide for reciprocating movement of rasp 1146 during the formation of recessed pocket 942. Once pocket 942 is formed, rasp 1146 and guide template 1100 are removed. Implant 1064 is then positioned within pocket 942 as previously discussed with regard to FIG. 46.

In addition to the other benefits of the present invention previously discussed, the above apparatus and process has other improvements over the prior art. For example, by using the inventive guide template and rasp, a shallow and precise pocket can be formed to receive the implant with minimal bone removal. The precise pocket provides for improved fitting between the implant and the pocket. Minimizing bone removal simplifies the procedure, minimizes trauma to the bone, and leaves more bone which significantly simplifies subsequent procedures where it may be necessary to replace the implant or perform: a full arthroplasty. Furthermore, the process allows for smaller, thinner implants which can be easily mounted and adjusted.

Figure 53:
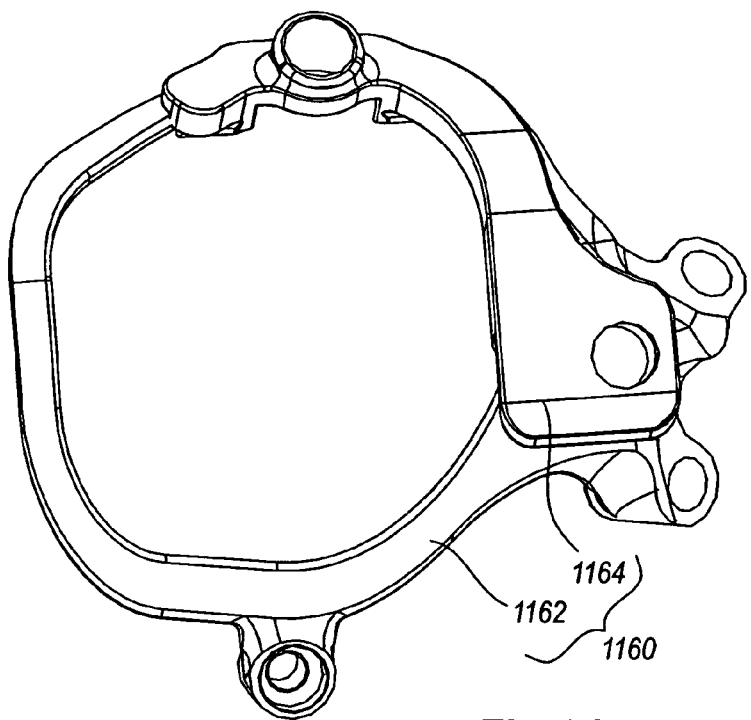
FIG. 53 is a top perspective view of another alternative embodiment of a guide template.

Depicted in FIG. 53 is another alternative embodiment of a guide template 1160 incorporating features of the present invention. Guide template 1160 is used for forming pocket 942 to receive trochlear implant 1064. Like elements between guide templates 1100 and 1160 are identified by like reference characters. Guide template 1160 is also a modular template comprising a base 1162 and a mount 1164 removable connected to base 1162.

Figure 54:
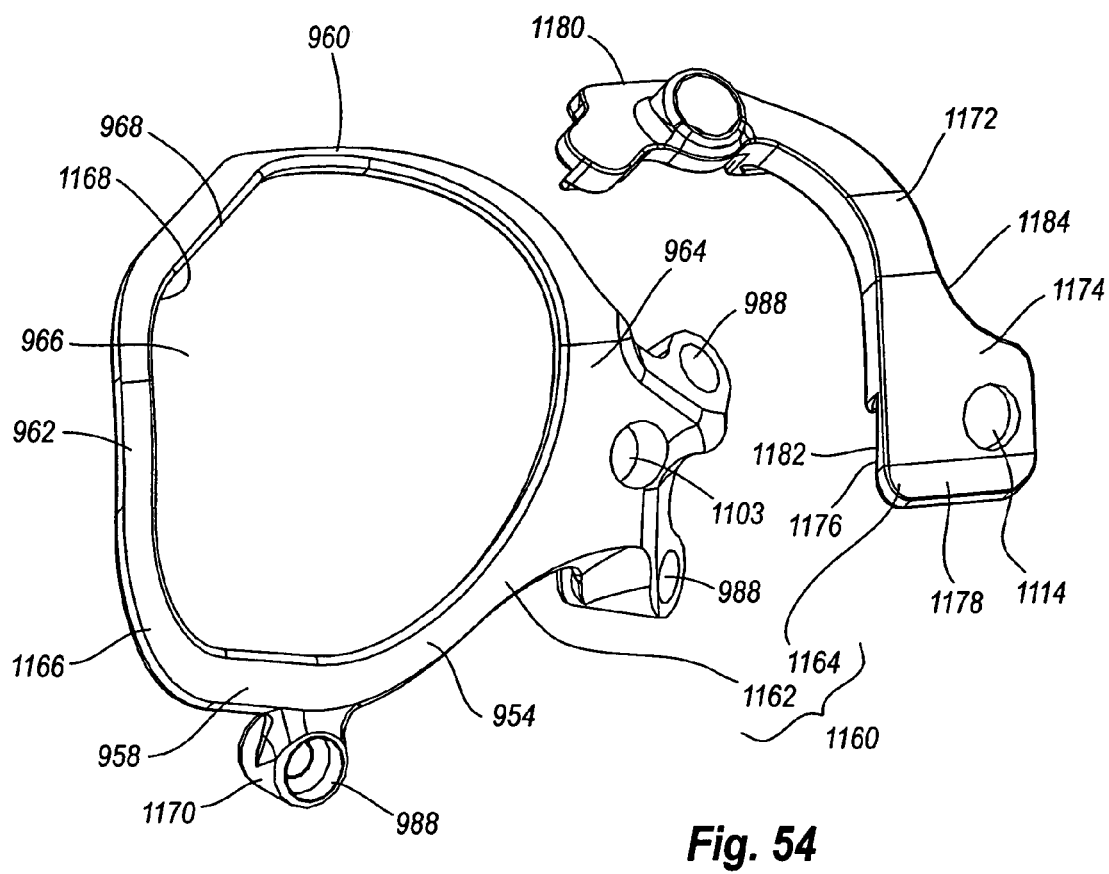
FIG. 54 is a top perspective view of the guide template shown in FIG. 53 in a disassembled state.
Figure 55:
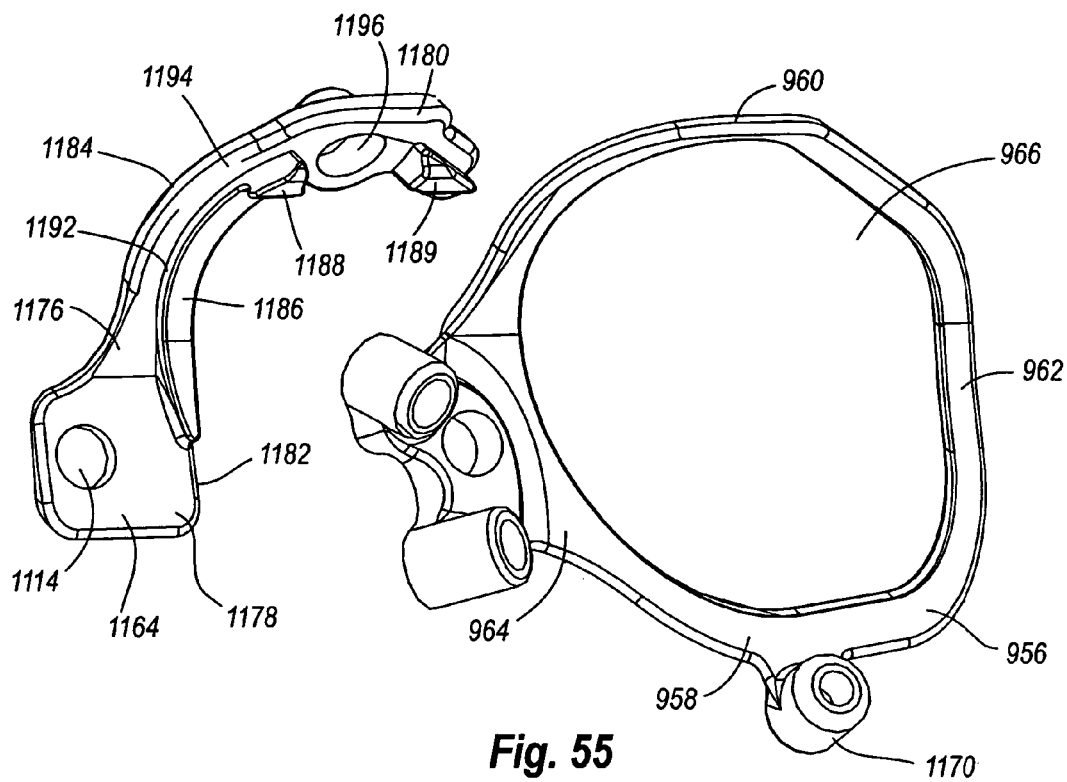
FIG. 55 is a bottom perspective view of the guide template shown in FIG. 53 in a disassembled state.

As depicted in FIGS. 54 and 55, base 1162 comprises a body 1166 having a generally circular or ring shaped configuration. More specifically, body 1166 has sides 962 and 964 extending between proximal end 958 and opposing distal end 960. Body 1166 also has top surface 954 and opposing bottom surface 956. Body 1166 has an interior surface 1168 that bounds opening 966 extending between surfaces 954 and 956. Top surface 954 of sides 962 and 964 has a substantially convex curvature extending between ends 958 and 960. Similarly, bottom surface 958 of sides 962 and 964 has a substantially concave curvature extending between ends 958 and 960. It is noted in this embodiment that both first guide rail 982 and second guide rail 984 (FIG. 32) have been eliminated.

Body 1166 typically has a minimal thickness so as to minimize size and thus simplify insertion within the tissue. In alternative embodiments, however, all or portions of top surface 954 and bottom surface 956 can be substantially flat by increasing the thickness of body 1166.

Projecting from proximal end 958 is a support 1170. In contrast to support 980 of template 1100, support 1170 has a mounting hole 988 extending threrethrough. Two other mounting holes 988 are also formed on side 964. As previously discussed, in one embodiment each mounting hole 988 has a central longitudinal axis that is oriented at a different angle than the others so as to support body 1166 is a suspended position over the bone. Coupling hole 1103 is also formed on side 964 to facilitate removable coupling between base 1162 and mount 1164.

Mount 1164 comprises a brace 1172 having a generally arched, L-shape configuration. Brace 1172 has a top surface 1174 and an opposing bottom surface 1176 each extending between a proximal end 1178 and an opposing distal end 1180. Brace 1172 also has an inside edge 1182 and an opposing outside edge 1184 both extending between surfaces 1174 and 1176. An elongated guide rail 1186 projects from bottom surface 1176 along or adjacent to inside edge 1182. Also projecting from bottom surface 1176 at distal end 1180 are spaced apart supports 1188 and 1189.

Although not required, in the depicted embodiment support 1188 is projecting from the distal end of guide rail 1186. Guide rail 1186 and supports 1188 and 1189 each have an outside face 1192 that is inwardly spaced from outside edge 1184 of brace 1172. As such a portion of bottom surface 1176 extending between outside face 1192 and outside edge 1184 forms a resting surface 1194. Extending through brace 1172 at distal end 1180 at a location between supports 1188 is a mounting hole 1196. A coupling hole 1114 extends through brace 1172 at proximal end 1170.

Figure 56:
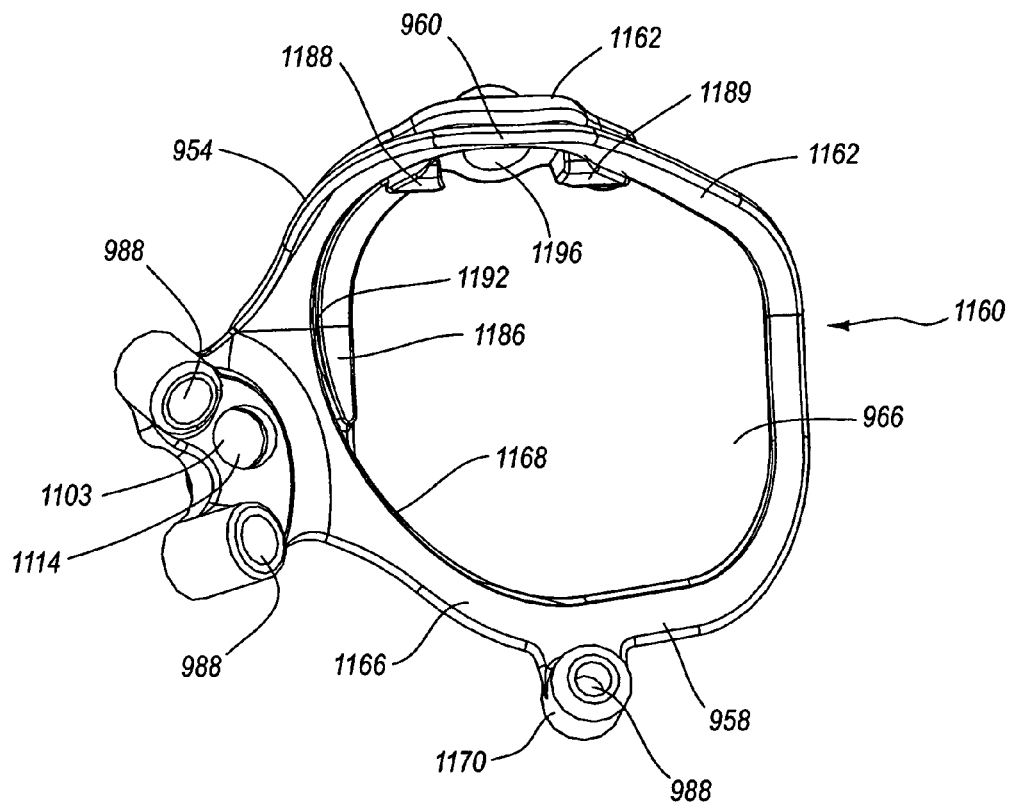
FIG. 56 is a bottom perspective view of the guide template shown in FIG. 53.

Turning to FIG. 56, in the assembled configuration mount 1164 is positioned on base 1162 so that coupling holes 1103 and 1114 are aligned and supports 1188 and 1189 are positioned at distal end 960 of base 1162. More specifically, outside face 1192 of guide rail 1186 and supports 1188 and 1189 are positioned against interior surface 1168 of base 1162 while resting surface 1194 (FIG. 55) of mount 1164 is positioned on top surface 954 of base 1162. Outside face 1192 and interior surface 1168 are typically designed having a complementary configuration so that a close tolerance fit is formed between mount 1164 and base 1162.

In contrast to guide template 1100 where supports 978 and 979 are at least partially positioned outside of opening 966 bounded by base 1102 (FIG. 48), in guide template 1160, supports 1188 and 1189 are positioned completely within opening 966 bounded by base 1162. In further contrast, mounting hole 1196 is formed on mount 1164 rather then base 1162 and is positioned so as to be in alignment with opening 966 as opposed to being outside of opening 966. In alternative embodiments, it is appreciated that two or more mounts can be formed for attachment to base 1102, each mount having a separate support.

In the above assembled configuration, a handle, such as handle 1116 in FIG. 48, is used to removably hold mount 1164 and base 1162 together by passing through coupling holes 1103 and 1114. The assembled guide template 1160 is positioned on femur 530 in substantially the same orientation as guide template 950 in FIG. 32. Specifically, opening 966 of base 1162 is positioned over trochlear groove 539 so that support 1170 is resting on the bone either on the perimeter edge of or just outside of the articular cartilage. Support 1170 is positioned so as to be in alignment with trochlear groove 539. Supports 1188 and 1189 rest against lateral condyle 535 and medial condyle 537, respectively.

In the above mounted position, screws 990 or other fasteners are passed through mounting holes 988 and 1196 so as to secure guide template 1160 to femur 530. It is appreciated that a guide sleeve 1120 (FIG. 50) can be used in association with each of mounting holes 988 and 1196. In this configuration, guide template 1160 is supported on femur 530 by supports 1170, 1188, and 1189 and by screws 990 or other fasteners. It is noted that the mounting holes and associated screw or fasteners comprise means for securing mount 1164 and base 1162 to femur 530. Other removable anchors and fastening techniques can also be used.

Figure 57:
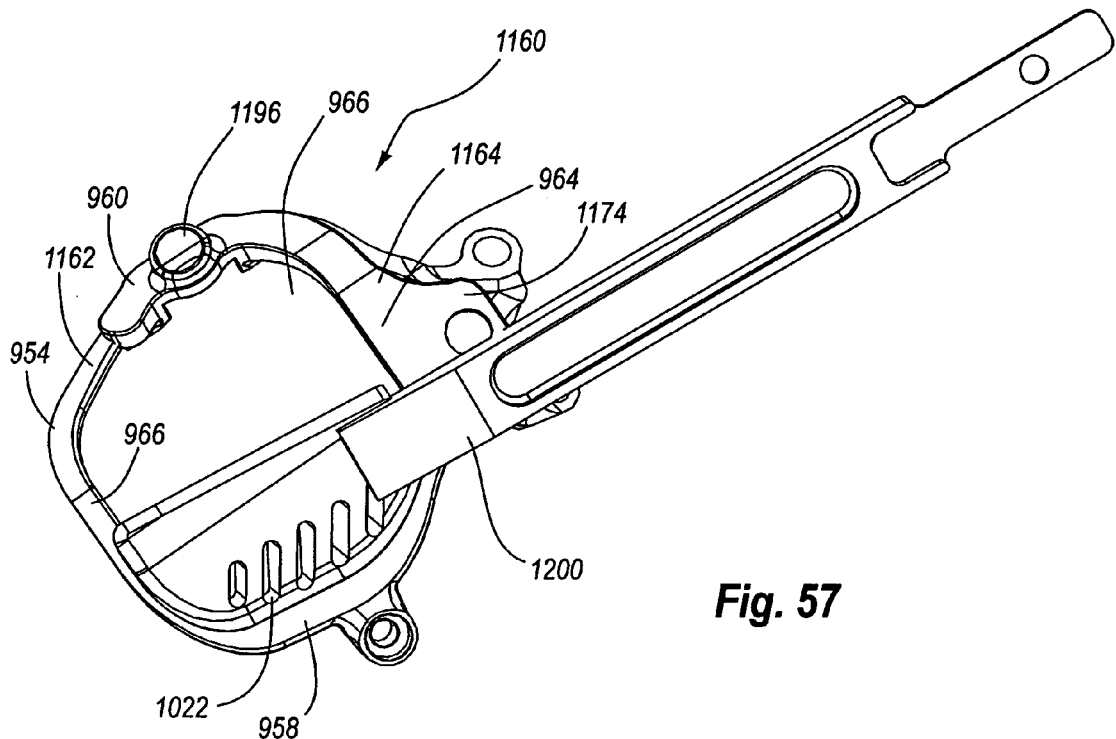
FIG. 57 is a perspective view of the guide template shown in FIG. 53 with an alternative embodiment of a rasp.

Turning to FIG. 57, in contrast to guide template 1100 where mount 1104 is removed prior to rasping, mount 1164 is retained on base 1162 of guide template 1160 during initial rasping or removal of the bone bounded by opening 966. In one embodiment, rasp 1146, as previously discussed with regard to FIG. 51, can be used to remove the bone bounded within opening 966 of guide template 1100. Rasp 1146 is designed to reciprocate along an axis extending between proximal end 958 and distal end 960. Depicted in FIG. 57 is an alternative embodiment of a rasp 1200 incorporating features of the present invention. Rasp 1200 is design to reciprocate along an axis extending between opposing sides 964 and 966. Depending on the situation, different orientations for the rasp may be more convenient for use.

Figure 58:
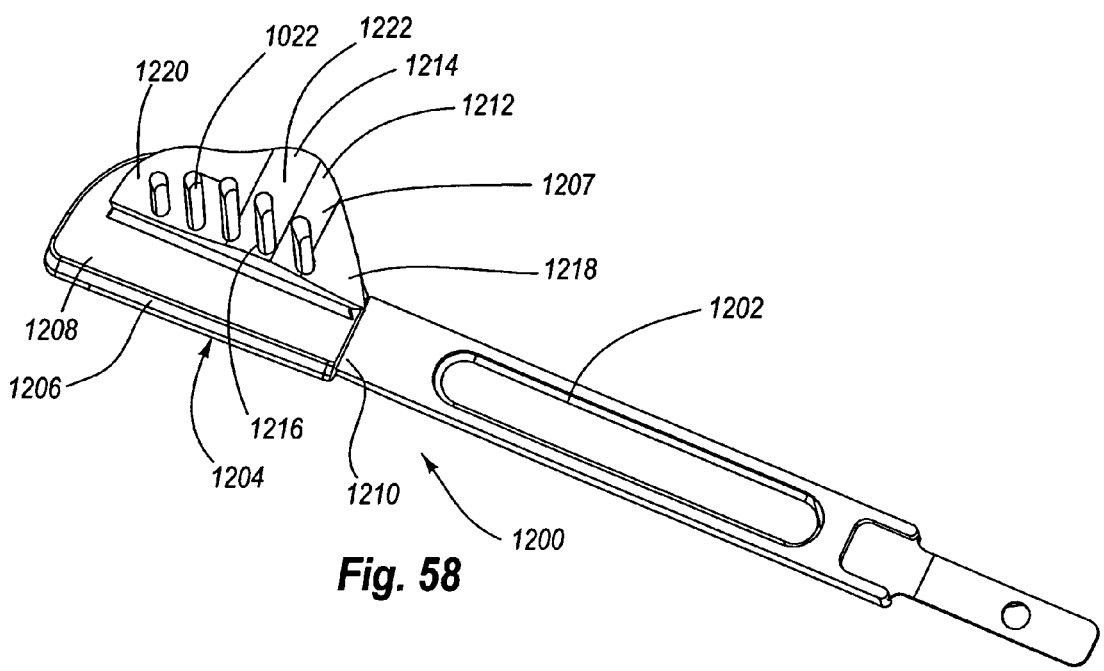
FIG. 58 is a perspective view of the rasp shown in FIG. 57.

As depicted in FIG. 58, rasp 1200 comprises a handle 1202 having a head 1204 mounted on the end thereof. Head 1204 comprises a slide rest 1206 and a cutting mount 1207. Slide rest 1206 has a bottom surface 1208 that is designed to ride on top surface 954 of base 1162. Handle 1202 is set back from bottom surface 1208 so as to form a shoulder 1210 between handle 1202 and head 1204. The formation of shoulder 1210 enables the bottom surface of handle 1202 to ride on top surface 1174 of brace 1172 when slide rest 1206 is riding on base 1162. Here it is noted that once screw 990 is inserted within mounting hole 1196, handle 1116 can temporarily be removed from coupling holes 1103 and 1114 so that handle 1116 does not interfere with rasp 1200.

Cutting mount 1207 has a cutting surface 1212 having apposing sides 1214 and 1216 extending between a proximal end 1218 and an opposing distal end 1220. Cutting surface is comprised of a plurality of teeth, such as teeth 1020 shown in FIG. 37. Because of the orientation of the movement of rasp 1200, a ridge 1222 is formed thereon that extends between opposing sides 1214 and 1216. Ridge 1222 has an apex along the length thereof having a transverse cross section with a convex curve. In addition, the sides of ridge 1222 slope into concave curves on the proximal and distal side of ridge 1222.

By reciprocating rasp 1200 side to side within opening 966 and advancing rasp 1200 between proximal end 958 and distal end 960, recessed pocket 942 as shown in FIG. 40 is substantially formed. In alternative embodiments, rasp 1200 need not be reciprocated but could be moved in a small circular pattern or have other movement to facilitate removal of the bone. Likewise, rasp 1200 could be replaced with a mill or other apparatus to remove the bone. To complete the formation of recessed pocket 942, mount 1164 is removed from base 1162. A rasp, mill or other structure is then used to remove the portion of the bone that was covered by mount 1164. Thus any damage to the articular cartilage that may have previously been caused by supports 1188 and 1189 riding on the articular cartilage during the original rasping or by screw 990 passing through mounting hole 1196 of mount 1164 is irrelevant because that portion of the articular cartilage is removed. Once recessed pocket 942 is complete, base 1162 is removed and implant 1064 is secured therein as previously discussed.

Set forth above are several different embodiments of the present invention. Other embodiments are also disclosed in the '941 application. It is appreciated that the different features of the different embodiments can be mixed and matched to produce a variety of other embodiments within the scope of the present invention. By way of example and not by limitation, each of the different implants can be made with or without an inlay of porous bone ingrowth material on the bone apposition surface; each different implant can have one or more different lines that are connected in one or more different ways; and each different implant can be made as an integral body or two or more separate parts. For example, each implant can comprise a metal tray that is mounted to the bone and a plastic bearing plate that is mounted to the tray. It is likewise appreciated that the different methods steps for the different embodiments can also be mixed and matched and used with other techniques. For example, the guide template having supports, such as supports 978-980, that are either fixed or removable can be used for resecting any type of articulation surface on any joint. Finally, it is again noted that the implants described herein are only by way of example and not by limitation. The present invention can also be used in association with resurfacing articulation surfaces of other orthopedic joints.

Finally, the above embodiments primarily discuss mounting implants on resected articulation surfaces. On occasion, however, a sufficient portion of a natural articulation surface has been worn down or otherwise removed by events other than surgical resection so that it is not necessary to resect the wear surface which is still functioning as a natural articulation surface. On these occasions, it is envisioned that the implant can be mounted directly on the worn natural articulation surface with minimal or no surgical resection of the articulation surface.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A guide template for use in resurfacing a portion of a bone, the guide template comprising:
    a body adapted for positioning over one of a natural articulation surface and a resected articulation surface of a bone and having a top surface and a bottom surface opposite the top surface, said top surface and said bottom surface extending between a proximal end and an opposing distal end, the body at least partially bounding an opening extending between the top surface and the bottom surface, at least a portion of a surface area of the top surface having a convex curvature and at least a portion of a surface areas of the bottom surface having a concave curvature, said convex curvature and said concave curvature extending between the proximal end and the opposing distal end;
    at least three spaced apart supports projecting below the bottom surface of the body such that the body can be supported by the supports; and
    means for securing the body to the bone.

2. The guide template as recited in claim 1, wherein at least one of the supports is removably connected to the body.

3. The guide template as recited in claim 1, wherein at least two of the supports are removably connected to the body.

4. The guide template as recited in claim 1, further comprising:
    a base comprising the body and having a least one of the supports projecting therefrom; and
    a mount comprising a brace having at least one of the supports projecting therefrom, the mount being removably coupled to the base.

5. The guide template as recited in claim 4, wherein the base has the opening extending therethrough and wherein when the mount is coupled with the base, the at least one support is disposed within the opening.

6. The guide template as recited in claim 1, wherein at least two spaced apart supports are located at the distal end of the body and at least one support is located at the proximal end of the body.

7. The guide template as recited in claim 1, wherein the opening is bounded by an interior surface, the interior surface comprising:
    a substantially linear first side section;
    a substantially linear second side section opposing the first side section;
    a proximal section; and a distal section, the distal section having an asymmetrical curvature.

8. The guide template as recited in claim 1, wherein the opening has an area of at least 2 cm².

9. The guide template as recited in claim 1, wherein the body completely encircles the opening.

10. The guide template as recited in claim 9, wherein the opening is asymmetrical.

11. The guide template as recited in claim 1, wherein the means for securing the body comprises a first hole extending through the body and a first fastener adapted to extend through the first hole.

12. The guide template as recited in claim 11, further comprising a tubular guide sleeve slidably disposed within the first hole, the first fastener adapted to extend through the guide sleeve.

13. The guide template as recited in claim 1, wherein the means for securing the body comprises a plurality of holes formed on the body, each hole having a central longitudinal axis extending therethrough, the central longitudinal axis of each hole being oriented at an angle different than the others.

14. The guide template as recited in claim 13, further comprising a tubular guide sleeve slidably disposed within a first hole selected from the plurality of holes, the first hole having a length and the tubular guide sleeve having a length greater than the length of the first hole.

15. The guide template as recited in claim 13, further comprising a plurality of screws, each of the plurality of screws being adapted to be received within a corresponding one of the plurality of holes.

16. The guide template as recited in claim 1, further comprising an elongated first guide rail upwardly projecting from the surface of the body.

17. The guide template as recited in claim 16, further comprising an elongated second guide rail upwardly projecting from the top surface of the body on a side of the opening opposite the first guide rail.

18. A guide template for use in resurfacing a portion of a bone, the guide template comprising:

a base adapted for positioning over one of a natural articulation surface and a resected articulation surface of a bone and having a top surface and an opposing bottom surface that each extend between a proximal end and an opposing distal end, the base at least partially bounding an opening extending between the top surface and bottom surface;

means for securing the base to the bone; and a mount having a first support projecting therefrom, the mount being removably connected to the base so that the first support passes from said top surface through said opening to project below the bottom surface of the base when the mount is connected to the base, the first support resting against the bone when the base is secured to the bone.

19. The guide template as recited in claim 18, further comprising a second support projecting from the mount so that the second support projects below the bottom surface of the base.

20. The guide template as recited in claim 18, further comprising a support connected to the base and projecting below the bottom surface thereof.

21. The guide template as recited in claim 18, wherein at least a portion of the top surface of the base has a convex curvature and wherein at least a portion of the bottom surface of the base has a concave curvature.

22. The guide template as recited in claim 18, wherein the opening is asymmetrical.

23. The guide template as recited in claim 18, wherein the means for securing the base comprises a first hole extending through the body and a first fastener adapted to extend through the first hole.

24. The guide template as recited in claim 23, further comprising a tubular guide sleeve slidably disposed within the first hole, the first fastener adapted to extend through the guide sleeve.

25. The guide template as recited in claim 18, further comprising means for securing the base to the bone.

\* \* \* \* \*